United States Patent
Dahmann et al.

(10) Patent No.: US 9,051,289 B2
(45) Date of Patent: Jun. 9, 2015

(54) PROCESS AND INTERMEDIATES FOR PREPARING GPR40 AGONISTS

(71) Applicants: Georg Dahmann, Warthausen-Birkenhard (DE); Holger Wagner, Mettenberg (DE); Matthias Eckhardt, Biberach an der Riss (DE); Markus Frank, Ulm (DE); Marco Santagostino, Mittelbiberach (DE); Juergen Schnaubelt, Oberhoefen/Warthausen (DE); Uwe Stertz, Biberach an der Riss (DE); Thorsten Pachur, Biberach an der Riss (DE)

(72) Inventors: Georg Dahmann, Warthausen-Birkenhard (DE); Holger Wagner, Mettenberg (DE); Matthias Eckhardt, Biberach an der Riss (DE); Markus Frank, Ulm (DE); Marco Santagostino, Mittelbiberach (DE); Juergen Schnaubelt, Oberhoefen/Warthausen (DE); Uwe Stertz, Biberach an der Riss (DE); Thorsten Pachur, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/494,631

(22) Filed: Sep. 24, 2014

(65) Prior Publication Data

US 2015/0087829 A1   Mar. 26, 2015

(30) Foreign Application Priority Data

Sep. 26, 2013   (EP) .................................... 13186226

(51) Int. Cl.
C07D 307/80 (2006.01)
C07D 407/12 (2006.01)
C07D 405/12 (2006.01)
C07D 513/04 (2006.01)

(52) U.S. Cl.
CPC ............ *C07D 307/80* (2013.01); *C07D 407/12* (2013.01); *C07D 405/12* (2013.01); *C07D 513/04* (2013.01)

(58) Field of Classification Search
CPC ....................................................... C07D 307/80
See application file for complete search history.

(56) References Cited

FOREIGN PATENT DOCUMENTS

WO    2012072691 A1    6/2012

OTHER PUBLICATIONS

International Search Report and Written Opinion for PCT/EP2014070093 mailing date Oct. 24, 2014.

*Primary Examiner* — Bruck Kifle
(74) *Attorney, Agent, or Firm* — Michael P. Morris; Timothy X. Witkowski

(57) ABSTRACT

The present invention relates to compounds of formula I

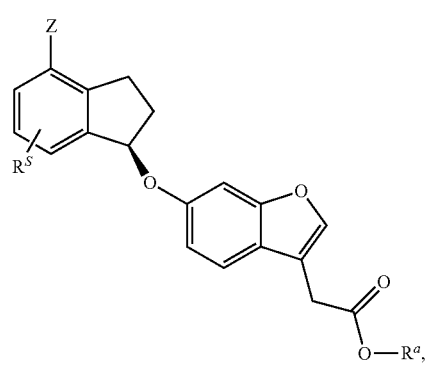

wherein $R^S$ denotes F or $CF_3$, $R^a$ denotes H or $C_{1-4}$-alkyl and Z denotes a leaving group or an optionally substituted or protected hydroxyl group, suitable as intermediates in the synthesis of indanyloxydihydrobenzofuranylacetic acids, which are GPR40 agonists, to a process for preparing these intermediates and to the process for preparing the GPR40 agonists making use of an asymmetric catalytic hydrogenation reaction in the presence of a transition metal catalyst and a chiral auxiliary.

16 Claims, No Drawings

PROCESS AND INTERMEDIATES FOR PREPARING GPR40 AGONISTS

FIELD OF THE INVENTION

The present invention relates to a process for preparing indanyloxydihydrobenzofuranylacetic acids, that are agonists of the G-protein coupled receptor 40 (GPR40, also known as free fatty acid receptor FFAR 1), to intermediates suitable to be used as building blocks in this process and to the process for preparing these intermediates.

BACKGROUND OF THE INVENTION

GPR40 agonists are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia. GPR40 modulators comprising an optically active dihydrobenzofuran ring and processes for their preparation are known in the art, for example, from WO 2008001931 and WO 2012072691. WO 2012111849 describes a method for preparing optically active GPR40 modulators comprising an asymmetric hydrogenation reaction in the presence of a ruthenium complex applied to a benzofuran derivative used as a building block.

OBJECT OF THE PRESENT INVENTION

The object of the present invention is to provide an alternative and improved method for the preparation of indanyloxydihydrobenzofuranylacetic acid derivatives as GPR40 agonists, which is suitable for synthesis on an industrial scale with improved yield, using easily obtainable starting materials of high purity and at a lower technical cost of goods. The intermediates used in the process according to the invention show better crystallinity as the intermediates used within processes in this technical field described in the prior art, thus the intermediates of the invention provide unexpected advantages over the prior art, such as easy and effective purification by crystallization.

SUMMARY OF THE INVENTION

In a first aspect the invention relates to compounds of formula

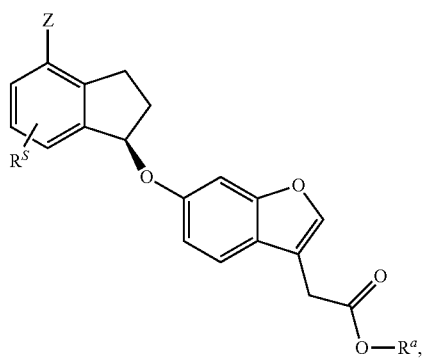

I wherein $R^S$ denotes F or $CF_3$ and $R^a$ denotes H or $C_{1-4}$-alkyl, preferably —$CH_3$, and Z denotes a leaving group, such as Cl, Br, I or a substituted hydroxyl group such as methylsulfonyloxy, phenylsulfonyloxy, p-tolylsulfonyloxy, or trifluoromethylsulfonyloxy, preferably Br, or Z denotes a group selected from OH or protected OH, such as $OCH_3$, $OC(CH_3)_3$, $OSi(C_{1-4}\text{-alkyl})_3$, $OCH_2OC_{1-4}$-alkyl, $OC(=O)$—$C_{1-4}$-alkyl, $OC(=O)$-phenyl, $OCH_2$-phenyl and O-allyl, $B(OH)_2$, $B(OC_{1-4}\text{-alkyl})_2$, $B[OC(CH_3)_2C(CH_3)_2O]$, $B(O_2CCH_2)_2NCH_3$, or $BF_3M$ [M is a cationic metal or ammonium group, such as $Li^+$, $Na^+$, $K^+$, $NH_4^+$, and $^+N(CH_3)_4$], and salts of those compounds wherein $R^a$ denotes H, suitable as intermediates in a process for preparing indanyloxydihydrobenzofuranylacetic acids, that are GPR40 agonists.

In a second aspect the invention relates to a process for preparing the compounds of formula I' wherein $R^S$ denotes F or $CF_3$ and $R^a$ denotes H or $C_{1-4}$-alkyl, characterized by the following substitution reaction:

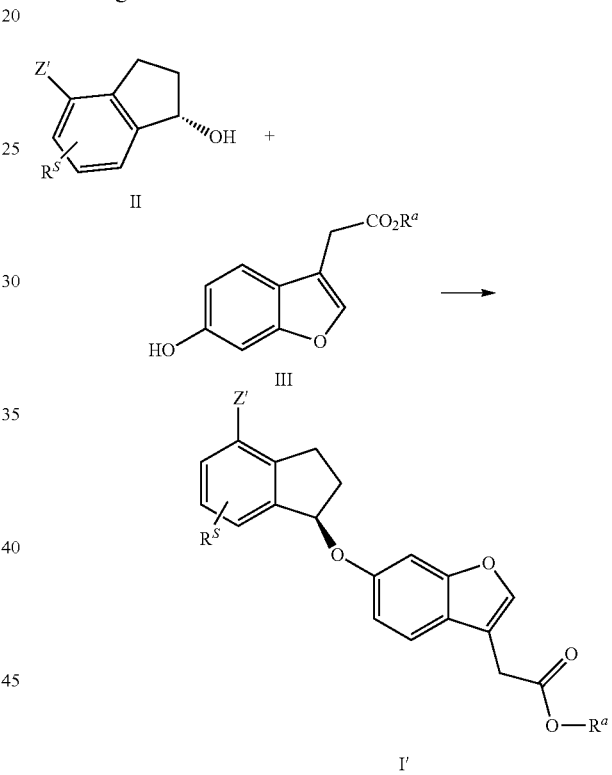

wherein $R^a$ denotes $C_{1-4}$-alkyl, preferably —$CH_3$, and

Z' denotes a leaving group, such as Cl, Br, I or a substituted hydroxyl group such as methylsulfonyloxy, phenylsulfonyloxy, p-tolylsulfonyloxy, or trifluoromethylsulfonyloxy, preferably Br, or Z' denotes a group selected from protected OH, such as $OCH_3$, $OC(CH_3)_3$, $OSi(C_{1-4}\text{-alkyl})_3$, $OCH_2OC_{1-4}$-alkyl, $OC(=O)$—$C_{1-4}$-alkyl, $OC(=O)$-phenyl, $OCH_2$-phenyl and O-allyl, $B(OH)_2$, $B(OC_{1-4}\text{-alkyl})_2$, $B[OC(CH_3)_2C(CH_3)_2O]$, $B(O_2CCH_2)_2NCH_3$, or $BF_3M$ [M is a cationic metal or ammonium group, such as $Li^+$, $Na^+$, $K^+$, $NH_4^+$, and $^+N(CH_3)_4$]

and optionally subsequent ester cleavage to form compounds wherein $R^a$ denotes H.

In a third aspect the invention relates to a process for preparing indanyloxydihydrobenzofuranylacetic acids of the following formulae IV.I to IV.III

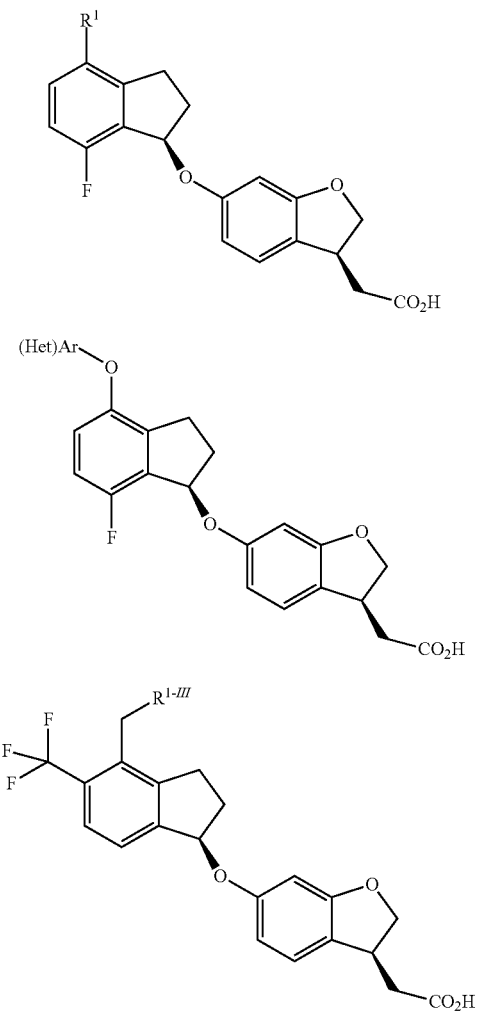

wherein in formula IV.I

R$^1$ is selected from the group R$^1$-G1 consisting of a phenyl ring, a tetrazolyl ring, and a 5- or 6-membered heteroaromatic ring which contains 1, 2, or 3 heteroatoms independently of each other selected from =N—, —NH—, —O— and —S—;

wherein optionally a second ring is annulated to the phenyl or heteroaromatic ring, wherein the second ring is 5- or 6-membered, partially unsaturated or aromatic and may contain 1, 2, or 3 heteroatoms independently of each other selected from =N—, —NH—, —O— and —S— with the proviso that only up to two of the heteroatoms are O and S and no O—O, S—S, and S—O bond is formed, and wherein in the second ring independently of the presence of heteroatoms 1 or 2 CH$_2$ groups may be replaced by —C(=O)—, —S(=O)— or —S(=O)$_2$—, and wherein the phenyl ring, tetrazolyl ring, heteroaromatic ring, annulated phenyl ring, and annulated heteroaromatic ring are substituted with one group R$^3$; and wherein each of the phenyl ring, tetrazolyl ring, heteroaromatic ring, annulated phenyl ring, and annulated heteroaromatic ring is optionally additionally substituted with 1 to 4 groups independently selected from R$^4$; and wherein in the heteroaromatic ring and/or the second ring the H-atom in one or more NH groups, if present, is replaced by R$^N$ or R$^3$;

R$^3$ is selected from the group R$^3$-G1 consisting of
C$_{1-6}$-alkyl, C$_{2-6}$-alkenyl, C$_{2-6}$-alkinyl, C$_{3-6}$-cycloalkyl, C$_{1-4}$-alkyl-NH—, (C$_{1-4}$-alkyl)$_2$N—, C$_{1-6}$-alkyl-O—, C$_{3-6}$-cycloalkyl-O—, C$_{1-4}$-alkyl-S—, C$_{1-4}$-alkyl-S(=O)—, and C$_{1-4}$-alkyl-S(=O)$_2$—, wherein each alkyl and cycloalkyl group and each alkyl and cycloalkyl sub-group within the groups mentioned is substituted with 1 to 3 groups independently selected from R$^5$ and optionally substituted with 1 or more F atoms;

or from C$_{1-4}$-alkyl-C(=O)—, heterocyclyl-C(=O)—, HNR$^N$—C(=O)—, C$_{1-4}$-alkyl-NR$^N$—C(=O)—, C$_{3-6}$-cycloalkyl-NR$^N$—C(=O)—, heterocyclyl-NR$^N$—C(=O)—, phenyl-NR$^N$—C(=O)—, heteroaryl-NR$^N$—C(=O)—, HO$_2$C—, C$_{1-4}$-alkyl-O—C(=O)—, C$_{3-6}$-cycloalkyl-O—C(=O)—, heterocyclyl-O—C(=O)—, —NHR$^N$, C$_{1-4}$-alkyl-C(=O)NR$^N$—, C$_{3-6}$-cycloalkyl-C(=O)NR$^N$—, heterocyclyl-C(=O)NR$^N$—, phenyl-C(=O)NR$^N$—, heteroaryl-C(=O)NR$^N$—, C$_{1-4}$-alkyl-S(=O)$_2$NR$^N$—, C$_{3-6}$-cycloalkyl-S(=O)$_2$NR$^N$—, heterocyclyl-S(=O)$_2$NR$^N$—, phenyl-S(=O)$_2$NR$^N$—, heteroaryl-S(=O)$_2$NR$^N$—, heterocyclyl-O—, phenyl-O—, heteroaryl-O—, C$_{3-6}$-cycloalkyl-S—, heterocyclyl-S—, phenyl-S—, heteroaryl-S—, C$_{3-6}$-cycloalkyl-S(=O)—, heterocyclyl-S(=O)—, phenyl-S(=O)—, heteroaryl-S(=O)—, C$_{3-6}$-cycloalkyl-S(=O)$_2$—, heterocyclyl-S(=O)$_2$—, phenyl-S(=O)$_2$—, heteroaryl-S(=O)$_2$—, HNR$^N$—S(=O)$_2$—, C$_{1-4}$-alkyl-NR$^N$—S(=O)$_2$—, heterocyclyl, phenyl, and heteroaryl, wherein each alkyl, cycloalkyl, and heterocyclyl group or sub-group within the groups mentioned is optionally substituted with 1 to 3 groups independently selected from R$^5$ and optionally substituted with 1 or more F atoms; and wherein each phenyl and heteroaryl group is optionally substituted with 1 to 5 substituents independently selected from R$^6$;

wherein heterocyclyl is selected from
a cyclobutyl group wherein 1 CH$_2$ group is replaced by —NH— or —O—, a saturated or partially unsaturated C$_{5-7}$-cycloalkyl group wherein 1 CH$_2$ group is replaced by —C(=O)—, —NH—, —O—, —S(=O)— or —S(=O)$_2$— and/or 1 CH group by N;

a saturated or partially unsaturated C$_{5-7}$-cycloalkyl group wherein 1 CH$_2$ group is replaced by —NH— or —O—, a second CH$_2$ group is replaced by —NH—, —C(=O)—, —S(=O)— or —S(=O)$_2$— and/or 1 CH group is replaced by N; and a saturated or partially unsaturated C$_{5-7}$-cycloalkyl group wherein 2 CH$_2$ groups are replaced by —NH— or 1 CH$_2$ group by —NH— and the other by —O— and a third CH$_2$ group is replaced by —C(=O)—, —S(=O)— or —S(=O)$_2$— and/or 1 CH group by N;

wherein heteroaryl is selected from
a tetrazolyl ring, and a 5- or 6-membered heteroaromatic ring which contains 1, 2, or 3 heteroatoms independently of each other selected from =N—, —NH—, —O—, and —S—, wherein in heteroaromatic groups containing a —HC=N— unit this group is optionally replaced by —NH—C(=O)—;

wherein in heteroaryl and heterocyclyl rings with one or more NH groups each of them is replaced by NR$^N$ or NR$^5$, R$^4$ is selected from the group R$^4$-G1 consisting of F, Cl, Br, I, CN, —OH, C$_{1-4}$-alkyl, C$_{3-6}$-cycloalkyl, HO—C$_{1-4}$-alkyl, C$_{1-4}$-alkyl-O—C$_{1-4}$-alkyl, —NR$^N$H, C$_{1-4}$-alkyl-NR$^N$—, C$_{1-4}$-alkyl-O—, C$_{3-6}$-cycloalkyl-O—, C$_{1-4}$-alkyl-O—

$C_{1-4}$-alkyl-O—, $C_{1-4}$-alkyl-S—, $C_{1-4}$-alkyl-S(=O)—, and $C_{1-4}$-alkyl-S(=O)$_2$—, wherein any alkyl and cycloalkyl group or sub-group within the groups mentioned is optionally substituted with 1 or more F atoms;

$R^5$ is selected from the group $R^5$-G1 consisting of Cl, Br, I, $C_{1-4}$-alkyl-, CN, $C_{3-6}$-cycloalkyl, heterocyclyl-O(=O)—, $H_2N$—C(=O)—, $C_{1-4}$-alkyl-NR$^N$—C(=O)—, $O_{3-6}$-cycloalkyl-NR$^N$—C(=O)—, heterocyclyl-NR$^N$—C(=O)—, phenyl-NR$^N$—C(=O)—, heteroaryl-NR$^N$—C(=O)—, HO—C(=O)—, $C_{1-4}$-alkyl-O—C(=O)—, —NHR$^N$, $C_{1-4}$-alkyl-C(=O)NR$^N$—, $C_{3-6}$-cycloalkyl-C(=O)NR$^N$—, heterocyclyl-O(=O)NR$^N$—, phenyl-C(=O)NR$^N$—, heteroaryl-C(=O)NR$^N$—, $C_{1-4}$-alkyl-S(=O)$_2$NR$^N$—, $C_{3-6}$-cycloalkyl-S(=O)$_2$NR$^N$—, heterocyclyl-S(=O)$_2$NR$^N$—, phenyl-S(=O)$_2$NR$^N$—, heteroaryl-S(=O)$_2$NR$^N$—, —OH, $C_{1-4}$-alkyl-O—, $C_{1-4}$-alkyl-O—O$_{1-4}$-alkyl-O—, $C_{3-6}$-cycloalkyl-O—, heterocyclyl-O—, phenyl-O—, heteroaryl-O—, $C_{1-4}$-alkyl-S—, $C_{3-6}$-cycloalkyl-S—, heterocyclyl-S—, phenyl-S—, heteroaryl-S—, $C_{1-4}$-alkyl-S(=O)—, $C_{3-6}$-cycloalkyl-S(=O)—, heterocyclyl-S(=O)—, phenyl-S(=O)—, heteroaryl-S(=O)—, $C_{1-4}$-alkyl-S(=O)$_2$—, $C_{3-6}$-cycloalkyl-S(=O)$_2$—, heterocyclyl-S(=O)$_2$—, phenyl-S(=O)$_2$—, heteroaryl-S(=O)$_2$—, $H_2N$—S(=O)$_2$—, $C_{1-4}$-alkyl-NR$^N$—S(=O)$_2$—, heterocyclyl, phenyl, and heteroaryl, wherein any alkyl, cycloalkyl and heterocyclyl group or sub-group within the groups mentioned is optionally substituted with 1 or more F atoms and optionally substituted with 1 or 2 groups independently selected from $H_3O$—, HO—, $H_3C$—O—, and —CN;

wherein heterocyclyl is selected from
- a cyclobutyl group wherein 1 $CH_2$ group is replaced by —NR$^N$— or —O—,
- a saturated or partially unsaturated $C_{5-7}$-cycloalkyl group wherein 1 $CH_2$ group is replaced by —O(=O)—, —NR$^N$—, —O—, —S(=O)— or —S(=O)$_2$— and/or 1 CH group by N;
- a saturated or partially unsaturated $C_{5-7}$-cycloalkyl group wherein 1 $CH_2$ group is replaced by —NR$^N$— or —O—, a second $CH_2$ group is replaced by —NR$^N$—, —O(=O)—, —S(=O)— or —S(=O)$_2$— and/or 1 CH group is replaced by N; and
- a saturated or partially unsaturated $C_{5-7}$-cycloalkyl group wherein 2 $CH_2$ groups are replaced by —NR$^N$— or 1 $CH_2$ group by —NR$^N$— and the other by —O—, and a third $CH_2$ group is replaced by —O(=O)—, —S(=O)— or —S(=O)$_2$— and/or 1 CH group by N;

and wherein heteroaryl is selected from
a tetrazolyl ring, and a 5- or 6-membered heteroaromatic ring which contains 1, 2, or 3 heteroatoms independently of each other selected from =N—, —NH—, —O—, and —S—, wherein in heteroaromatic groups containing a —HC=N— unit this group is optionally replaced by —NR$^N$—C(=O)—, and wherein in heteroaromatic rings with one or more NH groups each of them is replaced by NR$^N$, and each heteroaryl group is optionally substituted with 1 to 3 substituents independently selected from F, Cl, —CH$_3$, —CN, and —O—CH$_3$;

$R^6$ is selected from the group $R^6$-G1 consisting of F, Cl, Br, I, CN, $C_{1-4}$-alkyl, $C_{3-6}$-cycloalkyl-, HO—$C_{1-4}$-alkyl-, $C_{1-4}$-alkyl-O—$C_{1-4}$-alkyl-, R$^N$HN—, $C_{1-4}$-alkyl-O—, —S(=O)—$C_{1-4}$-alkyl, and S(=O)$_2$—$C_{1-4}$-alkyl, wherein any alkyl and cycloalkyl group or sub-group within the groups mentioned is optionally substituted with one or more F atoms; and $R^N$ is independently of each other selected from the group $R^N$-G1 consisting of H, $C_{1-4}$-alkyl, $C_{1-4}$-alkyl-C(=O)—, $C_{1-4}$-alkyl-NH—C(=O)—, $C_{1-4}$-alkyl-N($C_{1-4}$-alkyl)-O(=O)—, $C_{1-4}$-alkyl-O—C(=O)—, and $C_{1-4}$-alkyl-S(=O)$_2$—;

wherein in formula IV.II
(Het)Ar is linked via a carbon atom and is selected from the group (Het)Ar-G1 consisting of phenyl, naphthyl and a mono- or bicyclic heteroaromatic group having 5 to 10 ring member atoms of which 2 to 9 ring members are carbon atoms and either
- one ring member is an unsubstituted or substituted heteroatom selected from N, NH, NR$^{N-II}$, O, S, S(=O) and S(=O)$_2$, or
- one ring member is N and a second ring member is selected from N, NH, NR$^{N-II}$, O, S, S(=O) and S(=O)$_2$, or
- two ring members are N and a third ring member is selected from N, NH, NR$^{N-II}$, O, S, S(=O) and S(=O)$_2$,
    wherein in naphthyl the ring not attached to the indanyl-O atom of formula IV.II may be partially saturated,
    wherein in bicyclic heteroaromatic groups the ring not attached to the indanyl-O atom of formula IV.II may be partially saturated, while at least one aromatic ring includes a heteroatom, and optionally
        one ring member in the partially or fully saturated bridge is replaced by N, NH, NR$^{N-II}$, O, S, S(=O) or S(=O)$_2$, or
        one ring member in the partially or fully saturated bridge is replaced by N, NH or NR$^{N-II}$ and second ring member is replaced by NH, NR$^{N-II}$, O, S, C(=O), S(=O) or S(=O)$_2$, or
        two not vicinal ring members in a fully saturated bridge are replaced by O atoms,
    wherein any of these groups is optionally and independently substituted with 1 to 5 $R^{1-II}$ groups;

$R^{1-II}$ is selected from the group $R^{1-II}$-G1 consisting of F, Cl, Br, I, CN, NO$_2$, NH$_2$, $C_{1-4}$-alkyl-NH—, ($C_{1-4}$-alkyl)$_2$N—, $C_{1-4}$-alkyl, $C_{2-4}$-alkenyl, $C_{2-4}$-alkinyl, OH, HO—$C_{1-4}$-alkyl, $C_{1-4}$-alkyl-O—, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)$_2$—, $C_{3-6}$-cycloalkyl, $C_{3-6}$-cycloalkyl-O—, wherein any alkyl and cycloalkyl group or submoiety is optionally substituted with 1 to 5 F atoms;

$R^{N-II}$ is selected from the group $R^{N-II}$-G1 consisting of $C_{1-4}$-alkyl, $C_{3-4}$-alkenyl, HO—$C_{1-4}$-alkyl, $C_{1-4}$-alkyl-O—$C_{1-4}$-alkyl, $C_{1-4}$-alkyl-C(=O)—, $C_{1-4}$-alkyl-S(=O)$_2$—, and $C_{3-6}$-cycloalkyl-, wherein any alkyl and cycloalkyl group or submoiety is optionally substituted with 1 to 5 F atoms;

wherein in formula IV.III
$R^{1-III}$ is selected from the group $R^{1-III}$-G1 consisting of a monocyclic or bicyclic group having 5 to 12 ring member atoms of which 4 to 11 ring members are C atoms and 1 to 3 ring members are heteroatoms selected from N and NR$^{N-III}$, or
1 or 2 ring members are heteroatoms selected from N and NR$^{N-III}$ and 1 ring member is selected from O and S, or
1 ring member is N and 2 ring members are independently selected from O and S, with the proviso that no O—O, S—S or S—O bond is formed,
    wherein the ring member atom attached to the —CH$_2$— group in formula IV.III is an N atom, wherein 1 CH$_2$ ring member attached to a ring member N atom is optionally replaced by a —C(=O)— group, wherein the monocyclic or bicyclic group is saturated or partially unsaturated, with the proviso that in bicyclic groups the ring attached to the —CH$_2$— group in formula IV.III must not be aromatic, and wherein the bicyclic group may be a fused, bridged or spiro ring system;

wherein any of these groups is optionally and independently substituted with 1 to 3 R$^{2-III}$ groups;

R$^{2-III}$ is selected from the group R$^{2-III}$-G1 consisting of F, Cl, Br, I, C$_{1-4}$-alkyl, NC—, HO—C$_{1-4}$-alkyl, HO—, C$_{1-4}$-alkyl-O—, C$_{1-4}$-alkyl-O—C$_{1-4}$-alkyl, C$_{1-4}$-alkyl-S—, C$_{1-4}$-alkyl-S(=O)—, C$_{1-4}$-alkyl-S(=O)$_2$—, C$_{3-6}$-cycloalkyl-, and C$_{3-6}$-cycloalkyl-O—, wherein any alkyl and cycloalkyl group or submoiety is optionally substituted with 1 to 3 F atoms; and R$^{N-III}$ is selected from the group R$^{N-III}$-G1 consisting of H, C$_{1-4}$-alkyl-, C$_{1-4}$-alkyl-C(O)—, and C$_{1-4}$-alkyl-O—C(O)—;

wherein in any definition mentioned hereinbefore and if not specified otherwise, any alkyl group or sub-group may be straight-chained or branched, comprising the following synthesis steps:

a) asymmetric catalytic hydrogenation reaction in the presence of a transition metal catalyst, such as an Ir, Rh, Ru, Pd or Fe catalyst, preferably an Ir, Rh or Ru catalyst, more preferred a Rh or Ru catalyst, and a chiral auxiliary, optionally in the presence of a base or an acid, applied to a compound of formula I or a salt thereof (in case R$^a$ is H):

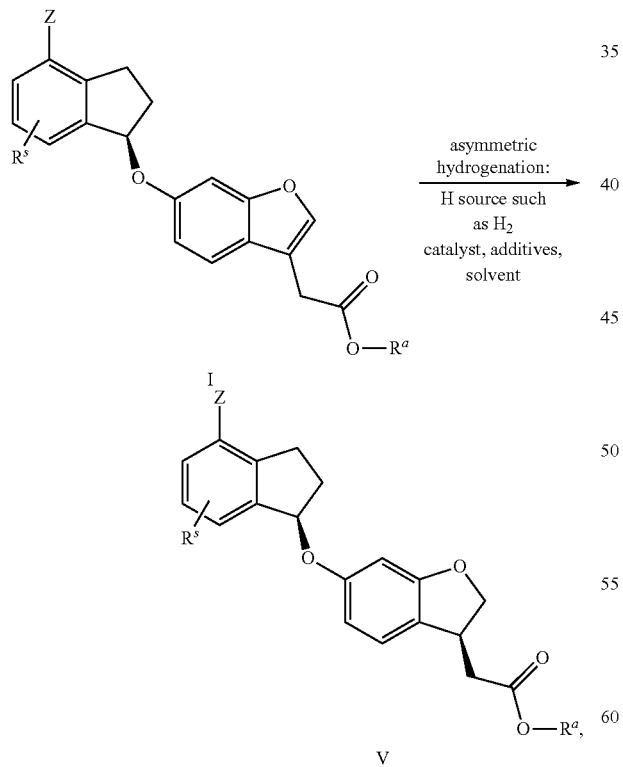

wherein R$^S$ denotes F or CF$_3$ and R$^a$ denotes H or C$_{1-4}$-alkyl, preferably H, and Z denotes a leaving group, such as Cl, Br, I or a substituted hydroxyl group such as methylsulfonyloxy, phenylsulfonyloxy, p-tolylsulfonyloxy, or trifluoromethylsulfonyloxy, preferably Br, or Z denotes a group selected from OH, or protected OH, such as OCH$_3$, OC(CH$_3$)$_3$, OSi(C$_{1-4}$-alkyl)$_3$, OCH$_2$OC$_{1-4}$-alkyl, OC(=O)—C$_{1-4}$-alkyl, OC(=O)-phenyl, OCH$_2$-phenyl and O-allyl, B(OH)$_2$, B(OC$_{1-4}$-alkyl)$_2$, B[OC(CH$_3$)$_2$C(CH$_3$)$_2$O], B(O$_2$CCH$_2$)$_2$NCH$_3$, or BF$_3$M [M is a cationic metal or ammonium group, such as Li$^+$, Na$^+$, K$^+$, NH$_4^+$, and $^+$N(CH$_3$)$_4$], and b) reacting the resulting compound of general formula V, wherein R$^S$ denotes F or CF$_3$ and R$^a$ denotes H or C$_{1-4}$-alkyl, preferably H, and b-1) Z denotes a leaving group such as Cl, Br, I or a substituted hydroxyl group such as methylsulfonyloxy, phenylsulfonyloxy, p-tolylsulfonyloxy, or trifluoromethylsulfonyloxy, preferably Br, with a compound of formula R$^1$—X, wherein R$^1$ is defined as hereinbefore and hereinafter and X denotes B(OH)$_2$, B(OCMe$_2$CMe$_2$O), B(O$_2$CCH$_2$)$_2$NCH$_3$, BF$_3$K, ZnHal, or MgHal (Hal=Cl, Br, I), and subsequent saponification of a compound of formula IV', wherein R$^a$ denotes C$_{1-4}$-alkyl, to form a compound of formula IV

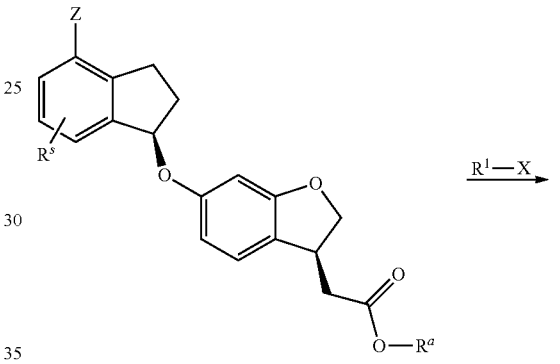

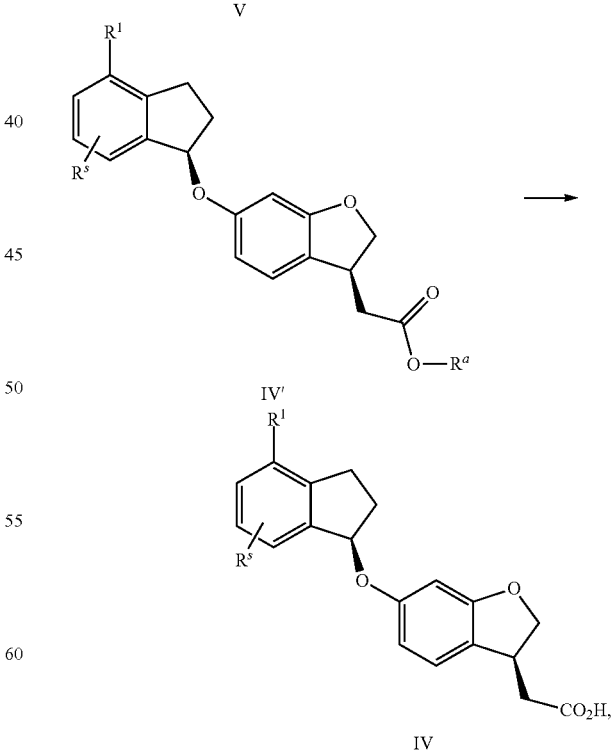

wherein R$^1$ is defined as hereinbefore and hereinafter; or b-2) Z denotes B(OH)$_2$, B(OC$_{1-4}$-alkyl)$_2$, B[OC(CH$_3$)$_2$C(CH$_3$)$_2$O], B(O$_2$CCH$_2$)$_2$NCH$_3$, or BF$_3$M [M is a cationic metal or ammonium group, such as Li⁺, Na⁺, K⁺, NH₄⁺, and ⁺N(CH₃)₄], with a compound of formula R¹—X1, wherein R¹ is defined as hereinbefore and hereinafter and X1 denotes Cl, Br, I, methylsulfonyloxy, phenylsulfonyloxy, p-tolylsulfonyloxy, or trifluoromethylsulfonyloxy, preferably Cl and Br, and subsequent saponification of a compound of formula IV', wherein $R^a$ denotes $C_{1-4}$-alkyl, to form a compound of formula IV ammonium group, such as Li⁺, Na⁺, K⁺, NH₄⁺, and ⁺N(CH₃)₄], preferably Br and B(OH)₂, and subsequent saponification of a compound of formula IV''', wherein $R^a$ denotes $C_{1-4}$-alkyl, to form a compound of formula IV''

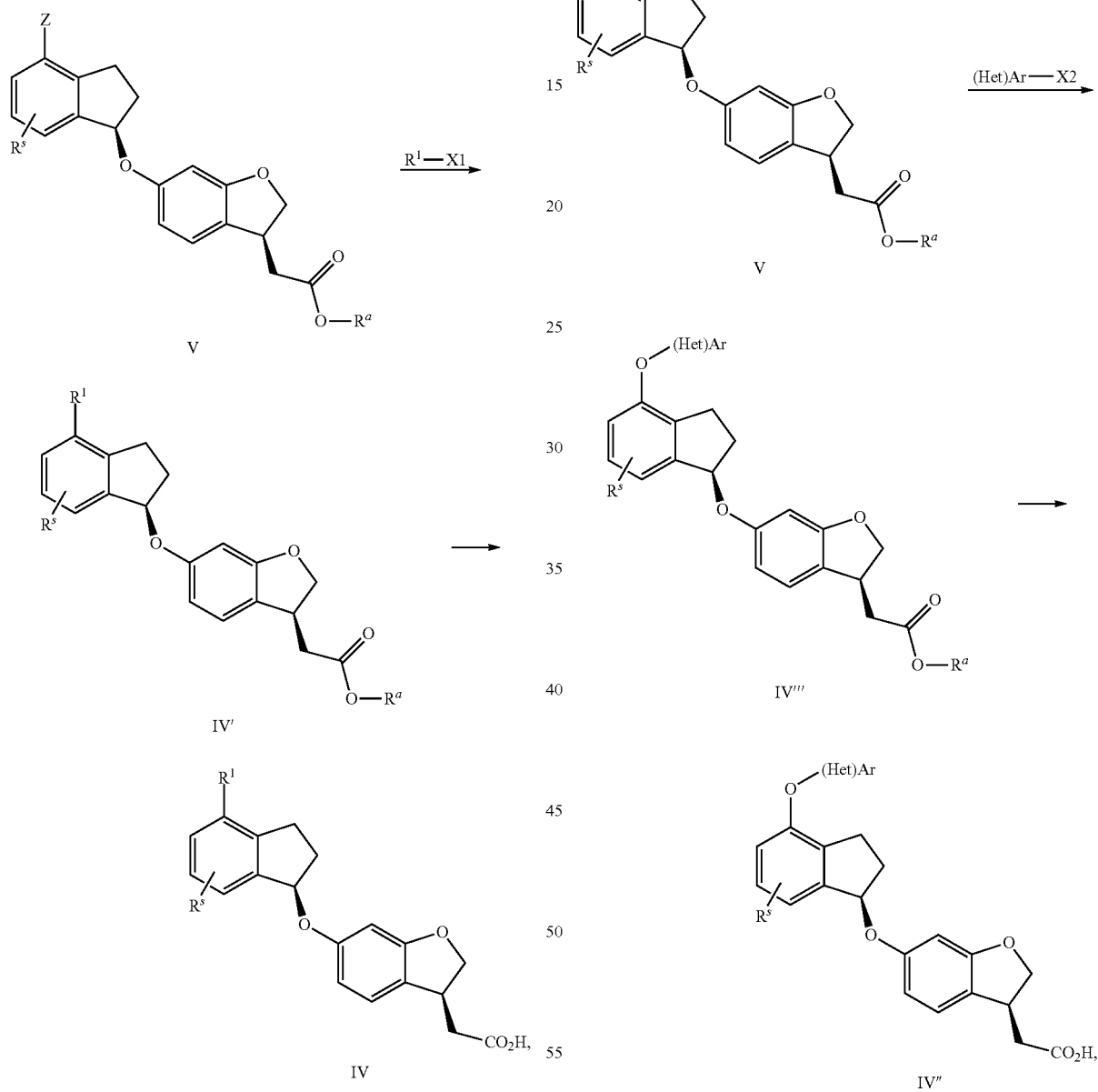

wherein R¹ is defined as hereinbefore and hereinafter; or
b-3) Z denotes OH with a compound of formula (Het)Ar—X2, wherein (Het)Ar is defined as hereinbefore and hereinafter and X2 denotes F, Cl, Br, I, methylsulfonyloxy, phenylsulfonyloxy, p-tolylsulfonyloxy, trifluoromethylsulfonyloxy, B(OH)₂, B(OC₁₋₄-alkyl)₂, B[OC(CH₃)₂C(CH₃)₂O], B(O₂CCH₂)₂NCH₃, or BF₃M [M is a cationic metal or wherein (Het)Ar is defined as hereinbefore and hereinafter; or
b-4) Z denotes Cl, Br, I, methylsulfonyloxy, phenylsulfonyloxy, p-tolylsulfonyloxy, trifluoromethylsulfonyloxy, B(OH)₂, B(OC₁₋₄-alkyl)₂, B[OC(CH₃)₂C(CH₃)₂O], B(O₂CCH₂)₂NCH₃, or BF₃M [M is a cationic metal or ammonium group, such as Li⁺, Na⁺, K⁺, NH₄⁺, and ⁺N(CH₃)₄], preferably Br and B(OH)₂, with a compound of formula (Het)Ar—OH, wherein (Het)Ar is defined as hereinbefore and hereinafter, and subsequent saponification of a compound of formula IV''', wherein $R^a$ denotes $C_{1-4}$-alkyl, to form a compound of formula IV'' compound of formula $IV^V$, wherein $R^a$ denotes $C_{1-4}$-alkyl, to form a compound of formula $IV^{IV}$

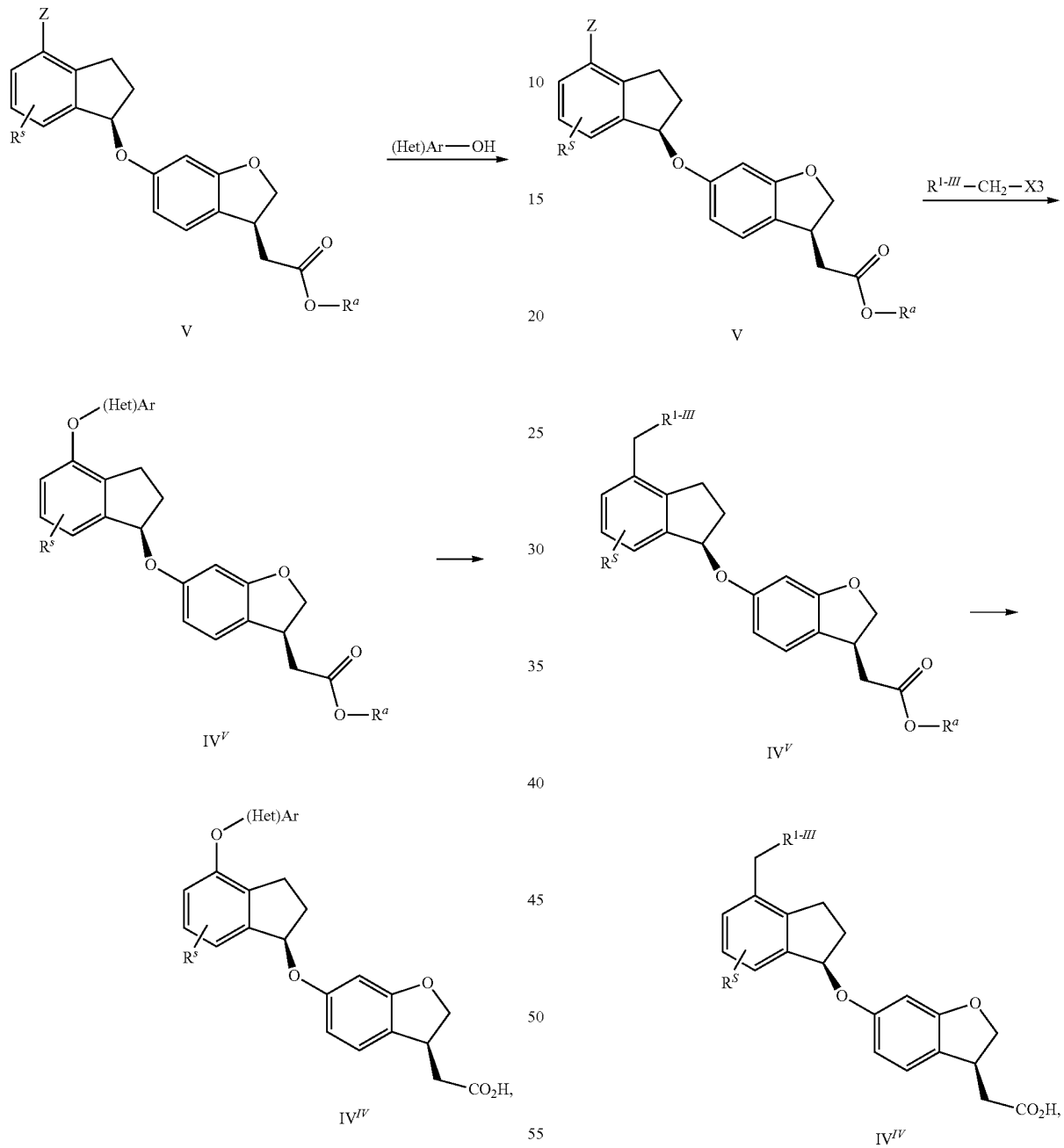

wherein (Het)Ar is defined as hereinbefore and hereinafter; or
b-5) Z denotes Cl, Br, I, methylsulfonyloxy, phenylsulfonyloxy, p-tolylsulfonyloxy, trifluoromethylsulfonyloxy, preferably Br, with a compound of formula $R^{1-III}$—$CH_2$—X3, wherein $R^{1-III}$ is defined as hereinbefore and hereinafter, and X3 denotes $B(OH)_2$, $B(OC_{1-4}$-alkyl$)_2$, $B[OC(CH_3)_2C(CH_3)_2O]$, $B(O_2CCH_2)_2NCH_3$, or $BF_3M$ [M is a cationic metal or ammonium group, such as $Li^+$, $Na^+$, $K^+$, $NH_4^+$, and $^+N(CH_3)_4$], preferably $BF_3K$, and subsequent saponification of a compound of formula $IV^V$, wherein $R^a$ denotes $C_{1-4}$-alkyl, to form a compound of formula $IV^{IV}$ wherein $R^{1-III}$ is defined as hereinbefore and hereinafter.

The expression "optionally substituted with 1 or more F atoms" means that none or one up to successively all H atoms bound to carbon atoms of the respective group or submoiety may be replaced by F atoms, preferably 1 to 5H atoms or, more preferred, 1 to 3H atoms may be replaced by F atoms.

The extension -Gn used within the definitions is meant to identify genus n of the respective substituent. For example, $R^1$-G1 defines genus 1 of the substituent $R^1$.

In a fourth aspect the invention relates to a process for preparing indanyloxydihydrobenzofuranylacetic acids of formula

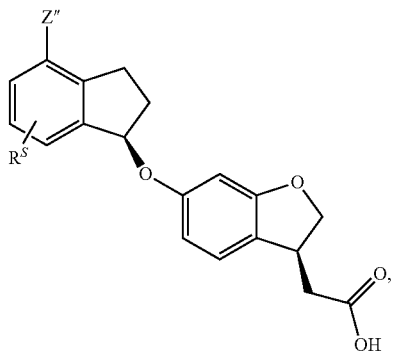

wherein $R^S$ denotes F or $CF_3$ and Z" denotes $R^1$, O-(Het)Ar, and $CH_2$—$R^{1-III}$, which are defined as hereinbefore and hereinafter, comprising the following synthesis steps:

c) reacting the compound of formula I wherein $R^S$ denotes F or $CF_3$ and $R^a$ denotes H or $C_{1-4}$-alkyl and c-1) Z denotes a leaving group, such as Cl, Br, I or a substituted hydroxyl group such as methylsulfonyloxy, phenylsulfonyloxy, p-tolylsulfonyloxy, or trifluoromethylsulfonyloxy, preferably Br, with a compound of formula $R^1$—X, wherein $R^1$ is defined as hereinbefore and hereinafter and X denotes $B(OH)_2$, $B(OCMe_2CMe_2O)$, $B(O_2CCH_2)_2NCH_3$, $BF_3K$, ZnHal, or MgHal (Hal=Cl, Br, I), to form a compound of formula VI,

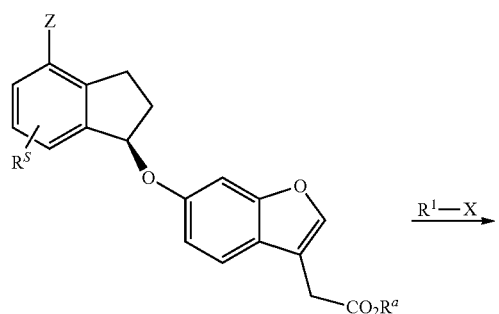

wherein $R^1$ is defined as hereinbefore and hereinafter and $R^a$ denotes H or $C_{1-4}$-alkyl; or c-2) Z denotes $B(OH)_2$, $B(OC_{1-4}\text{-alkyl})_2$, $B[OC(CH_3)_2C(CH_3)_2O]$, $B(O_2CCH_2)_2NCH_3$, or $BF_3M$ [M is a cationic metal or ammonium group, such as $Li^+$, $Na^+$, $K^+$, $NH_4^+$, and $^+N(CH_3)_4$], with a compound of formula $R^1$—X1, wherein $R^1$ is defined as hereinbefore and hereinafter and X1 denotes Cl, Br, I, methylsulfonyloxy, phenylsulfonyloxy, p-tolylsulfonyloxy, or trifluoromethylsulfonyloxy, preferably Cl and Br, to form a compound of formula VI

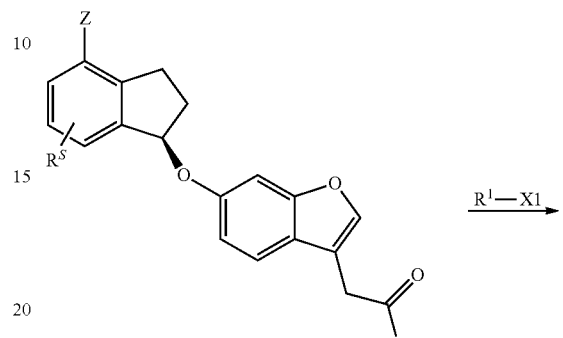

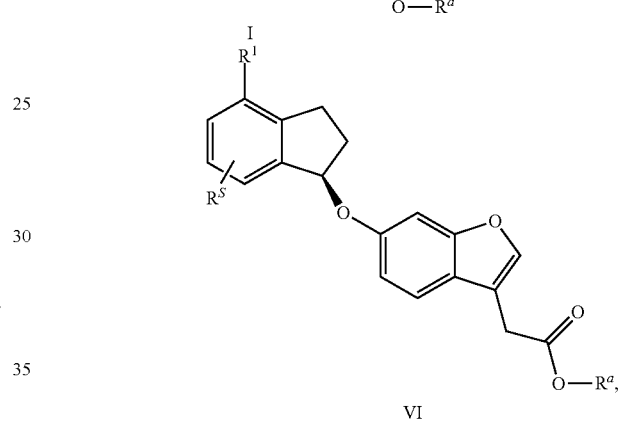

wherein $R^1$ is defined as hereinbefore and hereinafter and $R^a$ denotes H or $C_{1-4}$-alkyl; or c-3) Z denotes OH with a compound of formula (Het)Ar—X2, wherein (Het)Ar is defined as hereinbefore and hereinafter and X2 denotes F, Cl, Br, I, methylsulfonyloxy, phenylsulfonyloxy, p-tolylsulfonyloxy, trifluoromethylsulfonyloxy, $B(OH)_2$, $B(OC_{1-4}\text{-alkyl})_2$, $B[OC(CH_3)_2C(CH_3)_2O]$, $B(O_2CCH_2)_2NCH_3$, or $BF_3M$ [M is a cationic metal or ammonium group, such as $Li^+$, $Na^+$, $K^+$, $NH_4^+$, and $^+N(CH_3)_4$], preferably Br and $B(OH)_2$, to form a compound of formula VI'

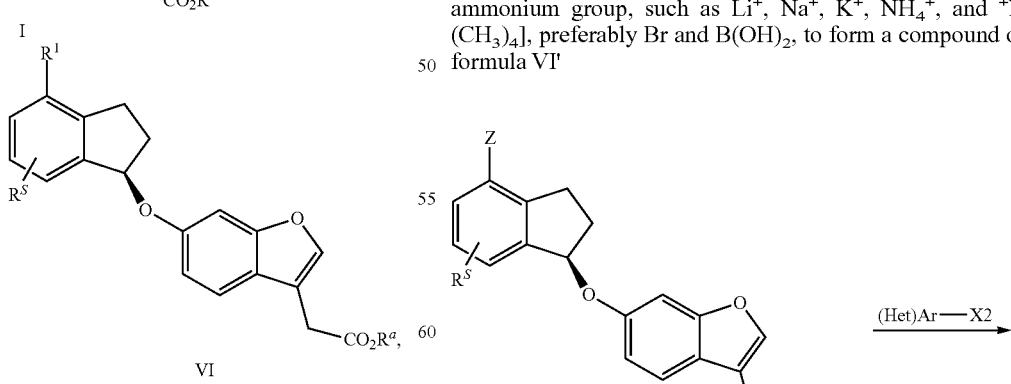

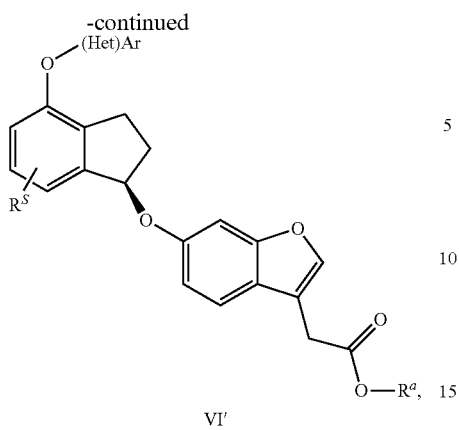

VI' wherein (Het)Ar is defined as hereinbefore and hereinafter and $R^a$ denotes H or $C_{1-4}$-alkyl; or c-4) Z denotes Cl, Br, I, methylsulfonyloxy, phenylsulfonyloxy, p-tolylsulfonyloxy, trifluoromethylsulfonyloxy, $B(OH)_2$, $B(OC_{1-4}\text{-alkyl})_2$, $B[OC(CH_3)_2C(CH_3)_2O]$, $B(O_2CCH_2)_2NCH_3$, or $BF_3M$ [M is a cationic metal or ammonium group, such as $Li^+$, $Na^+$, $K^+$, $NH_4^+$, and $^+N(CH_3)_4$], preferably Br and $B(OH)_2$, with a compound of formula (Het)Ar—OH, wherein (Het)Ar is defined as hereinbefore and hereinafter, to form a compound of formula VI'

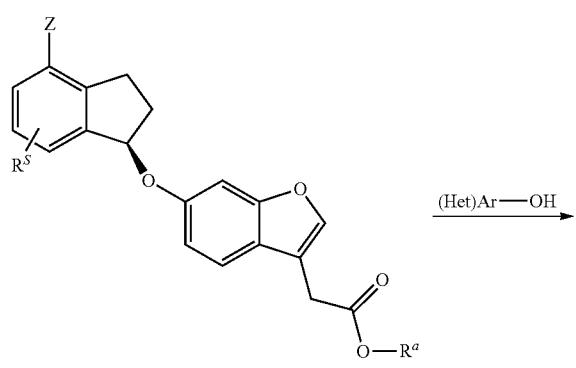

I (Het)Ar—OH →

VI' wherein (Het)Ar is defined as hereinbefore and hereinafter and $R^a$ denotes H or $C_{1-4}$-alkyl; or c-5) Z denotes Cl, Br, I, methylsulfonyloxy, phenylsulfonyloxy, p-tolylsulfonyloxy, trifluoromethylsulfonyloxy, preferably Br, with a compound of formula $R^{1-III}$—$CH_2$—X3, wherein $R^{1-III}$ is defined as hereinbefore and hereinafter, and X3 denotes $B(OH)_2$, $B(OC_{1-4}\text{-alkyl})_2$, $B[OC(CH_3)_2C(CH_3)_2O]$, $B(O_2CCH_2)_2NCH_3$, or $BF_3M$ [M is a cationic metal or ammonium group, such as $Li^+$, $Na^+$, $K^+$, $NH_4^+$, and $^+N(CH_3)_4$], preferably $BF_3K$, to form a compound of formula VI"

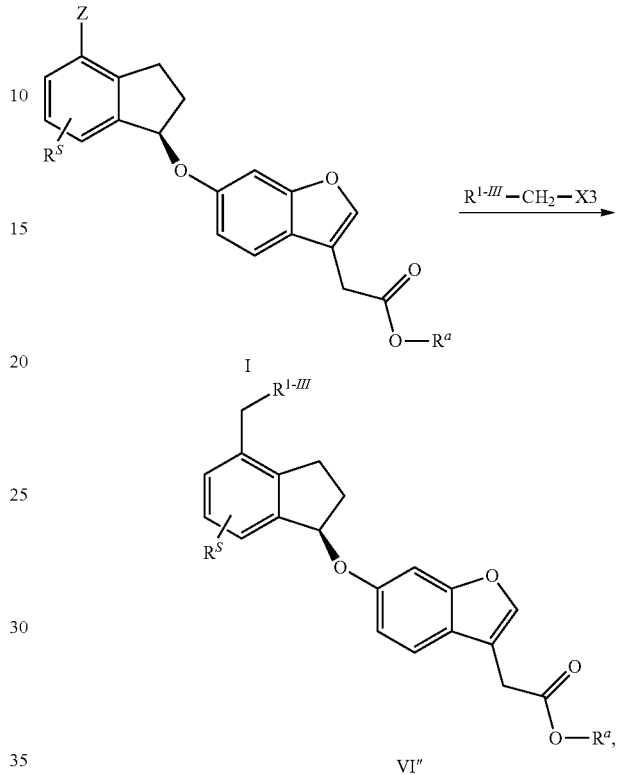

I $R^{1-III}$—$CH_2$—X3 →

VI"

wherein $R^{1-III}$ is defined as hereinbefore and hereinafter and $R^a$ denotes H or $C_{1-4}$-alkyl; and d) asymmetric catalytic hydrogenation reaction in the presence of a transition metal catalyst, such as an Ir, Rh, Ru, Pd or Fe catalyst, preferably an Ir, Rh or Ru catalyst, more preferred a Rh or Ru catalyst, and a chiral auxiliary, optionally in the presence of a base or an acid, applied to a compound of formula I", wherein $R^S$ denotes F or $CF_3$ and Z" denotes $R^1$, O-(Het)Ar, and $CH_2$—$R^{1-III}$, which are defined as hereinbefore and hereinafter, and $R^a$ denotes H or $C_{1-4}$-alkyl.

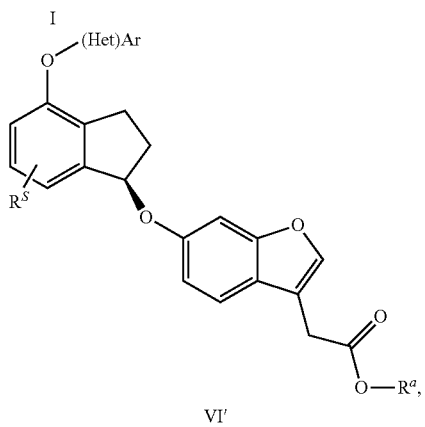

I"

asymmetric hydrogenation: H source such as $H_2$ catalyst, additives, solvent →

-continued

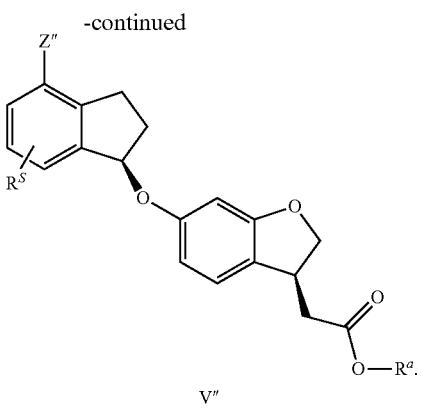

Compounds of formula V''', wherein $R^a$ denotes $C_{1-4}$-alkyl, may be transformed into the corresponding acids wherein $R^a$ is H by conventional saponification.

DETAILED DESCRIPTION OF THE INVENTION

Regarding the third and fourth aspect of the invention relating to processes for preparing indanyloxydihydrobenzofuranylacetic acids of formula IV.I, unless otherwise stated, group $R^1$ of formula IV.I, IV, VI, $R^1$—X and $R^1$—X1 and sub-moieties $R^3$, $R^4$, $R^5$, $R^6$ and $R^N$ as components of $R^1$ are defined as above and hereinafter. If residues, substituents, or groups occur several times in a compound, as for example $R^N$, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

According to one embodiment the group $R^1$ is selected from the group $R^1$-G2 consisting of a phenyl ring, a 5-membered heteroaromatic ring which contains 2 or 3 heteroatoms independently of each other selected from =N—, —NH—, —O— and —S— with the proviso that not more than one heteroatom is —O— or —S—, and a 6-membered heteroaromatic ring which contains 1 or 2 =N— atoms;
wherein optionally a second ring is annulated to the phenyl ring and 5- and 6-membered heteroaromatic rings, wherein the second ring is 5- or 6-membered, partially unsaturated or aromatic and may contain 1 or 2 heteroatoms independently of each other selected from =N—, —NH—, —O— and —S— with the proviso that no O—O, S—S, and S—O bond is formed, and wherein in the second ring independently of the presence of heteroatoms 1 or 2 —CH$_2$— groups may be replaced by —C(=O)— or —S(=O)$_2$—, and
wherein in the heteroaromatic ring and/or the second ring the H-atom in one or more NH groups, if present, is replaced by $R^N$ or $R^3$, and
wherein each of the phenyl ring, heteroaromatic rings, annulated phenyl ring, and annulated heteroaromatic rings is substituted with one group $R^3$ and optionally additionally substituted with 1 or 2 substituents independently selected from $R^4$.

$R^1$-G2a:

According to one embodiment the group $R^1$ is selected from the group $R^1$-G2a consisting of a phenyl ring, a 5-membered heteroaromatic ring which contains 2 or 3 heteroatoms independently of each other selected from =N—, —NH—, —O— and —S—, and a 6-membered heteroaromatic ring which contains 1 or 2 =N— atoms;
wherein in the 5-membered heteroaromatic ring the H-atom in one or more NH groups is replaced with $R^N$ or $R^3$, and
wherein each of the phenyl ring and heteroaromatic rings is substituted with one group $R^3$ and optionally additionally substituted with 1 or 2 substituents independently selected from $R^4$.

$R^1$-G2b:

According to one embodiment the group $R^1$ is selected from the group $R^1$-G2b consisting of a phenyl ring, a 5-membered heteroaromatic ring which contains 2 or 3 heteroatoms independently of each other selected from =N—, —NH—, —O— and —S—, and a 6-membered heteroaromatic ring which contains 1 or 2 =N— atoms, wherein a second 5- or 6-membered, partially unsaturated or aromatic ring is annulated to the phenyl ring and 5- and 6-membered heteroaromatic rings, which may contain 1 or 2 heteroatoms independently of each other selected from =N—, —NH—, —O— and —S— with the proviso that no O—O, S—S, and S—O bond is formed, and wherein in the second ring 1 or 2 —CH$_2$— groups may be replaced by —C(=O)— or —S(=O)$_2$—, and
wherein in the heteroaromatic rings and the second rings the H-atom in one or more NH groups, if present, is replaced by $R^N$ or $R^3$, and
wherein each annulated phenyl ring and annulated heteroaromatic ring is substituted with one group $R^3$ and optionally additionally substituted with 1 or 2 substituents independently selected from $R^4$.

$R^1$-G3:

According to one embodiment the group $R^1$ is selected from the group $R^1$-G3 consisting of:

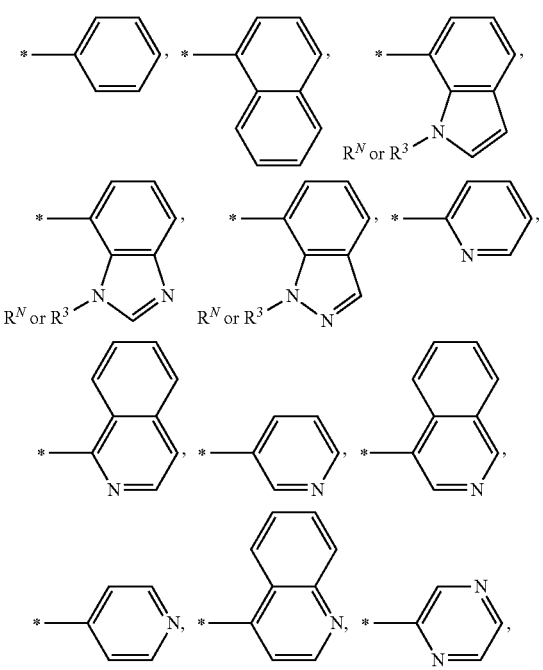

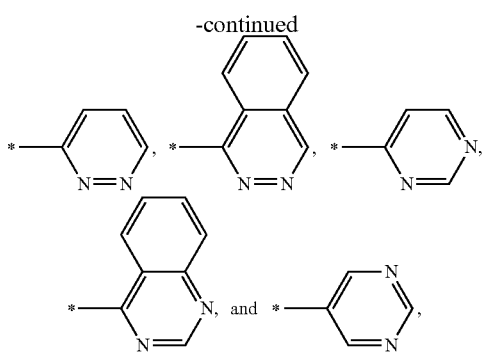

wherein each group is substituted with one group R³ and optionally additionally substituted with 1 or 2 groups independently selected from R⁴.

R¹-G4:

In another embodiment the group R¹ is selected from the group R¹-G4 consisting of

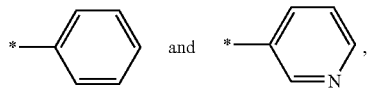

wherein each group is substituted with one group R³ and optionally additionally substituted with 1 or 2 groups independently selected from R⁴.

R¹-G4a:

In another embodiment the group R¹ is selected from the group R¹-G4a consisting of

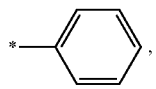

which is substituted with one group R³ and optionally additionally substituted with 1 or 2 groups independently selected from R⁴.

R¹-G5:

In another embodiment the group R¹ is selected from the group R¹-G5 consisting of

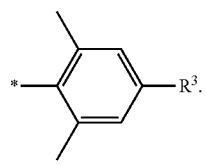

R³:

R³-G1:

The group R³ is preferably selected from the group R³-G1 as defined hereinbefore.

R³-G2:

In another embodiment the group R³ is selected from the group R³-G2 consisting of $C_{1-4}$-alkyl, $C_{3-6}$-cycloalkyl-, $C_{1-4}$-alkyl-O—, $C_{3-6}$-cycloalkyl-O—, $C_{1-4}$-alkyl-S(═O)—, and $C_{1-4}$-alkyl-S(═O)₂—, wherein each alkyl and cycloalkyl group and each alkyl and cycloalkyl sub-group within the groups mentioned is substituted with 1 to 3 groups independently selected from R⁵ and optionally substituted with 1 or more F atoms;

or from heterocyclyl-C(═O)—, HNR^N—C(═O)—, $C_{1-4}$-alkyl-NR^N—C(═O)—, $C_{3-6}$-cycloalkyl-NR^N—C(═O)—, heterocyclyl-NR^N—C(═O)—, phenyl-NR^N—C(═O)—, heteroaryl-NR^N—C(═O)—, $C_{1-4}$-alkyl-C(═O)NR^N—, $C_{3-6}$-cycloalkyl-C(═O)NR^N—, heterocyclyl-C(═O)NR^N—, phenyl-C(═O)NR^N—, heteroaryl-C(═O)NR^N—, $C_{1-4}$-alkyl-S(═O)₂NR^N—, $C_{3-6}$-cycloalkyl-S(═O)₂NR^N—, heterocyclyl-S(═O)₂NR^N—, phenyl-S(═O)₂NR^N—, heteroaryl-S(═O)₂NR^N—, heterocyclyl-O—, phenyl-O—, heteroaryl-O—, $C_{3-6}$-cycloalkyl-S(═O)—, heterocyclyl-S(═O)—, phenyl-S(═O)—, heteroaryl-S(═O)—, $C_{3-6}$-cycloalkyl-S(═O)₂—, heterocyclyl-S(═O)₂—, phenyl-S(═O)₂—, heteroaryl-S(═O)₂—, HNR^N—S(═O)₂—, $C_{1-4}$-alkyl-NR^N—S(═O)₂—, heterocyclyl, phenyl, and heteroaryl, wherein each alkyl, cycloalkyl, and heterocyclyl group or sub-group within the groups mentioned is optionally substituted with 1 to 3 groups independently selected from R⁵ and optionally substituted with 1 or more F atoms; and wherein each phenyl and heteroaryl group is optionally substituted with 1 to 3 substituents independently selected from R⁶;

wherein heterocyclyl is selected from
a cyclobutyl group wherein 1 CH₂ group is replaced by —NH— or —O—, a saturated or mono-unsaturated $C_{5-7}$-cycloalkyl group wherein 1 CH₂ group is replaced by —O(═O)—, —NH—, —O—, —S(═O)— or —S(═O)₂— and/or 1 CH group by N; a saturated or mono-unsaturated $C_{5-6}$-cycloalkyl group wherein 1 CH₂ group is replaced by —NH— or —O—, a second CH₂ group is replaced by —NH—, —C(═O)—, —S(═O)— or —S(═O)₂— and/or 1 CH group is replaced by N; and a saturated or mono-unsaturated $C_{5-6}$-cycloalkyl group wherein 2 CH₂ groups are replaced by —NH— or 1 CH₂ group by —NH— and the other by —O— and a third CH₂ group is replaced by —O(═O)—, —S(═O)— or —S(═O)₂— and/or 1 CH group by N;

wherein heteroaryl is selected from
a tetrazolyl ring, a 5-membered heteroaromatic ring which contains 1, 2, or 3 heteroatoms independently of each other selected from ═N—, —NH—, O, and S, and a 6-membered heteroaromatic ring which contains 1 or 2 ═N— atom, wherein a —HC═N— unit is optionally replaced by —NH—C(═O)—;

and wherein in heteroaryl and heterocyclyl rings with one ore more NH groups each of them is replaced by NR^N or NR⁵.

R³-G3:

In another embodiment the group R³ is selected from the group R³-G3 consisting of $C_{1-4}$-alkyl, $C_{1-4}$-alkyl-O—, and $C_{3-6}$-cycloalkyl-O—, wherein each alkyl and cycloalkyl group and each alkyl and cycloalkyl sub-group within the groups mentioned is substituted with 1 to 3 groups independently selected from R⁵ and optionally substituted with 1 to 3 F atoms;

or from $C_3$-alkyl-S(═O)₂— substituted with 1 HO— or $H_3C$—O— group; and heterocyclyl-O(═O)—, $H_2N$—C(═O)—, HO—$(H_3C)_2C$—$CH_2$—NH—C(═O)—, $C_{1-3}$-alkyl-NR^N—C(═O)—, $C_{1-4}$-alkyl-C(═O)NR^N—, $C_{3-6}$-cycloalkyl-C(═O)NR^N—, heterocyclyl-O(═O)NR^N—, $C_{1-4}$-alkyl-S(═O)₂NR^N—, heterocyclyl-O—, phenyl-O—, heteroaryl-O—, heterocyclyl-S(═O)₂—, heterocyclyl, phenyl, and heteroaryl, wherein each alkyl, cycloalkyl, and heterocyclyl group or sub-group within the groups mentioned is optionally substituted with 1 or 2 groups independently selected from R⁵ and optionally substituted with 1 or more F atoms; and wherein each phenyl and heteroaryl group is optionally substituted with 1 to 3 substituents independently selected from $R^6$;

wherein heterocyclyl is selected from
a cyclobutyl group wherein 1 $CH_2$ group is replaced by —NH— or —O—,
a saturated or mono-unsaturated $C_{5-7}$-cycloalkyl group wherein 1 $CH_2$ group is replaced by —C(=O)—, —NH—, —O— or —S(=O)$_2$— and/or 1 CH group by N;
a saturated or mono-unsaturated $C_{5-6}$-cycloalkyl group wherein 1 $CH_2$ group is replaced by —NH— or —O—, a second $CH_2$ group is replaced by —C(=O)— or —S(=O)$_2$— and/or 1 CH group is replaced by N; and wherein heteroaryl is selected from tetrazolyl, a 5-membered heteroaromatic ring which contains 1, 2, or 3 heteroatoms independently of each other selected from =N—, —NH—, O, and S, and a 6-membered heteroaromatic ring which contains 1 or 2 =N— atoms, wherein a —HC=N— unit is optionally replaced by —NH—C(=O)—;

and wherein in heteroaryl and heterocyclyl rings with one ore more NH groups each of them is replaced by $NR^N$ or $NR^5$.

$R^3$-G3a:

In another embodiment the group $R^3$ is selected from the group $R^3$-G3a consisting of $C_{1-4}$-alkyl-O—, wherein the alkyl group is substituted with 1 to 3 groups independently selected from $R^5$ and optionally substituted with 1 to 3 F atoms; and heteroaryl, wherein the heteroaryl group is optionally substituted with 1 to 3 substituents independently selected from $R^6$;

wherein heteroaryl is selected from
tetrazolyl, a 5-membered heteroaromatic ring which contains 1, 2, or 3 heteroatoms independently of each other selected from =N—, —NH—, O, and S, and a 6-membered heteroaromatic ring which contains 1 or 2 =N— atoms, wherein a —HC=N— unit is optionally replaced by —NH—C(=O)—;

and wherein in heteroaryl and heterocyclyl rings with one ore more NH groups each of them is replaced by $NR^N$ or $NR^5$.

$R^3$-G4:

In another embodiment the group $R^3$ is selected from the group $R^3$-G4 consisting of $C_{1-4}$-alkyl, $C_{1-4}$-alkyl-O—, and $C_{3-6}$-cycloalkyl-O—, wherein each alkyl and cycloalkyl group and each alkyl and cycloalkyl sub-group within the groups mentioned is substituted with 1 group selected from $R^5$ and optionally substituted with 1 or 2 $H_3C$— group;

or from $C_3$-alkyl-S(=O)$_2$— substituted with 1 HO— or $H_3C$—O— group; and heterocyclyl-C(=O)—, $H_2N$—C(=O)—, HO—($H_3C$)$_2$C—$CH_2$—NH—C(=O)—, $H_3C$—NR$^N$—C(=O)—, heterocyclyl-O—, heterocyclyl, phenyl, and heteroaryl, wherein each heterocyclyl group or sub-group within the groups mentioned is optionally substituted with 1 or 2 groups independently selected from $R^5$ and optionally substituted with 1 or more F atoms; and wherein each phenyl and heteroaryl group is optionally substituted with 1 or 2 substituents independently selected from $R^6$;

wherein heterocyclyl is selected from
a cyclobutyl group wherein 1 $CH_2$ group is replaced by —NH— or —O—;
a saturated or mono-unsaturated $C_{5-7}$-cycloalkyl group wherein 1 $CH_2$ group is replaced by —C(=O)—, —NH—, —O— or —S(=O)$_2$— and/or 1 CH group by N;
a saturated or mono-unsaturated $C_{5-6}$-cycloalkyl group wherein 1 $CH_2$ group is replaced by —NH— or —O—, a second $CH_2$ group is replaced by —NH—, —C(=O)— or —S(=O)$_2$— and/or 1 CH group is replaced by N; and wherein heteroaryl is selected from
tetrazolyl, a 5-membered heteroaromatic ring which contains 1 to 3 heteroatoms independently of each other selected from =N—, —NH—, —O—, and —S—, and a 6-membered heteroaromatic ring which contains 1 or 2 =N— atoms, wherein a —HC=N— unit is optionally replaced by —NH—C(=O)—;

wherein in heteroaryl and heterocyclyl rings with one ore more NH groups each of them is replaced by $NR^N$ or $NR^5$.

$R^3$-G5:

According to another embodiment the group $R^3$ is selected from the group $R^3$-G5 consisting of $C_4$-alkyl substituted with 1 HO— and $H_3C$— group;

$C_{2-3}$-alkyl substituted with 1 group selected from $H_3C$—C(=O)—NH—, $H_3C$—S(=O)$_2$—NH— and $H_3C$—S(=O)$_2$—; ($H_3C$)$_3$C—$CH_2$—O—; cyclopropyl-$CH_2$—O— substituted with 1 HO— group; $C_{1-4}$-alkyl-O— optionally substituted with 1 or 2 $H_3C$— groups but necessarily substituted with 1 group selected from NC—, $H_2N$—C(=O)—, $H_3$CNH—C(=O)—, ($H_3C$)$_2$N—C(=O)—, ($H_3C$)$_2$N—, $H_3C$—C(=O)—NH—, ($H_3C$)$_3$C—O—C(=O)—NH—, $H_3C$—S(=O)$_2$—NH—, HO—, $C_{1-2}$-alkyl-O—, $H_3C$—S(=O)—, $H_3C$—S(=O)$_2$—, heterocyclyl, and heteroaryl;

wherein each heterocyclyl group and subgroup is selected from the group consisting of azetidinyl, oxetanyl, pyrrolidin-2-onyl, tetrahydrofuranyl, sulfolanyl, 1,1-dioxoisothiazolidinyl, piperidinyl, tetrahydropyranyl, tetrahydrothiopyranyl, and 1,1-dioxo-tetrahydrothiopyranyl, each of which is optionally substituted with 1 group selected from $H_3C$— and HO—, and wherein a NH group, if present, optionally is replaced by $C_{1-3}$-alkyl-S(=O)$_2$—N; and wherein heteroaryl is selected from the group consisting of imidazolyl, pyrazolyl, oxazolyl, pyridinyl, and pyridin-2-onyl, wherein a NH group, if present, optionally is replaced by N—$CH_3$ and each heteroaryl is optionally substituted with 1 $H_3C$— or $H_3C$—O— group;

$C_{4-5}$-cycloalkyl-O— which is substituted with 1 group selected from —N($CH_3$)S(=O)$_2$$CH_3$ and —OH, and is optionally additionally substituted with 1 $H_3C$— group;

azetidinyloxy, pyrrolidinyloxy, pyrrolidin-2-onyloxy, piperidinyloxy and 1,1-dioxo-[1,2]thiazinanyloxy, in each of which the NH group is optionally replaced by N—$CH_3$ or N—S(=O)$_2$—$CH_3$;

tetrahydrofuranyloxy, tetrahydropyranyloxy, and 1,1-dioxo-tetrahydrothiopyranyloxy; $H_2N$—C(=O)—, $H_3C$—NH—C(=O)—, HO—($H_3C$)$_2$C—$CH_2$—NH—C(=O)—, ($H_3C$)$_2$N—C(=O)—, morpholin-4-yl-C(=O)—, tetrahydrofuranyl, 3,6-dihydropyranyl, 1-methanesulfonyl-1,2,3,6-tetrahydropyridinyl, morpholin-4-yl, [1,4]oxazepan-4-yl, 6-oxo-3,6-dihydropyran-4-yl;

$C_3$-alkyl-S(=O)$_2$— substituted with 1 HO— or $H_3C$—O— group; and phenyl, furanyl, imidazolyl, pyrazolyl, oxazolyl, thiazolyl, triazolyl, oxadiazolyl, tetrazolyl, pyridinyl, pyrimidinyl, pyridazinyl, pyrazinyl, pyridin-2-onyl, pyrimidin-2-onyl, pyrimidin-4-onyl and pyridazin-3-onyl, wherein a NH group, if present, optionally is replaced by N—$CH_3$, N—$CH_2$—C($CH_3$)$_2$—OH or N—C($CH_3$)$_2$—$CH_2$—OH, and which are optionally substituted with 1 H₃C— group and optionally substituted with 1 group selected from —CH₃, —CH₂—CH₃, cyclopropyl, —C(CH₃)₂—OH, and —O—CH₃.
R³-G6:
According to another embodiment the group R³ is selected from the group R³-G6 consisting of
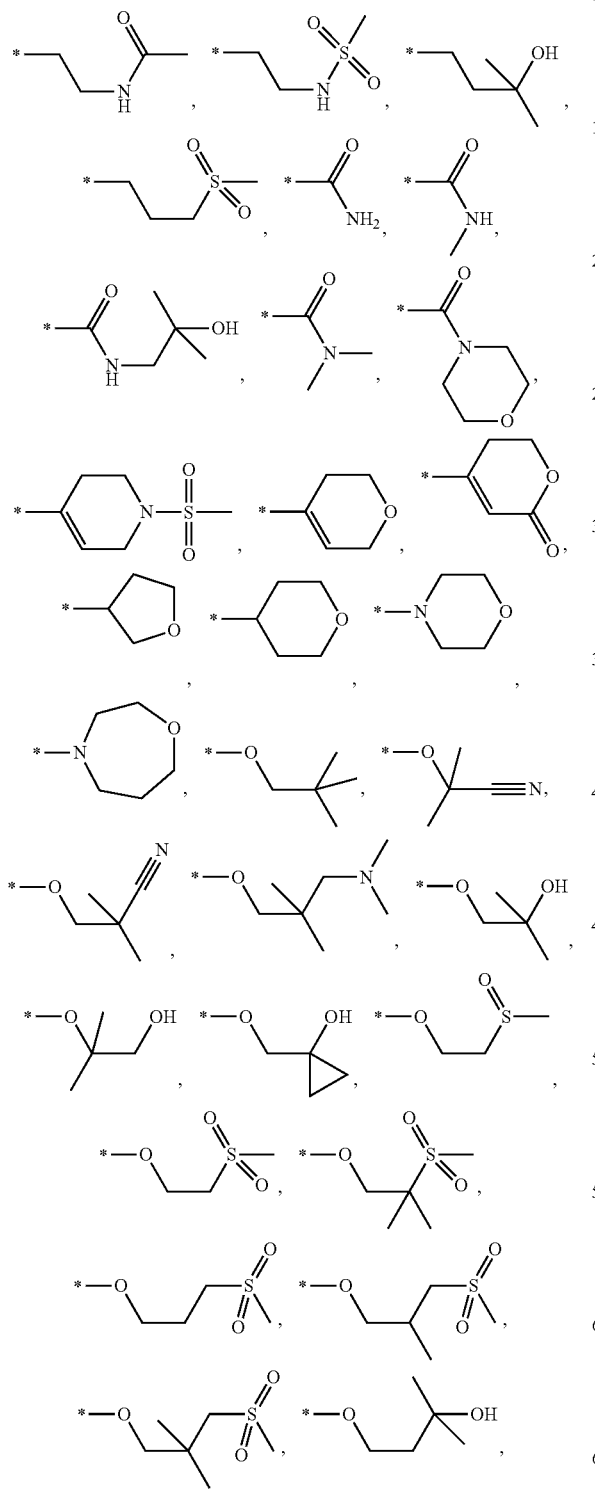
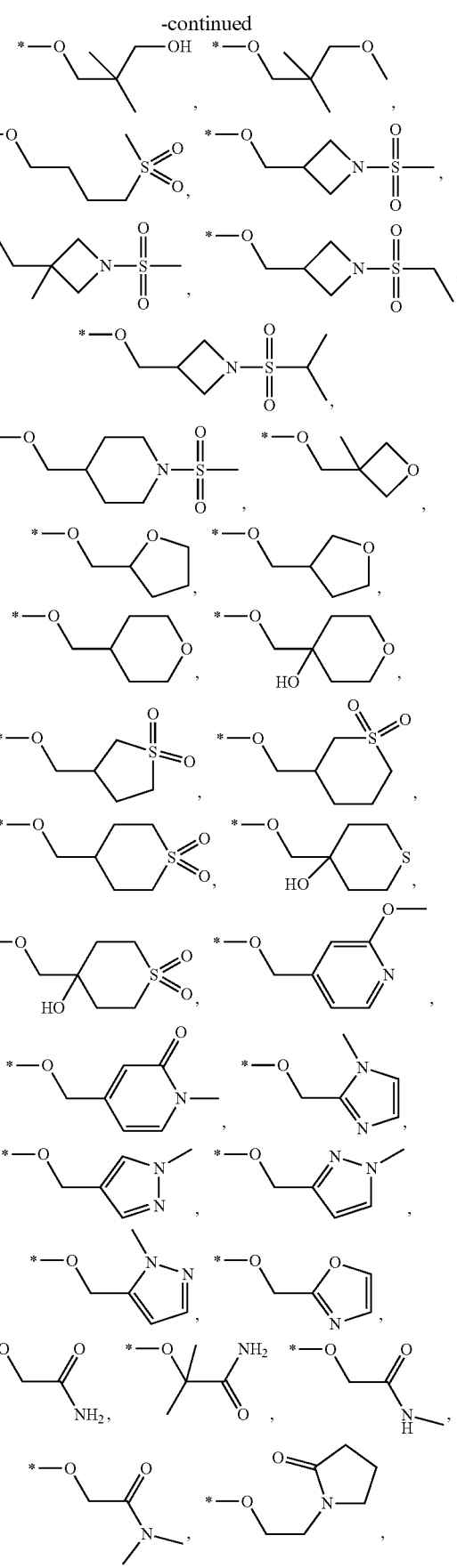

25
-continued
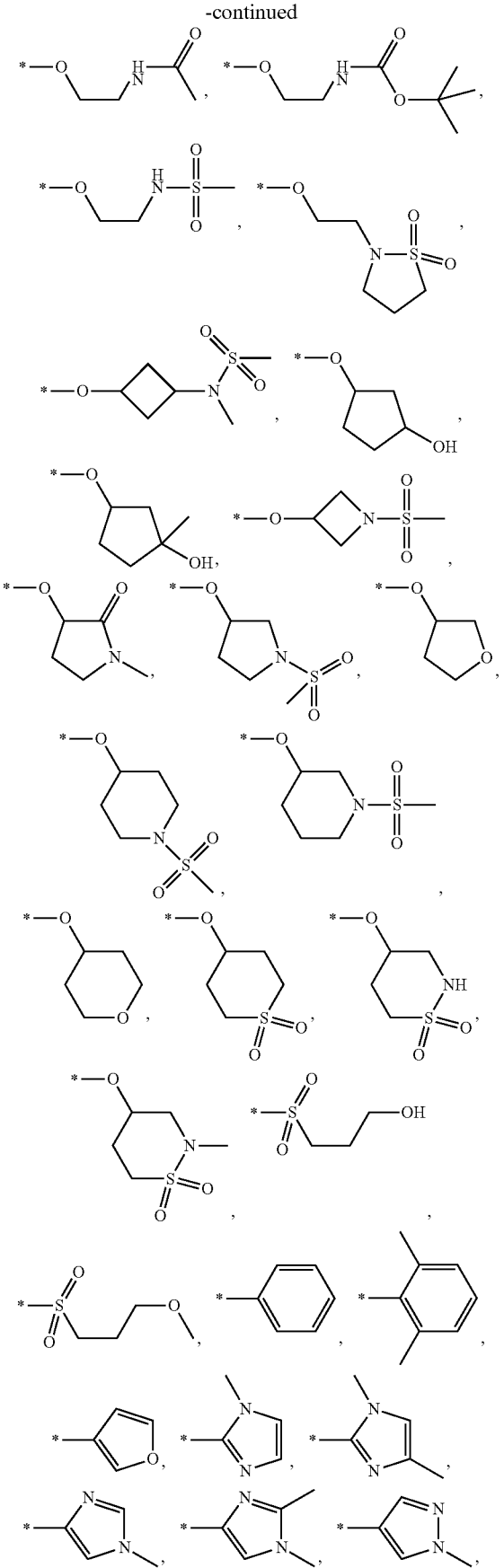
26
-continued
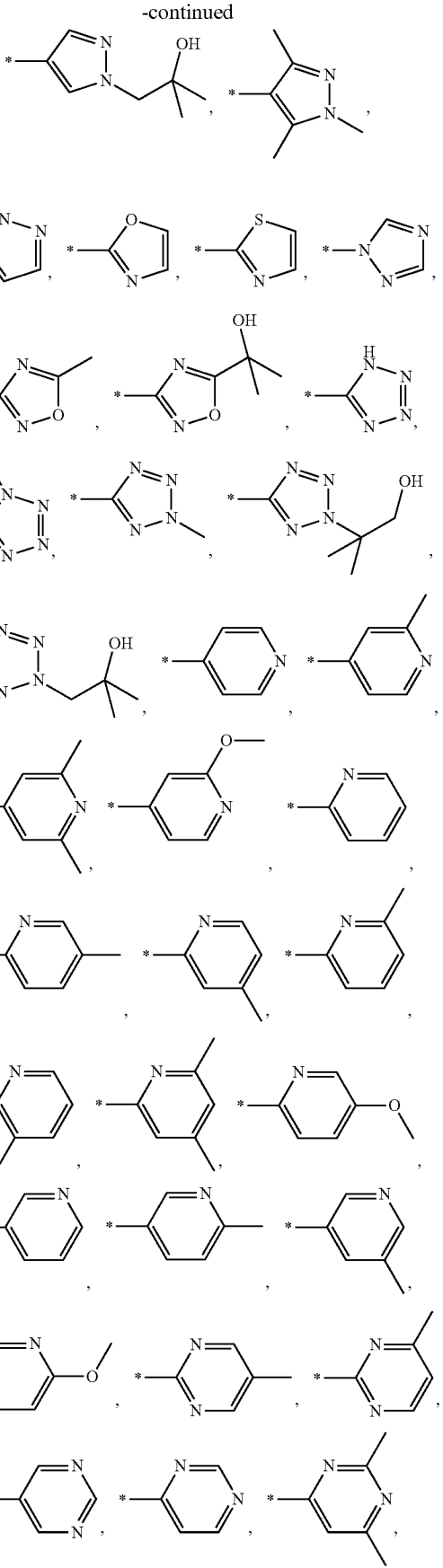

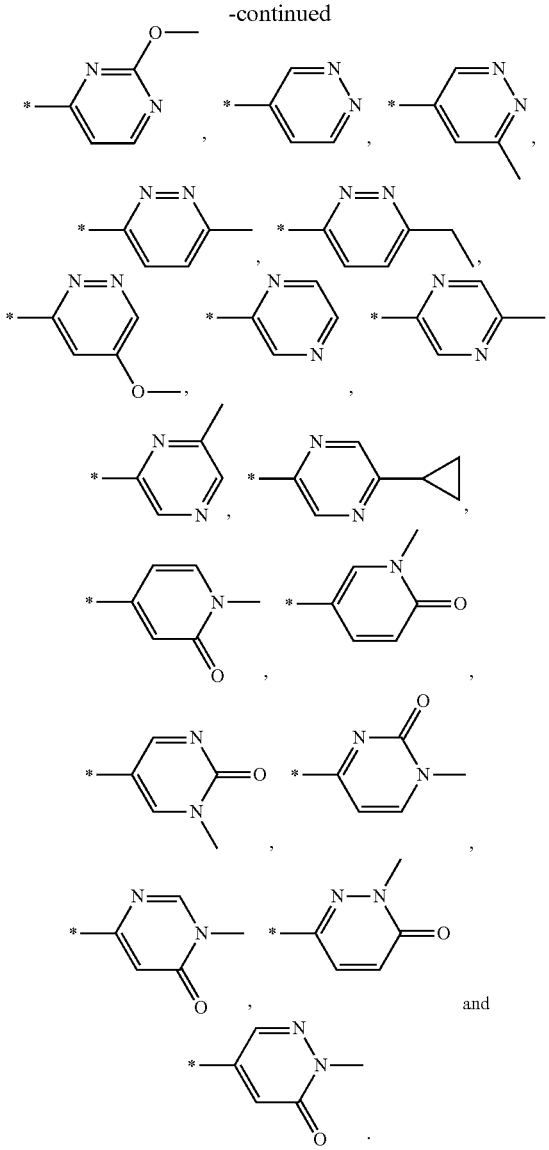

R$^4$

R$^4$-G1:

The group R$^4$ is preferably selected from the group R$^4$-G1 as defined hereinbefore.

R$^4$-G2:

In another embodiment the group R$^4$ is selected from the group R$^4$-G2 consisting of F, Cl, Br, CN, C$_{1-3}$-alkyl, C$_{3-4}$-cycloalkyl-, HO—O$_{1-3}$-alkyl, C$_{1-3}$-alkyl-O—O$_{1-3}$-alkyl, —NR$^N$H, C$_{1-4}$-alkyl-O—, C$_{3-5}$-cycloalkyl-O—, H$_3$C—S(=O)—, H$_3$C—S(=O)$_2$—, wherein any alkyl and cycloalkyl group is optionally substituted with 1 or more F atoms.

R$^4$-G3:

In another embodiment the group R$^4$ is selected from the group R$^4$-G3 consisting of F, Cl, CN, —CH$_3$, —CF$_3$, isopropyl, cyclopropyl, H$_3$C—O—CH$_2$—, H$_3$C—O—, and F$_3$C—O—.

R$^4$-G4:

In another embodiment the group R$^4$ is selected from the group R$^4$-G4 consisting of CH$_3$.

R$^5$

R$^5$-G1:

The group R$^5$ is preferably selected from the group R$^5$-G1 as defined hereinbefore.

R$^5$-G2:

In one embodiment the group R$^5$ is selected from the group R$^5$-G2 consisting of Cl, C$_{1-4}$-alkyl-, —CN, C$_{3-6}$-cycloalkyl-, heterocyclyl-C(=O)—, H$_2$N—C(=O)—, C$_{1-4}$-alkyl-NR$^N$—C(=O)—, C$_{3-6}$-cycloalkyl-NR$^N$—C(=O)—, heterocyclyl-NR$^N$—C(=O)—, heteroaryl-NR$^N$—C(=O)—, —NH$_2$, C$_{1-4}$-alkyl-NR$^N$—, C$_{1-4}$-alkyl-C(=O)NR$^N$—, C$_{3-6}$-cycloalkyl-C(=O)NR$^N$—, heterocyclyl-C(=O)NR$^N$—, heteroaryl-C(=O)NR$^N$—, C$_{1-4}$-alkyl-S(=O)$_2$NR$^N$—, —OH, C$_{1-4}$-alkyl-O—, C$_{1-4}$-alkyl-O—O$_{1-4}$-alkyl-O—, C$_{3-6}$-cycloalkyl-O—, heterocyclyl-O—, phenyl-O—, heteroaryl-O—, C$_{1-4}$-alkyl-S(=O)—, C$_{3-6}$-cycloalkyl-S(=O)—, C$_{1-4}$-alkyl-S(=O)$_2$—, C$_{3-6}$-cycloalkyl-S(=O)$_2$—, heterocyclyl, and heteroaryl, wherein any alkyl, cycloalkyl, and heterocyclyl group or subgroup within the groups mentioned is optionally substituted with 1 or more F atoms and optionally substituted with 1 or 2 groups independently selected from H$_3$C—, HO—, H$_3$C—O—, and —CN, wherein heterocyclyl is selected from a cyclobutyl group wherein 1 CH$_2$ group is replaced by —NR$^N$— or —O—;

a saturated or partially unsaturated C$_{5-6}$-cycloalkyl group wherein 1 CH$_2$ group is replaced by —C(=O)—, —NR$^N$—, —O—, —S(=O)— or —S(=O)$_2$— and/or 1 CH group by N;

a saturated or partially unsaturated C$_{5-6}$-cycloalkyl group wherein 1 CH$_2$ group is replaced by —NR$^N$—, or —O—, a second CH$_2$ group is replaced by —NR$^N$—, —C(=O)—, —S(=O)— or —S(=O)$_2$— and/or 1 CH group is replaced by N; and a saturated or partially unsaturated C$_{5-6}$-cycloalkyl group wherein 2 CH$_2$ group are replaced by —NR$^N$— or 1 CH$_2$ group by —NR$^N$— and the other by —O—, and a third CH$_2$ group is replaced by —C(=O)—, —S(=O)— or —S(=O)$_2$— and/or 1 CH group by N;

and wherein heteroaryl is selected from a tetrazolyl ring, a pyridin-2-onyl ring, a 5-membered heteroaromatic ring which contains 1, 2, or 3 heteroatoms independently of each other selected from =N—, —NH—, —O—, and —S—, and a 6-membered heteroaromatic ring which contains 1 or 2 =N— atoms, and wherein in heteroaromatic rings with one ore more NH groups each of them is replaced by NR$^N$, and each heteroaryl group is optionally substituted with 1 to 3 substituents independently selected from F, Cl, —CH$_3$, —CN, and —O—CH$_3$.

R$^5$-G3:

In another embodiment the group R$^5$ is selected from the group R$^5$-G3 consisting of C$_{1-4}$-alkyl-, —CN, C$_{3-6}$-cycloalkyl-, H$_2$N—C(=O)—, C$_{1-4}$-alkyl-NR$^N$—C(=O)—, C$_{1-4}$-alkyl-NR$^N$—, C$_{1-4}$-alkyl-C(=O)NR$^N$—, —NHC(=O)—O—C(CH$_3$)$_3$, C$_{1-4}$-alkyl-S(=O)$_2$NR$^N$—, —OH, C$_{1-4}$-alkyl-O—, C$_{1-4}$-alkyl-S(=O)—, C$_{1-4}$-alkyl-S(=O)$_2$—, heterocyclyl, and heteroaryl, wherein any alkyl, cycloalkyl, and heterocyclyl group or subgroup within the groups mentioned is optionally substituted with 1 to 3 F atoms and optionally substituted with 1 or 2 groups independently selected from H$_3$C—, HO—, H$_3$C—O—, and —CN, wherein heterocyclyl is selected from a cyclobutyl group wherein 1 CH$_2$ group is replaced by —NR$^N$— or —O—, a saturated or partially unsaturated C_{5-6}-cycloalkyl group wherein 1 CH_2 group is replaced by —C(=O)—, —NR^N—, —O—, —S(=O)— or —S(=O)_2— and/or 1 CH group by N;

a saturated or partially unsaturated C_{5-6}-cycloalkyl group wherein 1 CH_2 group is replaced by —NR^N— or —O—, a second CH_2 group is replaced by —NR^N—, —C(=O)—, —S(=O)— or —S(=O)_2— and/or 1 CH group is replaced by N; and a saturated or partially unsaturated C_{5-6}-cycloalkyl group wherein 2 CH_2 groups are replaced by —NR^N— or 1 CH_2 group by —NR^N— and the other by —O—, and a third CH_2 group is replaced by —C(=O)—, —S(=O)— or —S(=O)_2— and/or 1 CH group by N;

and wherein heteroaryl is selected from a pyridin-2-onyl ring, a 5-membered heteroaromatic ring which contains 1 or 2 heteroatoms independently of each other selected from =N—, —NH—, —O—, and —S—, and a 6-membered heteroaromatic ring which contains 1 or 2 =N— atoms, and wherein in heteroaromatic rings with one ore more NH groups each of them is replaced by NR^N, and each heteroaryl group is optionally substituted with 1 or 2 substituents independently selected from F, Cl, —CH_3, —CN, and —O—CH_3.

R^5-G4:

In another embodiment the group R^5 is selected from the group R^5-G4 consisting of —CH_3, —CN, 1-hydroxycyclopropyl, H_2N—C(=O)—, —C(=O)NHCH_3, —C(=O)N(CH_3)_2, —N(CH_3)_2, H_3C—C(=O)NH—, —NHC(=O)—O—C(CH_3)_3, H_3C—S(=O)_2NH—, H_3C—S(=O)_2N(CH_3)—, —OH, C_{1-3}-alkyl-O—, H_3C—S(=O)—, H_3C—S(=O)_2—, heterocyclyl, and heteroaryl, wherein heterocyclyl is selected from an azetidinyl, oxetanyl, a pyrrolidin-2-onyl, tetrahydrofuranyl, sulfolanyl, 1,1-dioxo-isothiazolidinyl, piperidinyl, tetrahydropyranyl, tetrahydrothiopyranyl, 1,1-dioxo-tetrahydrothiopyranyl ring, wherein each of these rings optionally is substituted with 1 CH_3 or 1 OH group and wherein an NH group, if present, optionally is replaced with NS(=O)_2—C_{1-3}-alkyl;

and wherein heteroaryl is selected from a 2-methoxy-pyridinyl, pyridin-2-onyl, imidazolyl, pyrazolyl, and oxazolyl ring, wherein in a heteroaryl group with a NH group this unit optionally is replaced by a N—CH_3 group.

R^5-G5:

According to another embodiment the group R^5 is selected from the group R^5-G5 consisting of —CH_3, —CN, —C(=O)NH_2, —C(=O)NHCH_3, —C(=O)N(CH_3)_2, —N(CH_3)_2, —NHC(=O)CH_3, —NHC(=O)—O—C(CH_3)_3, —NHS(=O)_2CH_3, —N(CH_3)S(=O)_2CH_3, —OH, —O—CH_3, —S(=O)CH_3, —S(=O)_2CH_3,

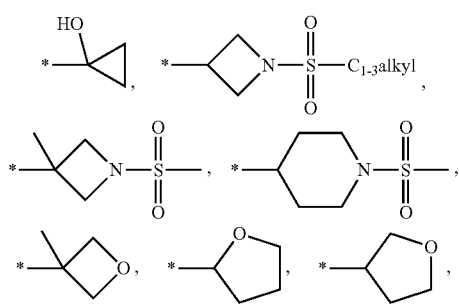

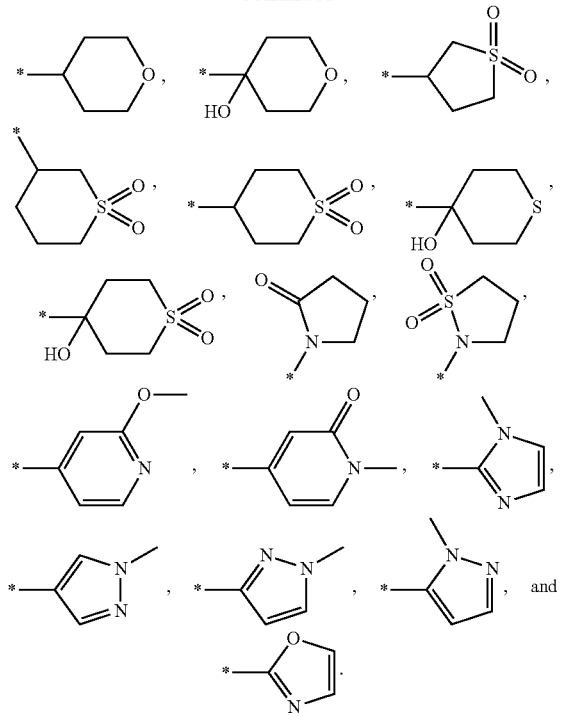

R^6

R^6-G1:

The group R^6 is preferably selected from the group R^6-G1 as defined hereinbefore.

R^6-G2:

In one embodiment the group R^6 is selected from the group R^6-G2 consisting of F, Cl, —CN, C_{1-3}-alkyl, cyclopropyl, HO—C_{1-3}-alkyl-, H_3C—O—C_{1-3}-alkyl-, H_3C—O—, —S(=O)CH_3, and —S(=O)_2—CH_3, wherein any alkyl and cycloalkyl group or sub-group within the groups mentioned is optionally substituted with 1 to 3 F atoms.

R^6-G3:

In another embodiment the group R^6 is selected from the group R^6-G3 consisting of F, Cl, —CN, —CH_3, —CH_2—CH_3, cyclopropyl, HO—C(CH_3)_2—, —CF_3, OCH_3, —OCF_3, —S(=O)CH_3, and —S(=O)_2—CH_3.

R^6-G4:

In another embodiment the group R^6 is selected from the group R^6-G4 consisting of F, —CH_3, —CH_2—CH_3, cyclopropyl, HO—C(CH_3)_2—, and —OCH_3.

R^6-G5:

In another embodiment the group R^6 is selected from the group R^6-G5 consisting of —CH_3 and —OCH_3.

R^N

R^N-G1:

The group R^N is preferably selected from the group R^N-G1 as defined hereinbefore.

R^N-G2:

In another embodiment the group R^N is selected from the group R^N-G2 consisting of H, C_{1-3}-alkyl, C_{1-3}-alkyl-C(=O)—, and C_{1-3}-alkyl-S(=O)_2—.

R^N-G3:

In another embodiment the group R^N is selected from the group R^N-G3 consisting of H, H_3O—, H_3C—C(=O)—, and C_{1-3}-alkyl-S(=O)_2—.

Examples of preferred subgeneric embodiments (E) according to the third and fourth aspect of the invention relating to processes for preparing indanyloxydihydrobenzofuranylacetic acids of formula IV.I are set forth in the following table, wherein $R^1$ of formula IV.I, IV, VI, $R^1$—X and $R^1$—X and sub-moieties $R^3$, $R^4$, $R^5$, $R^6$ and $R^N$ as components of $R^1$ are defined according to the definitions set forth hereinbefore:

| E | $R^1$— | $R^3$— | $R^4$— | $R^5$— | $R^6$— | $R^N$— |
|---|---|---|---|---|---|---|
| E-1 | $R^1$—G1 | $R^3$—G1 | $R^4$—G1 | $R^5$—G1 | $R^6$—G1 | $R^N$—G1 |
| E-2 | $R^1$—G2 | $R^3$—G2 | $R^4$—G2 | $R^5$—G2 | $R^6$—G2 | $R^N$—G2 |
| E-3 | $R^1$—G2a | $R^3$—G2 | $R^4$—G2 | $R^5$—G2 | $R^6$—G2 | $R^N$—G2 |
| E-4 | $R^1$—G2b | $R^3$—G2 | $R^4$—G2 | $R^5$—G2 | $R^6$—G2 | $R^N$—G2 |
| E-5 | $R^1$—G3 | $R^3$—G3 | $R^4$—G3 | $R^5$—G3 | $R^6$—G3 | $R^N$—G3 |
| E-6 | $R^1$—G4 | $R^3$—G3 | $R^4$—G3 | $R^5$—G3 | $R^6$—G3 | $R^N$—G3 |
| E-7 | $R^1$—G4a | $R^3$—G2 | $R^4$—G3 | $R^5$—G3 | $R^6$—G3 | $R^N$—G3 |
| E-8 | $R^1$—G4a | $R^3$—G3 | $R^4$—G3 | $R^5$—G3 | $R^6$—G3 | $R^N$—G3 |
| E-9 | $R^1$—G4a | $R^3$—G4 | $R^4$—G3 | $R^5$—G3 | $R^6$—G3 | $R^N$—G3 |
| E-10 | $R^1$—G4a | $R^3$—G4 | $R^4$—G3 | $R^5$—G4 | $R^6$—G4 | $R^N$—G3 |
| E-11 | $R^1$—G4a | $R^3$—G4 | $R^4$—G3 | $R^5$—G4 | $R^6$—G4 | $R^N$—G3 |
| E-12 | $R^1$—G4a | $R^3$—G4 | $R^4$—G3 | $R^5$—G5 | $R^6$—G4 | $R^N$—G3 |
| E-13 | $R^1$—G5 | $R^3$—G1 | — | $R^5$—G1 | $R^6$—G1 | $R^N$—G1 |
| E-14 | $R^1$—G5 | $R^3$—G2 | — | $R^5$—G2 | $R^6$—G2 | $R^N$—G2 |
| E-15 | $R^1$—G5 | $R^3$—G3 | — | $R^5$—G3 | $R^6$—G3 | $R^N$—G3 |
| E-16 | $R^1$—G5 | $R^3$—G3a | — | $R^5$—G3 | $R^6$—G3 | $R^N$—G3 |
| E-17 | $R^1$—G5 | $R^3$—G3a | — | $R^5$—G4 | $R^6$—G4 | $R^N$—G3 |
| E-18 | $R^1$—G5 | $R^3$—G4 | — | $R^5$—G3 | $R^6$—G3 | $R^N$—G3 |
| E-19 | $R^1$—G5 | $R^3$—G4 | — | $R^5$—G3 | $R^6$—G4 | $R^N$—G3 |
| E-20 | $R^1$—G5 | $R^3$—G4 | — | $R^5$—G4 | $R^6$—G4 | $R^N$—G3 |
| E-21 | $R^1$—G5 | $R^3$—G3 | — | $R^5$—G5 | $R^6$—G4 | $R^N$—G3 |
| E-22 | $R^1$—G5 | $R^3$—G4 | — | $R^5$—G5 | $R^6$—G4 | $R^N$—G3 |
| E-23 | $R^1$—G5 | $R^3$—G5 | — | — | — | — |
| E-24 | $R^1$—G5 | $R^3$—G6 | — | — | — | — |

Regarding the third and fourth aspect of the invention relating to processes for preparing indanyloxydihydrobenzofuranylacetic acids of formula IV.II, unless otherwise stated, group (Het)Ar of formula IV.II, $IV^{II}$, $IV^{III}$, $VI^{I}$, (Het)Ar—X2 and (Het)Ar—OH and submoieties $R^{1-II}$ and $R^{N-II}$ as components of (Het)Ar are defined as above and hereinafter. If residues, substituents, or groups occur several times in a compound, as for example $R^{N-II}$, they may have the same or different meanings. Some preferred meanings of individual groups and substituents of the compounds according to the invention will be given hereinafter. Any and each of these definitions may be combined with each other.

(Het)Ar:

(Het)Ar-G1:

The group (Het)Ar is preferably selected from the group (Het)Ar-G1 as defined hereinbefore.

(Het)Ar-G2:

According to one embodiment the group (Het)Ar is selected from the group (Het)Ar-G2 consisting of phenyl, naphthyl, and a mono- or bicyclic heteroaromatic group having 5 to 10 ring member atoms of which 2 to 9 ring members are carbon atoms and either one ring member is an unsubstituted or substituted heteroatom selected from N, NH, $NR^{N-II}$, O, S, S(=O) and $S(=O)_2$, or one ring member is N and a second ring member is selected from N, NH, $NR^{N-II}$, O, S, S(=O) and $S(=O)_2$, or two ring members are N and a third ring member is selected from N, NH, $NR^{N-II}$, O, S, S(=O) and $S(=O)_2$, wherein in naphthyl the ring not attached to the indanyl-O atom of formula IV.II may be partially saturated, wherein in bicyclic heteroaromatic groups the ring not attached to the indanyl-O atom of formula IV.II may be partially saturated, while at least one aromatic ring includes a heteroatom, and optionally one ring member in the partially or fully saturated bridge is replaced by N, NH, $NR^{N-II}$, O or S, or one ring member in the partially or fully saturated bridge is replaced by N, NH or $NR^{N-II}$ and a second ring member is replaced by NH, $NR^{N-II}$, O or S, wherein any of these groups is optionally and independently substituted with 1 to 5 $R^{1-II}$ groups;

(Het)Ar-G3:

According to one embodiment the group (Het)Ar is selected from the group (Het)Ar-G3 consisting of phenyl, naphthyl, pyridinyl, pyrimidinyl, pyrazinyl, pyridazinyl, quinolinyl, isoquinolinyl, quinazolinyl, imidazolyl, pyrazolyl, oxazolyl, isoxazolyl, thiazolyl, isothiazolyl, triazolyl, oxadiazolyl, thiadiazolyl, indolinyl, benzoimidazolyl, indazolyl, benzoxazolyl, benzoisoxazolyl and benzothiazolyl, wherein each of these groups is optionally substituted with 1 to 3 groups independently selected from $R^{1-II}$ and wherein independently a NH group optionally is replaced by a $NR^{N-II}$ group.

(Het)Ar-G4:

According to one embodiment the group (Het)Ar is selected from the group (Het)Ar-G4 consisting of phenyl, pyridinyl, pyrimidinyl, pyrazinyl, pyridazinyl, quinolinyl, isoquinolinyl, quinazolinyl, indolinyl, benzoimidazolyl, indazolyl, benzoxazolyl, benzoisoxazolyl and benzothiazolyl, wherein each of these groups is optionally substituted with 1 to 3 groups independently selected from $R^{1-II}$ and wherein independently a NH group optionally is replaced by a $NR^{N-II}$ group.

(Het)Ar-G5:

In another embodiment the group (Het)Ar is selected from the group (Het)Ar-G5 consisting of

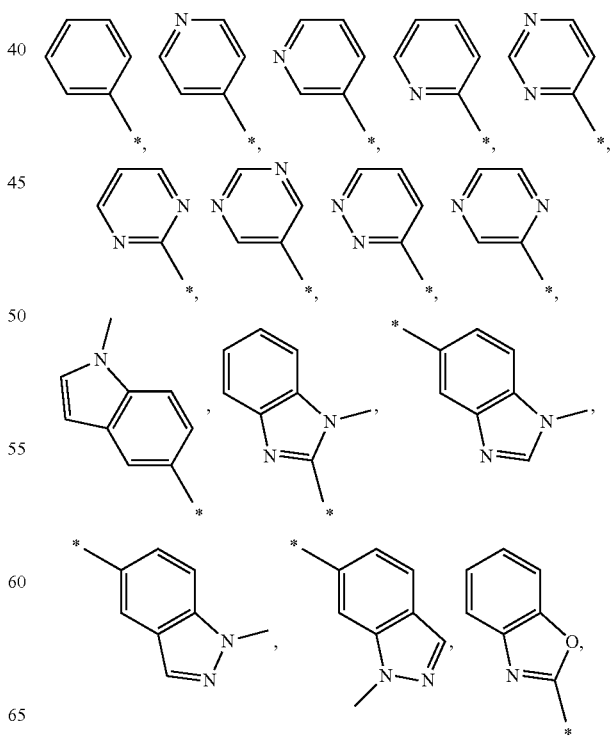

-continued

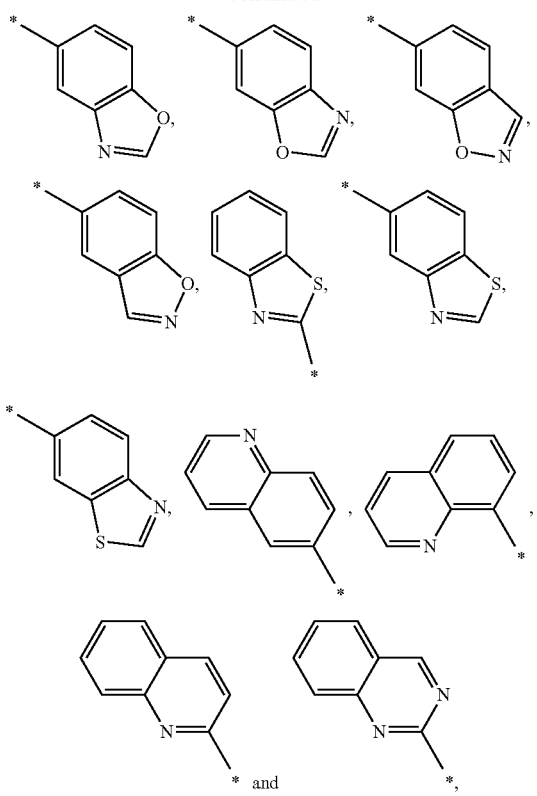

wherein each of these groups is optionally substituted with 1 to 3 substituents independently selected from $R^{1-II}$.

(Het)Ar-G5a:

In another embodiment the group (Het)Ar is selected from the group (Het)Ar-G5a consisting of

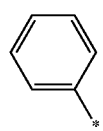

which is optionally substituted with 1 to 3 substituents independently selected from $R^{1-II}$.

(Het)Ar-G5b:

In another embodiment the group (Het)Ar is selected from the group (Het)Ar-G5b consisting of

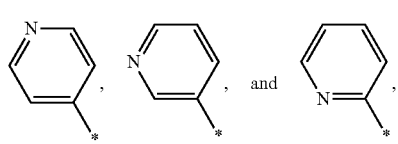

wherein each of these groups is optionally substituted with 1 or 2 substituents independently selected from $R^{1-II}$.

(Het)Ar-G5c:

In another embodiment the group (Het)Ar is selected from the group (Het)Ar-G5c consisting of

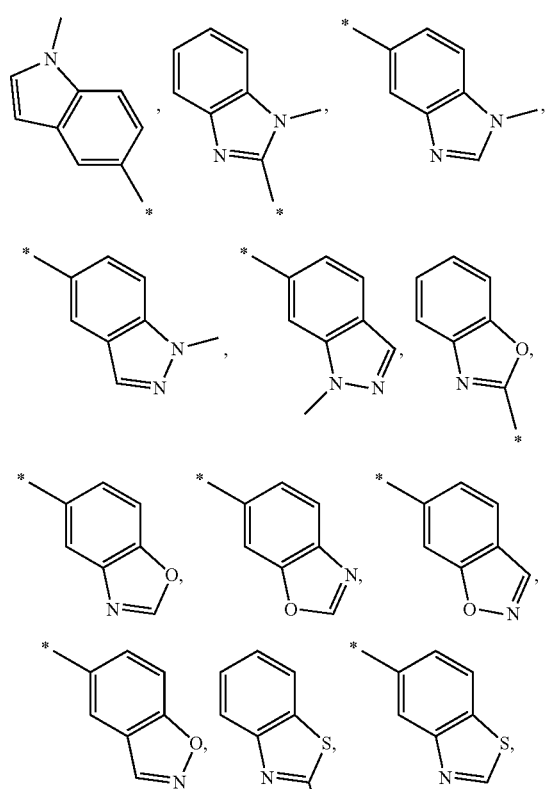

wherein each of these groups is optionally substituted with 1 to 3 substituents independently selected from $R^{1-II}$.

(Het)Ar-G6:

In another embodiment the group (Het)Ar is selected from the group (Het)Ar-G6 consisting of

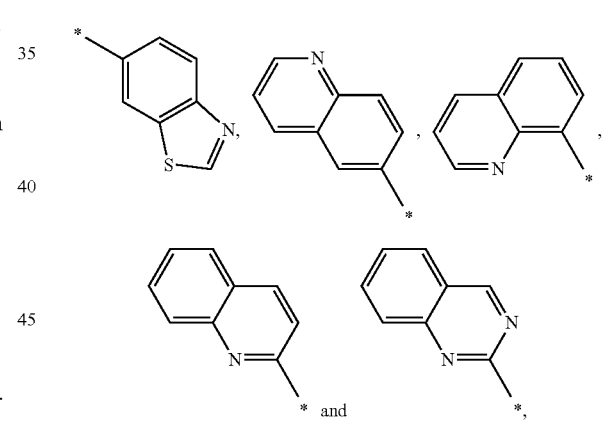

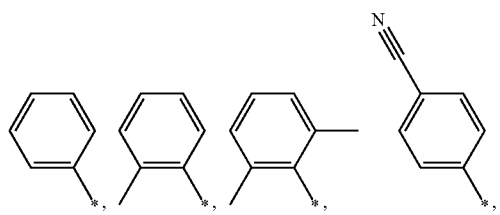

-continued
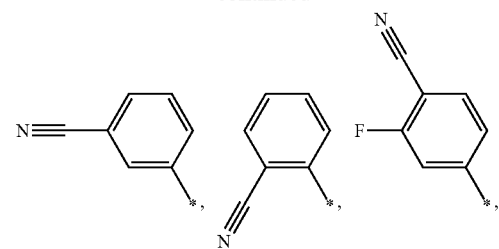
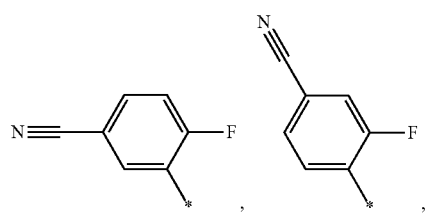
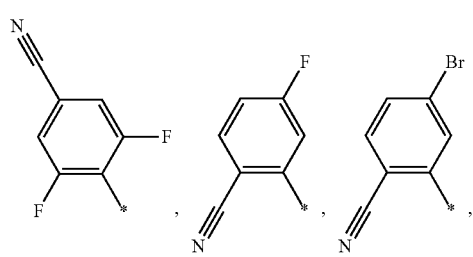
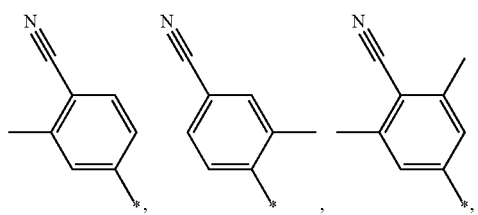
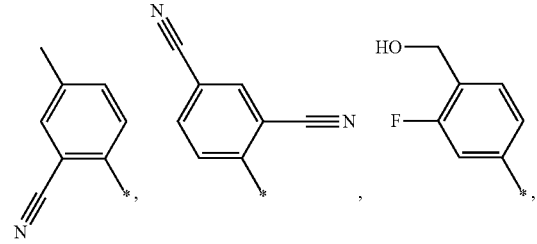
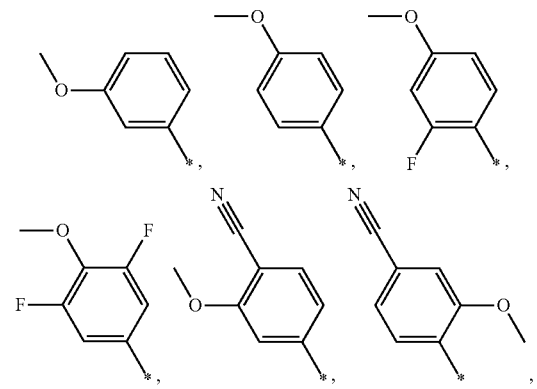
-continued
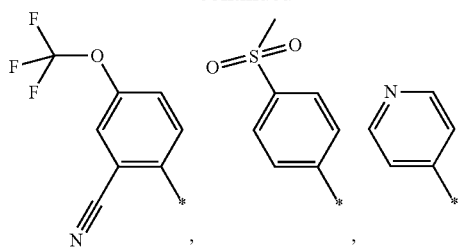
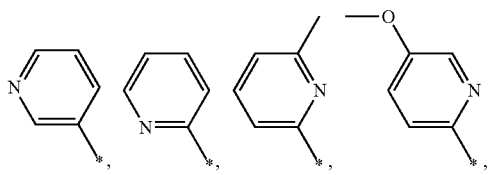
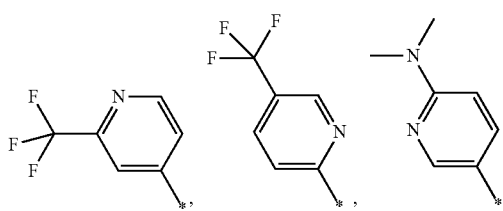
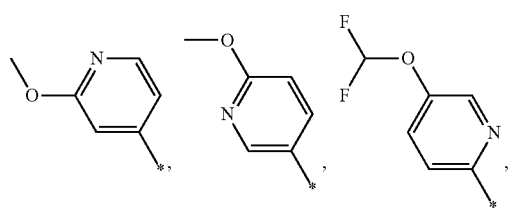
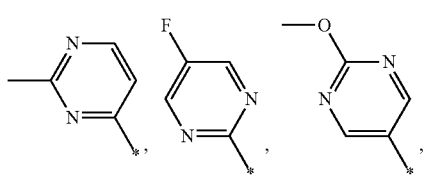
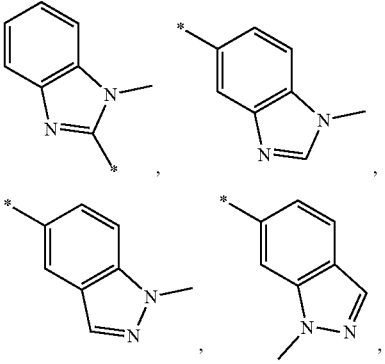

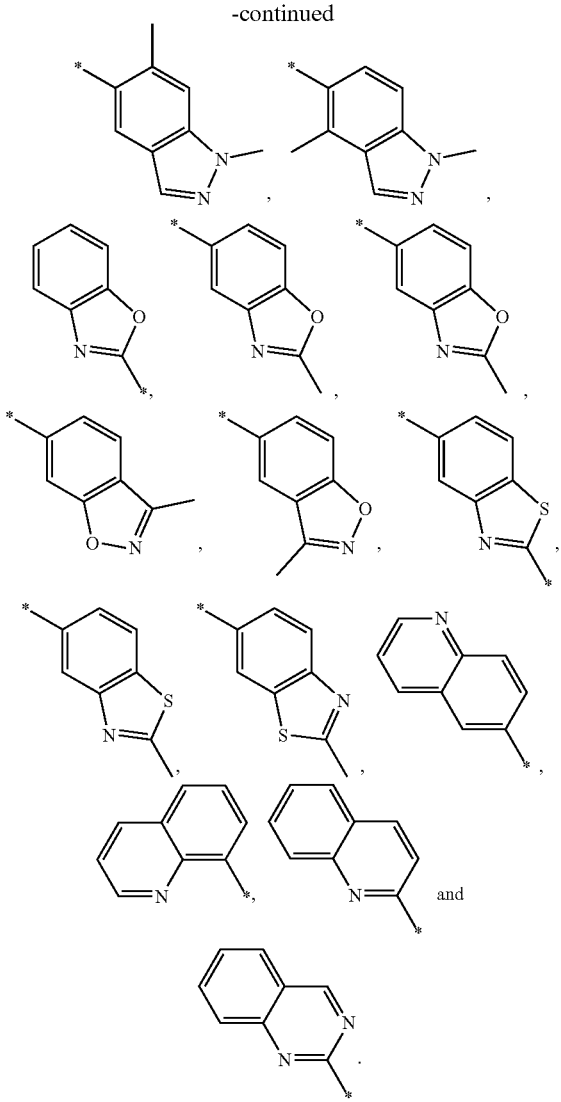

$R^{1-II}$:
$R^{1-II}$-G1:

The group $R^{1-II}$ is preferably selected from the group $R^{1-II}$-G1 as defined hereinbefore.

$R^{1-II}$-G2:

In another embodiment the group $R^{1-II}$ is selected from the group $R^{1-II}$-G2 consisting of F, Cl, Br, $C_{1-4}$-alkyl, $C_{2-4}$-alkinyl, HO—$C_{1-4}$-alkyl, $C_{1-4}$-alkyl-O—$C_{1-4}$-alkyl, CN, $NH_2$, $C_{1-4}$-alkyl-NH—, $(C_{1-4}$-alkyl$)_2$N—, OH, $C_{1-4}$-alkyl-O—, $C_{1-4}$-alkyl-S(=O)—, $C_{1-4}$-alkyl-S(=O)$_2$—, $C_{3-6}$-cycloalkyl and $C_{3-6}$-cycloalkyl-O—, wherein any alkyl and cycloalkyl group or submoiety is optionally substituted with 1 to 3 F atoms.

$R^{1-II}$-G3:

In another embodiment the group $R^{1-II}$ is selected from the group $R^{1-II}$-G3 consisting of F, Cl, Br, $C_{1-4}$-alkyl, $F_2HC$—, $F_3C$—, HO—$C_{1-4}$-alkyl, $H_3C$—O—$C_{1-4}$-alkyl, $H_3C$—NH—, $(H_3C)_2N$—, CN, OH, $C_{1-4}$-alkyl-O—, $F_2HC$—O—, $F_3C$—O—, $H_3C$—S(=O)—, $H_3C$—S(=O)$_2$—, $C_{3-5}$-cycloalkyl and $C_{5-6}$-cycloalkyl-O—.

$R^{1-II}$-G4:

In another embodiment the group $R^{1-II}$ is selected from the group $R^{1-II}$-G4 consisting of F, Cl, Br, $C_{1-3}$-alkyl, $F_2HC$—, $F_3C$—, HO—$CH_2$—, $H_3C$—O—$CH_2$—, $H_3C$—NH—, $(H_3C)_2N$—, CN, OH, $C_{1-3}$-alkyl-O—, $F_2HC$—O—, $F_3C$—O—, $H_3C$—S(=O)$_2$— and cyclopropyl.

$R^{1-II}$-G5:

In another embodiment the group $R^{1-II}$ is selected from the group $R^{1-II}$-G5 consisting of F, $H_3C$—, $F_3C$—, NC—, HO—$H_2C$—, $(H_3C)_2N$—, $H_3C$—O—, $HF_2C$—O—, $F_3C$—O— and $H_3C$—S(=O)$_2$—.

$R^{1-II}$-G6:

In another embodiment the group $R^{1-II}$ is selected from the group $R^{1-II}$-G6 consisting of F, $H_3C$—, $F_3C$—, NC—, $H_3C$—O—, $HF_2C$—O— and $F_3C$—O—.

$R^{1-II}$:

$R^{N-II}$-G1:

The group $R^{N-II}$ is preferably selected from the group $R^{N-II}$-G1 as defined hereinbefore.

$R^{N-II}$-G2:

In another embodiment the group $R^{N-II}$ is selected from the group $R^{N-II}$-G2 consisting of $C_{1-3}$-alkyl, HO—$C_{1-4}$-alkyl, $C_{1-3}$-alkyl-O—$C_{1-4}$-alkyl, $C_{1-3}$-alkyl-C(=O)—, $C_{1-3}$-alkyl-S(=O)$_2$—, and $C_{4-6}$-cycloalkyl-, wherein any alkyl group or submoiety is optionally substituted with 1 to 3 F atoms.

$R^{N-II}$-G3:

In another embodiment the group $R^{N-II}$ is selected from the group $R^{N-II}$-G3 consisting of $C_{1-3}$-alkyl, HO—$C_{1-4}$-alkyl, $H_3C$—O—$C_{1-4}$-alkyl, $H_3C$—C(=O)—, and $H_3C$—S(=O)$_2$—.

$R^{N-II}$-G4:

In another embodiment the group $R^{N-II}$ is selected from the group $R^{N-II}$-G4 consisting of $C_{1-3}$-alkyl, HO—$C_{1-4}$-alkyl, and $H_3C$—C(=O)—.

$R^{N-II}$-G5:

In another embodiment the group $R^{N-II}$ is selected from the group $R^{N-II}$-G5 consisting of $C_{1-3}$-alkyl, preferably methyl.

Examples of preferred subgeneric embodiments ($E^I$) according to the third and fourth aspect of the invention relating to processes for preparing indanyloxydihydrobenzofuranylacetic acids of formula IV.II are set forth in the following table, wherein (Het)Ar of formula IV.II, $IV^{II}$, $IV^{III}$, $VI^I$, (Het)Ar—X2 and (Het)Ar—OH and submoieties $R^{1-II}$ and $R^{N-II}$ as components of (Het)Ar are defined according to the definitions set forth hereinbefore:

| Embodiment | (Het)Ar- | $R^{1-II}$- | $R^{N-II}$- |
|---|---|---|---|
| $E^I$-1 | (Het)Ar-G1 | $R^{1-II}$-G1 | $R^{N-II}$-G1 |
| $E^I$-2 | (Het)Ar-G2 | $R^{1-II}$-G3 | $R^{N-II}$-G3 |
| $E^I$-3 | (Het)Ar-G2 | $R^{1-II}$-G4 | $R^{N-II}$-G4 |
| $E^I$-4 | (Het)Ar-G2 | $R^{1-II}$-G5 | $R^{N-II}$-G5 |
| $E^I$-5 | (Het)Ar-G3 | $R^{1-II}$-G1 | $R^{N-II}$-G2 |
| $E^I$-6 | (Het)Ar-G3 | $R^{1-II}$-G3 | $R^{N-II}$-G3 |
| $E^I$-7 | (Het)Ar-G3 | $R^{1-II}$-G4 | $R^{N-II}$-G4 |
| $E^I$-8 | (Het)Ar-G3 | $R^{1-II}$-G5 | $R^{N-II}$-G5 |
| $E^I$-9 | (Het)Ar-G4 | $R^{1-II}$-G1 | $R^{N-II}$-G2 |
| $E^I$-10 | (Het)Ar-G4 | $R^{1-II}$-G2 | $R^{N-II}$-G3 |
| $E^I$-11 | (Het)Ar-G4 | $R^{1-II}$-G3 | $R^{N-II}$-G3 |
| $E^I$-12 | (Het)Ar-G4 | $R^{1-II}$-G4 | $R^{N-II}$-G4 |
| $E^I$-13 | (Het)Ar-G4 | $R^{1-II}$-G5 | $R^{N-II}$-G5 |
| $E^I$-14 | (Het)Ar-G5 | $R^{1-II}$-G1 | — |
| $E^I$-15 | (Het)Ar-G5 | $R^{1-II}$-G2 | — |
| $E^I$-16 | (Het)Ar-G5 | $R^{1-II}$-G3 | — |
| $E^I$-17 | (Het)Ar-G5 | $R^{1-II}$-G4 | — |
| $E^I$-18 | (Het)Ar-G5 | $R^{1-II}$-G5 | — |
| $E^I$-19 | (Het)Ar-G5 | $R^{1-II}$-G6 | — |
| $E^I$-20 | (Het)Ar-G6 | — | — |

Regarding the third and fourth aspect of the invention relating to processes for preparing indanyloxydihydrobenzofuranylacetic acids of formula IV.III, unless otherwise stated, group $R^{1-III}$ of formula IV.III, $IV^{IV}$, $IV^V$, $VI^{II}$, and $R^{1-III}$—

CH₂—X3 and submoieties R$^{2\text{-}III}$ and R$^{N\text{-}III}$ as components of R$^{1\text{-}III}$ are defined as above and hereinafter. If residues, substituents, or groups occur several times in a compound, as for example R$^{N\text{-}III}$, they may have the same or different meanings. Some preferred meanings of individual groups and substituents of the compounds according to the invention will be given hereinafter. Any and each of these definitions may be combined with each other.

R$^{1\text{-}III}$:

R$^{1\text{-}III}$-G1:

The group R$^{1\text{-}III}$ is preferably selected from the group R$^{1\text{-}III}$-G1 as defined hereinbefore.

R$^{1\text{-}III}$-G2:

According to one embodiment the group R$^{1\text{-}III}$ is selected from the group R$^{1\text{-}III}$-G2 consisting of a monocyclic or bicyclic group having 5 to 10 ring member atoms of which 4 to 9 ring members are C atoms and 1 to 3 ring members are heteroatoms selected from N and NR$^{N\text{-}III}$, or 1 or 2 ring members are heteroatoms selected from N and NR$^{N\text{-}III}$ and 1 ring member is O or S, wherein the ring member atom attached to the —CH₂— group in formula I is a N atom, wherein 1 CH₂ ring member attached to a ring member N atom is optionally replaced by a —C(=O)— group, wherein the monocyclic or bicyclic group is saturated or partially unsaturated, with the proviso that in bicyclic groups the ring attached to the —CH₂— group in formula I must not be aromatic, and wherein the bicyclic group may be a fused, bridged or spiro ring system;

wherein any of these groups is optionally and independently substituted with 1, 2, or 3 R$^{2\text{-}III}$ groups;

R$^{1\text{-}III}$-G3:

According to one embodiment the group R$^{1\text{-}III}$ is selected from the group R$^{1\text{-}III}$-G3 consisting of

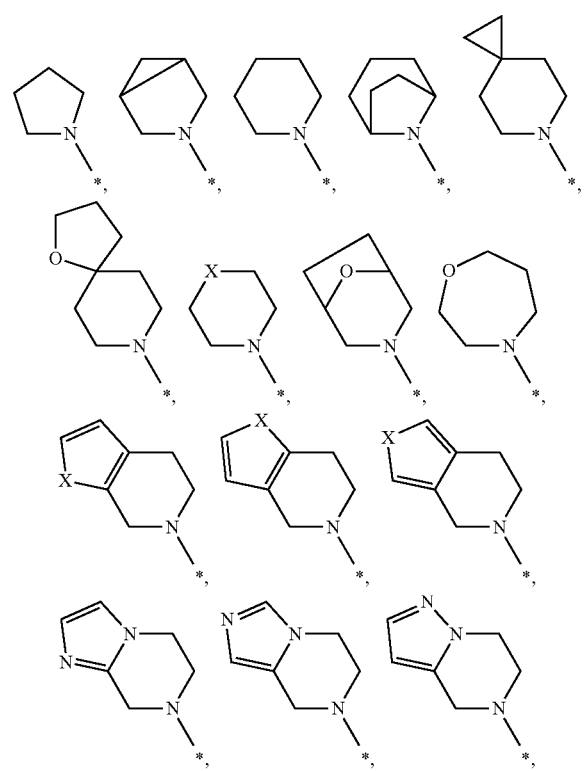

wherein X denotes NR$^{N\text{-}III}$, O, or S, and wherein in any group 1 ring member CH₂ group adjacent to a ring member N atom is optionally replaced by a C(=O) group, and wherein any group is optionally substituted with 1 to 3 groups independently selected from R$^{2\text{-}III}$.

R$^{1\text{-}III}$-G3a:

According to one embodiment the group R$^{1\text{-}III}$ is selected from the group R$^{1\text{-}III}$-G3a consisting of wherein X denotes NR$^{N\text{-}III}$, O, or S, and wherein in any group 1 ring member CH₂ group adjacent to a ring member N atom is optionally replaced by C(=O), and wherein any group is optionally substituted with 1, 2, or 3 groups independently selected from $R^{2-III}$.

$R^{1-III}$-G3b:

According to one embodiment the group $R^{1-III}$ is selected from the group $R^{1-III}$-G3b consisting of

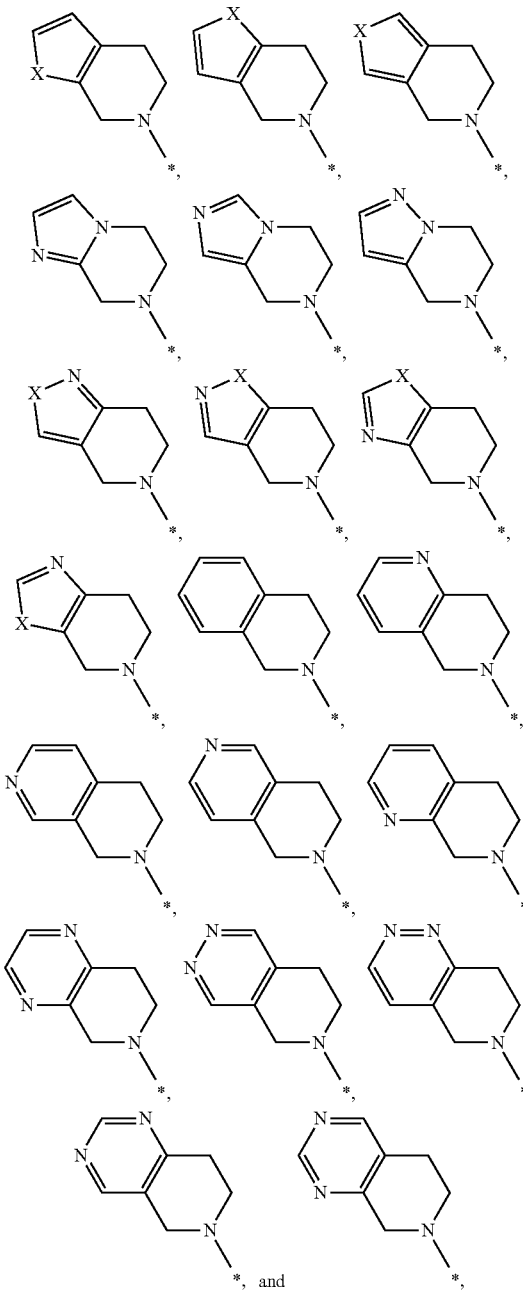

wherein X denotes $NR^{N-III}$, O, or S, and
wherein in any group 1 ring member $CH_2$ group adjacent to a ring member N atom is optionally replaced by C(=O), and wherein any group is optionally substituted with 1, 2, or 3 groups independently selected from $R^{2-III}$.

$R^{1-III}$-G4:

In another embodiment the group $R^{1-III}$ is selected from the group $R^{1-III}$-G4 consisting of a pyrrolidin-1-yl, 3-aza-bicyclo[3.1.0]hexan-3-yl, 8-aza-bicyclo[3.2.1]octan-8-yl, 6-aza-spiro[2.5]octan-6-yl, 1-oxa-8-aza-spiro[4.5]decan-8-yl, 8-oxa-3-aza-bicyclo[3.2.1]octan-3-yl, thiomorpholin-4-yl, and [1,4]oxazepan-4-yl ring;

a piperidin-1-yl ring, optionally substituted with 1 or 2 groups independently selected from F, $H_3C$—, HO—$H_2C$—, HO—, and $H_3C$—O—;

a piperazin-1-yl group, wherein the ring member N not attached to the —$CH_2$— group in formula IV.III is substituted with $R^{N-III}$, and wherein 1 $CH_2$ ring member is optionally replaced by a —C(=O)— group;

a morpholin-4-yl ring, optionally substituted with 1 or 2 $H_3C$— groups; and a 4,5,6,7-tetrahydrothieno[2,3-c]pyridin-6-yl, 5,6,7,8-tetrahydro-1H-imidazo[1,2-a]pyrazin-7-yl, 4,5,6,7-tetrahydropyrazolo[1,5-a]pyrazin-5-yl, 4,5,6,7-tetrahydro-2H-pyrazolo[4,3-c]pyridin-5-yl, 4,5,6,7-tetrahydro-oxazolo[4,5-c]pyridin-5-yl, 4,5,6,7-tetrahydro-isoxazolo[4,3-c]pyridin-5-yl, 4,5,6,7-tetrahydrothiazolo[5,4-c]pyridin-5-yl, 1,2,3,4-tetrahydro-isoquinolin-2-yl, and 5,6,7,8-tetrahydro-[1,6]naphthyridin-6-yl ring, wherein each ring having an NH group is substituted with $R^{N-III}$ at this N, and each ring is optionally substituted with 1 $H_3C$— group.

$R^{1-III}$-G5:

In another embodiment the group $R^{1-III}$ is selected from the group $R^{1-III}$-G5 consisting of

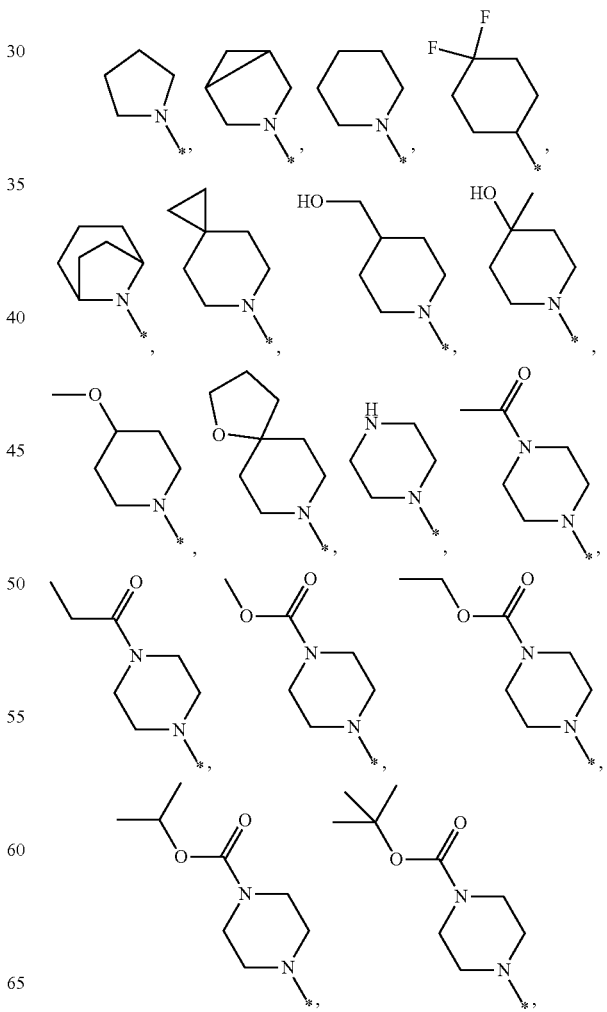

-continued

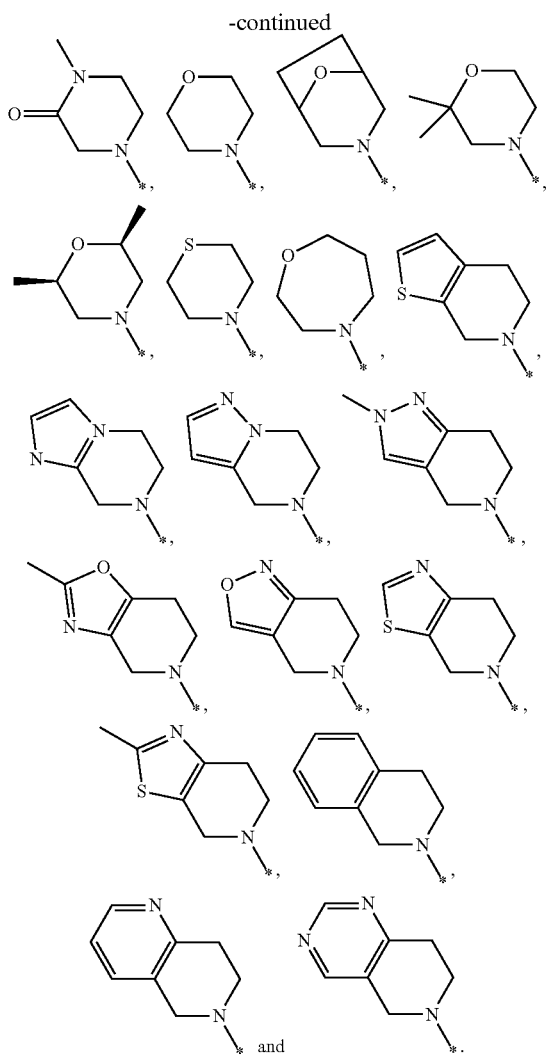

$R^{2\text{-}III}$:

$R^{2\text{-}III}$-G1:

The group $R^{2\text{-}III}$ is preferably selected from the group $R^{2\text{-}III}$-G1 as defined hereinbefore.

$R^{2\text{-}III}$-G2:

In another embodiment the group $R^{2\text{-}III}$ is selected from the group $R^{2\text{-}III}$-G2 consisting of F, Cl, $C_{1\text{-}3}$-alkyl, NC—, HO—$C_{1\text{-}3}$-alkyl, $C_{1\text{-}3}$-alkyl-O—$C_{1\text{-}3}$-alkyl, HO—, $C_{1\text{-}3}$-alkyl-O—, $H_3C$—S(=O)—, $H_3C$—S(=O)$_2$—, $C_{3\text{-}6}$-cycloalkyl-, and $C_{3\text{-}6}$-cycloalkyl-O—, wherein any alkyl and cycloalkyl group or submoiety is optionally substituted with 1 to 3 F atoms.

$R^{2\text{-}III}$-G3:

In another embodiment the group $R^{2\text{-}III}$ is selected from the group $R^{2\text{-}III}$-G3 consisting of F, Cl, $C_{1\text{-}3}$-alkyl, $F_3C$—, NC—, HO—$C_{1\text{-}3}$-alkyl, $H_3C$—O—$C_{1\text{-}3}$-alkyl, HO—, $C_{1\text{-}3}$-alkyl-O, $F_2HC$—O—, $F_3C$—O—, $H_3C$—S(=O)$_2$—, $C_{3\text{-}6}$-cycloalkyl-, and $C_{3\text{-}6}$-cycloalkyl-O—.

$R^{2\text{-}III}$-G4:

In another embodiment the group $R^{2\text{-}III}$ is selected from the group $R^{2\text{-}III}$-G4 consisting of F, $C_{1\text{-}3}$-alkyl, $F_3C$—, HO—$CH_2$—, $H_3C$—O—$CH_2$—, NC—, HO—, $C_{1\text{-}3}$-alkyl-O—, and $H_3C$—S(=O)$_2$—.

$R^{2\text{-}III}$-G5:

In another embodiment the group $R^{2\text{-}III}$ is selected from the group $R^{2\text{-}III}$-G5 consisting of F, $H_3C$—, HO—$H_2C$—, HO—, and $H_3C$—O—.

$R^{N\text{-}III}$:

$R^{N\text{-}III}$-G1:

The group $R^{N\text{-}III}$ is preferably selected from the group $R^{N\text{-}III}$-G1 as defined hereinbefore.

$R^{N\text{-}III}$-G2:

In another embodiment the group $R^{N\text{-}III}$ is selected from the group $R^{N\text{-}III}$-G2 consisting of H, $H_3C$—, $H_3C$—C(=O)—, $H_3C$—$H_2C$—C(=O)—, and $C_{1\text{-}4}$-alkyl-O—C(=O)—.

Examples of preferred subgeneric embodiments ($E^{II}$) according to the third and fourth aspect of the invention relating to processes for preparing indanyloxydihydrobenzofuranylacetic acids of formula IV.III are set forth in the following table, wherein $R^{1\text{-}III}$ of formula IV.III, $IV^{IV}$, $IV^{V}$, $VI^{II}$, and $R^{1\text{-}III}$—$CH_2$—X3 and sub-moieties $R^{2\text{-}III}$ and $R^{N\text{-}III}$ as components of $R^{1\text{-}III}$ are defined according to the definitions set forth hereinbefore:

| Embodiment | $R^{1\text{-}III}$- | $R^{2\text{-}III}$- | $R^{N\text{-}III}$- |
| --- | --- | --- | --- |
| $E^{II}$-1 | $R^{1\text{-}III}$-G1 | $R^{2\text{-}III}$-G1 | $R^{N\text{-}III}$-G1 |
| $E^{II}$-2 | $R^{1\text{-}III}$-G2 | $R^{2\text{-}III}$-G1 | $R^{N\text{-}III}$-G1 |
| $E^{II}$-3 | $R^{1\text{-}III}$-G3 | $R^{2\text{-}III}$-G1 | $R^{N\text{-}III}$-G1 |
| $E^{II}$-4 | $R^{1\text{-}III}$-G3 | $R^{2\text{-}III}$-G2 | $R^{N\text{-}III}$-G1 |
| $E^{II}$-5 | $R^{1\text{-}III}$-G3 | $R^{2\text{-}III}$-G2 | $R^{N\text{-}III}$-G2 |
| $E^{II}$-6 | $R^{1\text{-}III}$-G3 | $R^{2\text{-}III}$-G3 | $R^{N\text{-}III}$-G2 |
| $E^{II}$-7 | $R^{1\text{-}III}$-G3 | $R^{2\text{-}III}$-G4 | $R^{N\text{-}III}$-G2 |
| $E^{II}$-8 | $R^{1\text{-}III}$-G3 | $R^{2\text{-}III}$-G5 | $R^{N\text{-}III}$-G2 |
| $E^{II}$-9 | $R^{1\text{-}III}$-G4 | — | $R^{N\text{-}III}$-G2 |
| $E^{II}$-10 | $R^{1\text{-}III}$-G5 | — | — |

As mentioned under the first aspect of the invention the compounds of formula I are valuable intermediates for preparing indanyloxydihydrobenzofuranylacetic acid GPR40 agonists. Compounds of formula I wherein $R^a$ denotes a hydrogen atom may be transformed into salts with bases using conventional methods, such as the lithium, sodium or potassium salt, or salts to be formed with organic bases such as triethylamine, tert-butylamine, imidazole, morpholine, N-methyl-morpholine or piperazine. Especially the salts formed with organic bases may be easily crystallized. Salt formation may be carried out by addition of the corresponding base to a solution of a compound of formula I in a suitable (inert) solvent, optionally with heating.

The process for preparing the compounds of formula I according to the second aspect of the invention comprising the following condensation

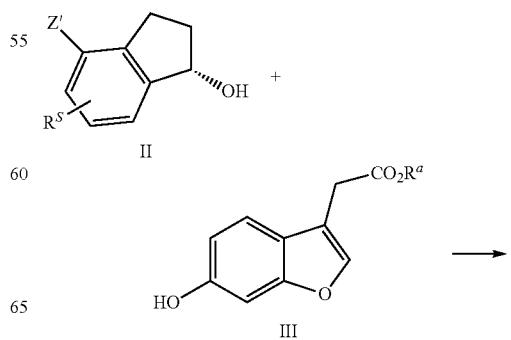

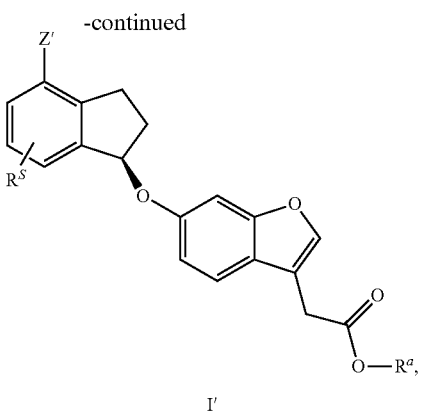

I' wherein $R^S$ denotes F or $CF_3$ and $R^a$ denotes $C_{1-4}$-alkyl, preferably —$CH_3$, is preferably carried out using processes known in the art, such as the Mitsunobu reaction. The reaction is usually conducted with a phosphine and an azodicarboxylic ester or amide in tetrahydrofuran, methyltetrahydrofuran, 1,4-dioxane, diethyl ether, toluene, ethyl acetate, acetonitrile, benzene, dichloromethane, or mixtures thereof, at −30 to 100° C. Phosphines often used are triphenylphosphine and tributylphosphine which are commonly combined with dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethylamide), azodicarboxylic acid dipiperidide, or azodicarboxylic acid dimorpholide.

The optional subsequent saponification in order to obtain compounds wherein $R^a$ denotes H is carried out using an acid or a base, preferably a base, according to a conventional method.

As the acid, for example, mineral acids such as hydrochloric acid, sulfuric acid and the like may be used. As the base, for example, alkali metal hydroxides such as lithium hydroxide, sodium hydroxide, potassium hydroxide and the like, alkaline earth metal hydroxides such as barium hydroxide and the like, alkali metal carbonates such as sodium carbonate, potassium carbonate and the like, or organic bases such as triethylamine, imidazole, formamidine and the like may be used. The amount of the acid or base to be used is generally about 0.1 to about 10 mol, preferably about 0.5 to about 6 mol per 1 mol of the ester to be hydrolysed. The hydrolysis reaction is carried out without additional solvent, or using a solvent inert to the reaction. Suitable solvents may be selected from alcohols such as methanol, ethanol, propanol and the like, aromatic hydrocarbons such as benzene, toluene and the like, saturated hydrocarbons such as cyclohexane, hexane and the like, ethers such as tetrahydrofuran, 1,4-dioxane, 1,2-dimethoxyethane and the like, amides such as N,N-dimethylformamide, N,N-dimethylacetamide and the like, halogenated hydrocarbons such as dichloromethane, chloroform, carbon tetrachloride, 1,2-dichloroethane and the like, nitriles such as acetonitrile, propionitrile and the like, ketones such as acetone, ethyl methyl ketone and the like, sulfoxides such as dimethyl sulfoxide and the like, water or a mixture of solvents specified hereinbefore.

The reaction temperature is generally −10 to 200° C., preferably 0 to 120° C., more preferred 10 to 60° C.

Starting compound II may be obtained in analogy to processes described in WO2012072691, e.g. starting from the corresponding indanone, which, in turn, may be prepared from phenylpropionic acid derivative 1 (Scheme 1); $R^S$ and $Z'$ have the meanings as defined hereinbefore and hereinafter and X is a leaving group or leaving group precursor. For the intramolecular acylation (Friedel-Crafts acylation), a considerable number of approaches has been reported. The reaction may be performed starting with a carboxylic acid, carboxylic ester, carboxylic anhydride, carboxylic chloride or fluoride, or a nitrile using a Lewis acid as catalyst. The following Lewis acids are some of the more often used ones: hydrobromic acid, hydroiodic acid, hydrochloric acid, sulfuric acid, phosphoric acid, $P_4O_{10}$, trifluoroacetic acid, methanesulfonic acid, toluenesulfonic acid, trifluoromethanesulfonic acid, $ClSO_3H$, $Sc(OSO_2CF_3)_3$, $Tb(OSO_2CF_3)_3$, $SnCl_4$, $FeCl_3$, $AlBr_3$, $AlCl_3$, $SbCl_5$, $BCl_3$, $BF_3$, $ZnCl_2$, montmorillonites, $POCl_3$, and $PCl_5$. The reaction may be conducted, e.g., in dichloromethane, 1,2-dichloroethane, nitrobenzene, chlorobenzene, carbon disulfide, mixtures thereof, or without an additional solvent in an excess of the Lewis acid, at 0 to 180° C. Carboxylic acids are preferably reacted in polyphosphoric acid or trifluoroacetic acid at 0 to 120° C., while carboxylic chlorides are preferably reacted with $AlCl_3$ in dichloromethane or 1,2-dichloroethane at 0 to 80° C.

The subsequent reduction of the carbonyl group in compound 2 providing the alcohol II in enantiomerically enriched or pure form may be accomplished using hydrogen or a hydrogen source, such as formate or silane, and a transition metal catalyst derived from, e.g., Ir, Rh, Ru or Fe and a chiral auxiliary. For instance, a ruthenium complex, such as chloro{[(1S,2S)-(−)-2-amino-1,2-diphenylethyl](4-toluenesulfonyl)-amido}-(mesitylene)ruthenium(II), may deliver the hydroxy compound II with high enantiomeric excess using, e.g., formic acid in the presence of a base, e.g., triethylamine, in dichloromethane, at −20 to 60° C. Alternatively, boranes combined with an enantiomerically pure [1,3,2]oxazaborol may be used as reducing agent (Corey-Bakshi-Shibata reaction or Corey-Itsuno reaction). Typical reaction conditions for this approach employ borane (complexed with, e.g., dimethyl sulfide) and (R)— or (S)-3,3-diphenyl-1-methyltetrahydro-1H,3H-pyrrolo[1,2-c][1,3,2]oxazaborol in, e.g., dichloromethane, toluene, methanol, tetrahydrofuran, or mixtures thereof, at 0 to 60° C.

Scheme 1

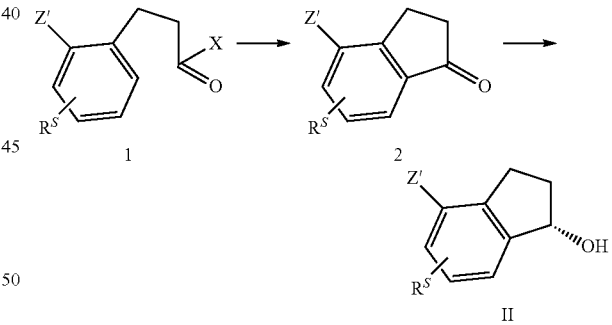

Starting compounds III such as (6-hydroxy-benzofuran-3-yl)acetic acid methyl ester are described in the literature or may be obtained in analogy to processes described in the prior art.

Alternatively, compounds of formula I' may be obtained from compounds 4 which, in turn, may be assembled from the reported compound 3 and compounds II (Scheme 2); $R^S$, $R^a$ and $Z'$ in Scheme 2 have the meanings as defined hereinbefore and hereinafter. The latter transformation may be carried out as described above applying the conditions of the Mitsunobu reaction or variations thereof. Conversion of compounds 4 to compounds I', wherein $R^a$ is H, may be accomplished by treating compounds 4 with a hydroxide salt, such as NaOH, KOH and LiOH, or an alcoholate, such as $MOC_{1-10}$-alkyl, preferably $MOCH_3$, $MOCH_2CH_3$, $MOCH_2CH_2CH_3$, MOCH (CH$_3$)$_2$, MOC(CH$_3$)$_3$, wherein M denotes Li, Na and K, in water or an aqueous solution of an alcohol, such as methanol, ethanol, propanol and isopropanol, acetonitrile, N,N-dimethylformamide, N,N-dimethylacetamide, N-methylpyrrolidone, dimethylsulfoxide, tetrahydrofuran, 1,4-dioxane, 1,2-dimethoxyethane, acetone, and toluene, preferably at 0 to 120° C. Compounds of formula I', wherein R$^a$ denotes C$_{1-4}$-alkyl, may be obtained under anhydrous conditions using MOC$_{1-4}$-alkyl (M is Li, Na or K) in C$_{1-4}$-alkyl-OH. In addition, the esters of this type may also be obtained from the carboxylic acid derivative, R$^a$ is H, using conventional methods of esterification.

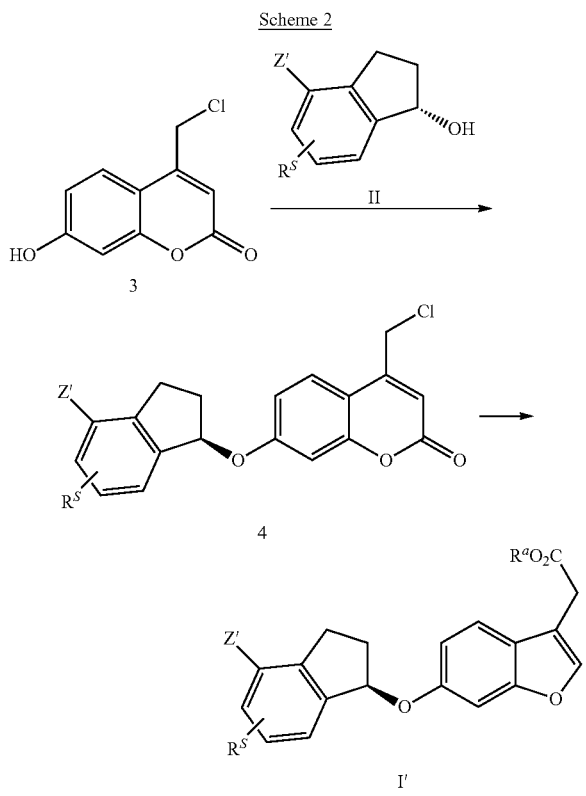

Scheme 2

The asymmetric catalytic hydrogenation reaction according to step a) mentioned under the third aspect of the invention and step d) mentioned under the fourth aspect of the invention is performed in an hydrogen atmosphere, using hydrogen or a hydrogen source, such as formate or silane, and a transition metal catalyst derived from, e.g., Ir, Rh, Ru, Pd or Fe, preferably Ru, Ir or Rh, and a chiral auxiliary, as an asymmetric catalyst, in the presence or absence of a base or an acid, preferably in the presence of a base. Preferred catalysts are [Ru(p-cymene)Cl$_2$]$_2$ and Rh(COD)$_2$OTf, combined with a ligand as chiral auxiliary selected from BINAP, DiPAMP, Monophos, Chiraphos, EtDuphos, Phanephos, Josi-Phos or S,S-Et-Ferrotane or Solvias J-13-1, preferably Josi-Phos.

The amount of the catalyst to be used is about 0.001 to about 0.1 mol equivalents per 1 mol of compound to be hydrogenated, preferably about 0.002 to about 0.05 mol equivalents. Catalyst and ligand normally are used in a molar ratio of catalyst:ligand=5:1 to 1:10, preferably 2:1 to 1:4.

This reaction is generally carried out in a solvent which is not particularly limited as long as it is inert to the reaction and can solubilize the starting compound and the catalyst. For example, aromatic hydrocarbons such as toluene or xylene, aliphatic hydrocarbons such as heptane or hexane, halogenated hydrocarbons such as methylene chloride, ethers such as diethyl ether, tetrahydrofuran, methyltetrahydrofuran or dioxane, alcohols such as methanol, ethanol, 2-propanol, butanol or benzyl alcohol, nitriles such as acetonitrile, amides such as N,N-dimethylformamide, sulfoxides such as dimethyl sulfoxide, can be used, optionally in a mixture at an appropriate ratio. The solvent is preferably an alcohol, an ester or a halogenated hydrocarbon, methanol, isopropylacetate, tetrahydrofuran and dichloromethane are particularly preferred. The above-mentioned solvents are preferably used for the reaction after drying and deaeration. The amount of the solvent to be used is appropriately determined according to the solubility of the compound to be hydrogenated. For example, when alcohol (preferably methanol) is used as a solvent, the reaction can be performed almost without solvent or in a solvent in a 100-fold or more weight relative to the compound to be hydrogenated. Generally, a solvent in about 2- to about 50-fold weight relative to the compound to be hydrogenated is preferably used.

As the base an inorganic base or an organic base can be used. Examples of the inorganic base include alkali metal hydroxides such as lithium hydroxide, potassium hydroxide, sodium hydroxide or cesium hydroxide, carbonates such as sodium carbonate, potassium carbonate or cesium carbonate, hydrogencarbonates such as sodium hydrogen carbonate or potassium hydrogen carbonate, acetates such as sodium acetate or potassium acetate, phosphates such as sodium phosphate, or monohydrogen phosphates such as potassium or sodium monohydrogen phosphate. Examples of the organic base include aliphatic amines such as trimethylamine, triethylamine, N-methylmorpholine, diethylamine, diisopropylamine, cyclohexylamine or ethylenediamine, or aromatic amines such as pyridine, picoline. Preferred bases are selected from aliphatic amines, triethylamine is most preferred. The amount of the base to be used is about 0.01 to about 10 mol equivalents per 1 mol of compound to be hydrogenated, preferably 0.1 to 10 mol equivalents.

The hydrogenation can be performed by batch type and continuous type reactions. The hydrogenation is preferably performed in the presence of hydrogen, and the hydrogen pressure is, for example, 1-50 bar, preferably 3-50 bar, more preferred 10-30 bar. The reaction temperature is generally −30° C.-100° C., preferably 0-80° C., more preferably 10-50° C. The reaction time is generally 0.1-70 h, preferably 1-50 h, more preferably 10-30 h.

Compounds of formula V and V' obtained by an asymmetric hydrogenation reaction may be purified by a known means (e.g., fractional recrystallization, chiral column method, or diastereomer salt method).

Step b-1) mentioned under the third aspect of the invention and step c-1) mentioned under the fourth aspect of the invention are preferably performed via a transition metal catalyzed coupling reaction. The coupling is conducted with R$^1$ as the nucleophilic partner bearing the metal or pseudo-metal group such as B(OH)$_2$, B(OCMe$_2$CMe$_2$O), B(O$_2$CCH$_2$)$_2$NCH$_3$, or BF$_3$K at the carbon to be coupled and the indane residue as the electrophilic partner bearing a leaving group such as Br and Cl. The reaction is preferably mediated by a transition metal complex derived from palladium. The catalyst may be a preformed complex, such as Pd(PPh$_3$)$_4$, PdCl$_2$[1,1'-bis(diphenylphosphino)ferrocene], dichloro[1,3-bis(2,6-diisopropylphenyl)-imidazol-2-ylidene]-(3-chloropyridyl)-palladium (II) (PEPPSI-IPr) or dichloro[1,3-bis(2,6-dipent-3-ylphenyl) imidazol-2-ylidene](3-chloropyridyl)-palladium(II) (PEPPSI-IPent), or formed in situ from a salt of the transition metal, such as fluoride, chloride, bromide, iodide, acetate, triflate or trifluoroacetate, or a Pd(0) complex, such as Pd$_2$(dba)$_3$ (dba=dibenzylideneacetone), and a ligand, such as phosphines, e.g. tri-tert-butylphosphine, tricyclohexylphosphine, di-(1-adamantyl)-n-butylphosphine, optionally substituted biphenyl-dicyclohexylphosphines (e.g., S-Phos, Ru-Phos, X-Phos), optionally substituted biphenyl-di-tert-butylphosphines, 4-(N,N-dimethylphenyl)-di-tert-butylphosphine (Amphos), 1,1'-bis(diphenylphosphino)-ferrocene (dppf), or triphenylphosphine. The reaction using boronic acids or esters or trifluoroborates is preferably carried out in the presence of water and a base, e.g. NaOH, KOH, KF, $Na_2CO_3$, $K_2CO_3$, $Cs_2CO_3$ or $K_3PO_4$, in toluene, tetrahydrofuran, 1,2-dimethoxyethane, 1,4-dioxane, N,N-dimethylformamide, N,N-dimethylacetamide, N-methylpyrrolidinone, alcohol, water, or mixtures thereof, at 10 to 180° C.

Step b-2) mentioned under the third aspect of the invention and step c-2) mentioned under the fourth aspect of the invention are preferably performed as described for steps b-1) and c-1) employing $R^1$ and indane with reversed reactivity at the carbons to be coupled, i.e. $R^1$ is the electrophilic component bearing the leaving group, such as Br and Cl, and indane is the nucleophilic partner bearing the metal or pseudo-metal group, such as $B(OH)_2$, $B(OCMe_2CMe_2O)$, $B(O_2CCH_2)_2$ $NCH_3$, or $BF_3K$.

Step b-4) mentioned under the third aspect of the invention and step c-4) mentioned under the fourth aspect of the invention are preferably performed with the indane bearing a boronic acid group, Br or I at the carbon to be coupled and (Het)Ar—OH. The indane bearing a boronic acid group is preferably coupled employing copper(II) acetate in the presence of a base, e.g. pyridine or triethylamine, molecular sieves, optionally a co-oxidant, e.g., oxygen, in a solvent, e.g., dichloromethane, at 0 to 60° C. The indane carrying Br or I at the carbon to be coupled are preferably reacted in the presence of a catalyst derived from either palladium or copper, particularly copper. The active catalyst may be an elemental form of the transition metal or formed from a salt of the transition metal, such as fluoride, chloride, bromide, iodide, oxide, acetate, triflate, or trifluoroacetate, which are optionally combined with ligands, such as phosphines, e.g., tri-tert-butylphosphine, tricyclohexylphosphine, optionally substituted biphenyl-dicyclohexylphosphines, optionally substituted biphenyl-di-tert-butylphosphines, 1,1'-bis(diphenylphosphino)-ferrocene (dppf), triphenylphosphine, tritolylphosphine, or trifurylphosphine, phosphites, 1,3-disubstituted imidazole carbenes, 1,3-disubstituted imidazolidine carbenes, pyridines, dipyridines, salicylaldoxime, 2,2,6,6-tetramethylheptan-3,5-dione, N,N-dimethylglycine, or optionally methylated phenanthrolines. The reaction is preferably carried out in the presence of a base, e.g., NaOH, KOH, $Na_2CO_3$, $K_2OC_3$, $Cs_2CO_3$, $K_3PO_4$, triethylamine or ethyldiisopropylamine, in toluene, tetrahydrofuran, methyltetrahydrofuran, 1,2-dimethoxyethane, 1,4-dioxane, N,N-dimethylformamide, N,N-dimethylacetamide, N-methylpyrrolidinone, alcohol, water, or mixtures thereof, at 10 to 180° C. Preferably, the 4-bromo- or iodoindane is used with copper iodide, dimethylglycine, and $Cs_2CO_3$, in 1,4-dioxane at 100° C.

Step b-3) mentioned under the third aspect of the invention and step c-3) mentioned under the fourth aspect of the invention are preferably performed using the 4-hydroxyindane derivative and (Het)Ar—$B(OH)_2$ or (Het)Ar—Hal, Hal is Cl, Br, or I, preferably Br, under the conditions described above for the steps b-3) and c-3).

Step b-5) mentioned under the third aspect of the invention and step c-5) mentioned under the fourth aspect of the invention are preferably carried out using the indane derivatized with a leaving group, such as Cl, Br or I, at the carbon atom to be coupled and $R^1$—$CH_2$—$BF_3M$ (M is preferably K, $NH_4$ and $Me_4N$). The reaction is preferably conducted with a palladium derived catalyst, e.g. palladium acetate combined with 2-dicyclohexylphosphino-2',4',6'-triisopropyl-1,1'-biphenyl (X-Phos) or 2-dicyclohexylphosphino-2',6'-diisopropoxy-1,1'-biphenyl (Ru-Phos), in the presence of a base, e.g. $Cs_2CO_3$ or $K_2OC_3$, in a mixture of water and tetrahydrofuran, methyltetrahydrofuran, 1,4-dioxane, 1,2-dimethoxy-ethane, N,N-dimethylformamide, N,N-dimethylacetamide, N-methylpyrrolidinone, dimethylsulfoxide, and/or toluene, at 30 to 120° C.

The present invention will become more apparent from the following detailed Examples which illustrate the principles of the invention.

ABBREVIATIONS

| | |
|---|---|
| Ac | acetyl |
| ACN | Acetonitrile |
| aq. | Aqueous |
| conc. | Concentrated |
| CH | Cyclohexane |
| DCM | Dichloromethane |
| DMF | N,N-dimethylformamide |
| dr | diastereomeric ratio |
| eq | Equivalent |
| EtOAc | Ethylacetate |
| EtOH | Ethanol |
| Ex | Example |
| h | Hour |
| IPA | Isopropanol |
| IPrOAc | Isopropyl acetate |
| MCH | Methylcyclohexane |
| MeOH | Methanol |
| MeTHF | 2-methyltetrahydrofuran |
| min | Minute |
| ND | not determined |
| NMP | N-methyl-2-pyrrolidone |
| PE | Petrolether |
| Rf | retention factor |
| r.t. | room temperature |
| sat. | Saturated |
| TEA | Triethylamine |
| TFA | trifluoroacetic acid |
| THF | Tetrahydrofuran |
| tR | retention time on HPLC |

Catalysts:

| abbreviation | name | Structure |
|---|---|---|
| Pd(Amphos)$_2$Cl$_2$ | Dichloro-bis(p-dimethylaminophenyl-di-t-butylphosphine)palladium(II) | 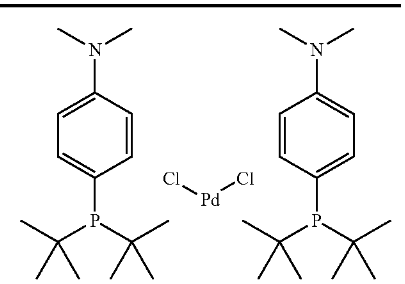 |

| abbreviation | name | Structure |
|---|---|---|
| Rh(COD)₂OTf | Bis(1,5-cyclooctadiene)rhodium(I) trifluormethanesulfonate | |
| [Ru(p-cymene)Cl₂]₂ | Dichloro(p-cymene)ruthenium(II) dimer | |

Ligands:

| abbreviation | name | Structure |
|---|---|---|
| cataCXiumT2 | (1R)-(+)-3-[di-(3,5-dimethylphenyl)phosphino]-2-(4-diphenylphosphino-2,5-dimethylthien-3-yl)-1,7,7-trimethylbicyclo [2.2.1]hept-2-ene | 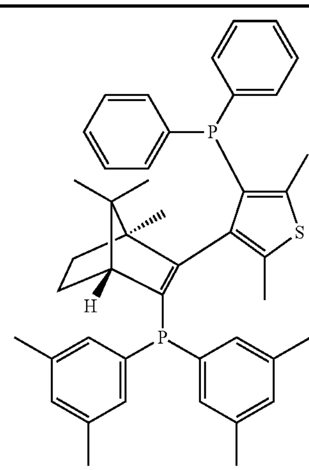 |
| Josi-Phos | (S)-1-((R)-2-(Di(2-furyl)phosphino)ferrocenyl)ethyldi-tert-butyl phosphine | 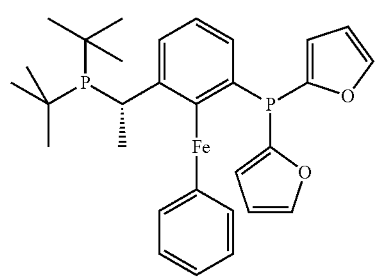 |
| S,S-Et-Ferrotane | (−)-1,1'-bis((2S,4S)-2,4-diethylphosphotano)ferrocene | 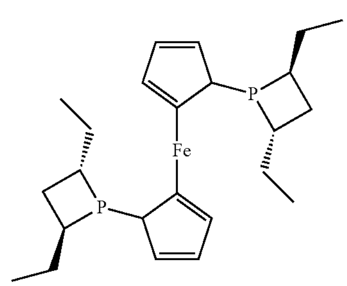 |

| abbreviation | name | Structure |
|---|---|---|
| Solvias J-13-1 | (R)-1-[(S)-2-Di(4-methoxy-3,5-dimethylphenyl)phosphino)ferrocenyl]ethyldi-tert-butylphosphine (CAS: 187733-50-2) | 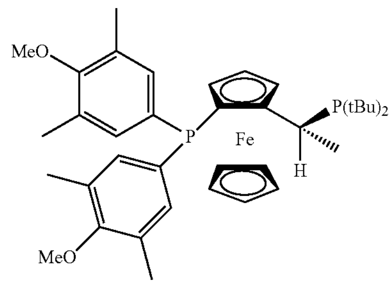 |

LC-Methods:

Method Name: 1
Column: XBridge C18, 3 × 30 mm, 2.5 μm
Column Supplier: Waters

| Gradient/ Solvent Time [min] | % Solvent [H$_2$O, 0.1% TFA] | % Solvent [Acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: 2
Column: XBridge C18, 3 × 30 mm, 2.5 μm
Column Supplier: Waters

| Gradient/ Solvent Time [min] | % Solvent [H$_2$O, 0.1% TFA] | % Solvent [Acetonitrile] | Flow [ml/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: 3
Column: Sunfire, 3 × 30 mm, 2.5 μm
Column Supplier: Waters

| Gradient/ Solvent Time [min] | % Solvent [H$_2$O, 0.1% TFA] | % Solvent [Acetonitrile] | Flow [ml/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: 4
Column: Sunfire, 4.6 × 50 mm, 3.5 μm
Column Supplier: Waters

| Gradient/ Solvent Time [min] | % Solvent [H$_2$O, 0.2% KH$_2$PO$_4$] pH 3.0 | % Solvent [Acetonitrile] | Flow [ml/min] | Temperature [° C.] |
|---|---|---|---|---|
| 0.00 | 90 | 10 | 1.4 | 40 |
| 1.00 | 80 | 20 | 1.4 | 40 |
| 4.00 | 10 | 90 | 1.4 | 40 |
| 5.50 | 10 | 90 | 1.4 | 40 |

Intermediate 1

6-(R)-(7-Fluoro-4-(4-(3-hydroxy-3-methylbutoxy)-2,6-dimethylphenyl)-indan-1-yloxy)benzofuran-3-yl)acetic acid

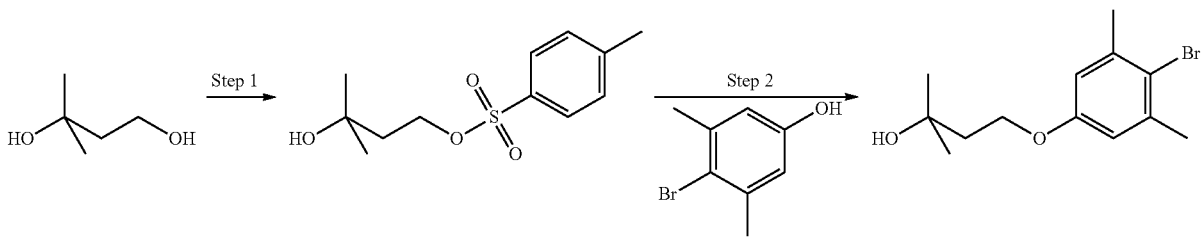

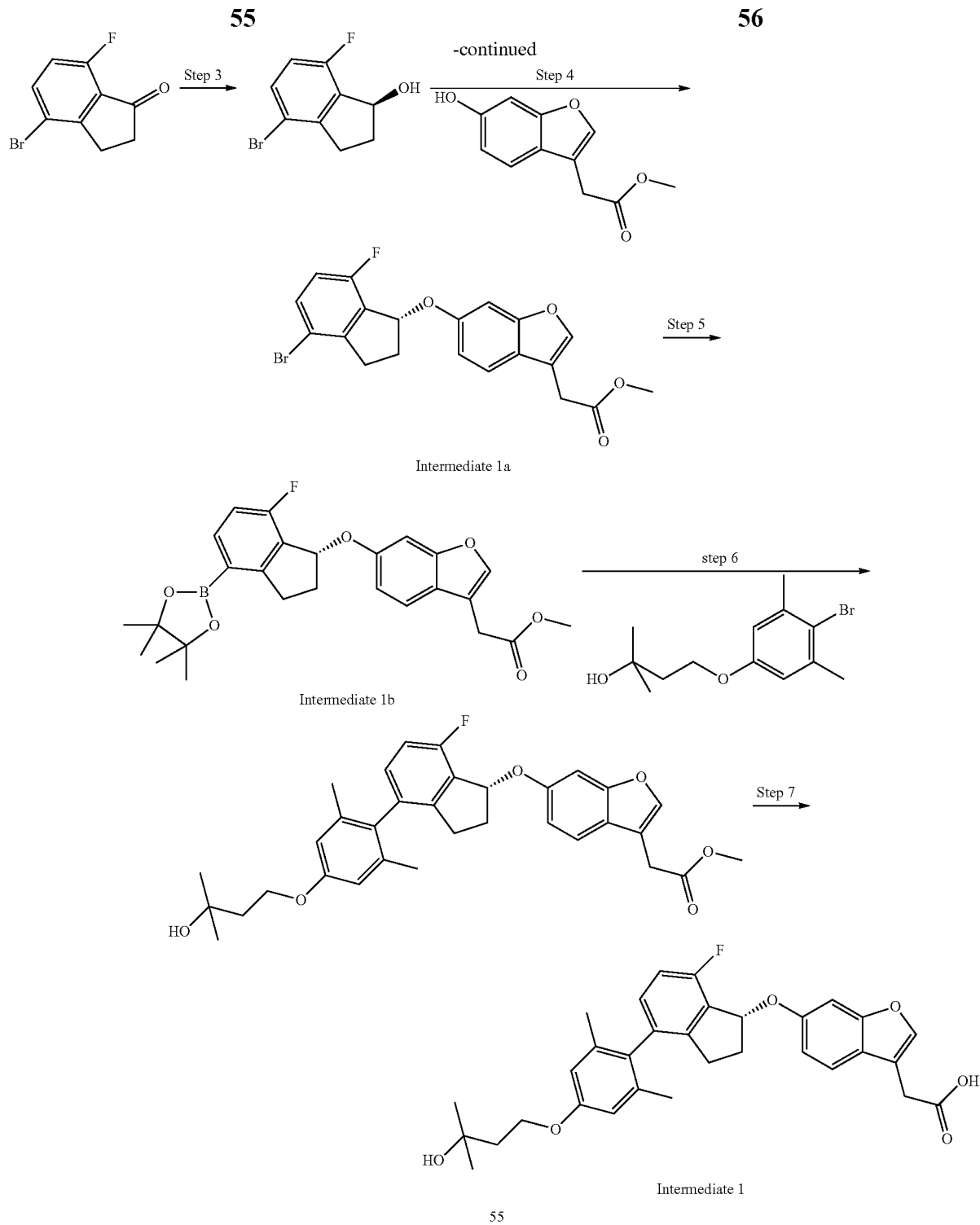

Intermediate 1

Step 1: Toluene-4-sulfonic acid 3-hydroxy-3-methylbutyl ester 10.0 ml (93.7 mmol) of 3-methylbutane-1,3-diol and 7.60 ml (94.9 mmol) pyridine are dissolved in 100 ml DCM. The mixture is cooled in an ice bath. 15.0 g (78.7 mmol) of 4-methylbenzenesulfonyl chloride are added portionwise. The reaction mixture is stirred at r.t. for 16 h. The reaction mixture is poured into 100 ml of 1N aq. HCl and stirred for 10 min. Then the layers are separated. The aq. layer is extracted with DCM. The combined organic layers are washed with brine and dried. The solvent is evaporated and the residue is chromatographed on silica gel (PE/EtOAc) to give the title compound. Yield: 15.3 g; Mass spectrum (ESI$^+$): m/z=276 [M+NH$_4$]$^+$.

Step 2: 4-(4-Bromo-3,5-dimethylphenoxy)-2-methylbutan-2-ol 40.7 g (157 mmol) of toluene-4-sulfonic acid 3-hydroxy-3-methylbutyl ester (product of step 1), 34.0 g (169 mmol) of 4-bromo-3,5-dimethylphenol and 25.0 g (180 mmol) of potassium carbonate are dissolved in 114 ml DMF. The reaction mixture is stirred at 50° C. for 16 h. The reaction mixture is poured into aq. NH$_4$Cl solution and stirred. Then the layers are separated. The aq. layer is extracted with DCM. The combined organic layers are washed with water and dried. The solvent is evaporated and the residue is chromatographed on silica gel (PE/EtOAc) to give the title compound. Yield: 38.3 g; Mass spectrum (ESI$^+$): m/z=287 [M+H]$^+$.

Step 3: (S)-4-Bromo-7-fluoro-2,3-dihydro-1H-inden-1-ol 20.0 g (87.3 mmol) 4-bromo-7-fluoro-2,3-dihydro-1H-inden-1-one, 142 ml toluene and 13.9 g (138 mmol) TEA are added into a vessel. The mixture is degassed and heated to 40° C. Then, 272 mg (0.44 mmol) chloro{[(1S,2S)-(−)-2-amino-1,2-diphenylethyl](4-toluenesulfonyl)amido}-(mesitylene) ruthenium(II) is added before a mixture of 7.03 g (153 mmol) formic acid (98%) and 3.00 mL toluene is added over a time period of 60 min. The funnel is rinsed with 7.00 ml toluene. Stirring is continued at 40° C. for approx. 90 min until full conversion (HPLC). 1.43 g (8.73 mmol) N-acetyl-L-cystein is added and stirring is continued for 30 min. A mixture of 15.8 g (160 mmol) conc. HCl in 24 ml water is added and the aqueous phase is separated. The organic phase is washed with 35.0 ml water and 140 ml solvent is distilled off. 90 ml IPA is added and 70 ml solvent is distilled off. To the residue 50 ml water is added and the mixture is cooled to 35° C. Then, seeds are added followed by 50 ml water. The suspension is cooled to 22° C. and stirred for 2 h. The product is filtered off, washed with water (2×30 ml) and dried. Yield: 18.6 g; LC (method 1): $t_R$=0.91 min; Mass spectrum (ESI$^+$): m/z=213 [M+H—H$_2$O]$^+$.

Step 4 (Intermediate 1a): (6-(R)-(4-Bromo-7-fluoroindan-1-yloxy)benzofuran-3-yl)acetic acid methyl ester A solution of 2.20 g (9.55 mmol) of di-tert.-butyl azodicarboxylate in 5.0 ml THF is added dropwise over 20 min to a solution of 2.00 g (8.66 mmol) of (S)-4-bromo-7-fluoro-2,3-dihydro-1H-inden-1-ol, 1.90 g (9.21 mmol) of (6-hydroxy-benzofuran-3-yl)acetic acid methyl ester and 2.70 ml (10.8 mmol) of tributylphosphine in 10.0 ml THF at −10° C. The resulting mixture is stirred for 45 min. The reaction mixture is diluted with 30 ml sat. aq. NaHCO$_3$ solution and stirred for 10 min, then it is filtered through celite and washed with EtOAc. The organic phase is dried and concentrated. The residue is chromatographed on silica gel (PE/EtOAc) to give the title compound. Yield: 2.47 g; LC (method 2): $t_R$=0.88 min; Mass spectrum (ESI$^+$): m/z=419 [M+H]$^+$.

Step 5 (Intermediate 1b): (6-(R)-(7-Fluoro-4-(4,4,5,5-tetramethyl-[1,3,2]dioxaborolan-2-yl)-indan-1-yloxy)benzofuran-3-yl)acetic acid methyl ester 2.47 g (5.89 mmol) of (6-(R)-(4-bromo-7-fluoroindan-1-yloxy)benzofuran-3-yl)acetic acid methyl ester (product of step 4) and 1.60 g (6.30 mmol) of bis(pinacolato)diboron are dissolved in 20.0 ml 1,4-dioxane. 1.30 g (13.3 mmol) of potassium acetate are added and the mixture is purged for 10 min with argon. 40.0 mg (0.05 mmol) of [1,1′-bis(diphenylphosphino)-ferrocene]-dichloropalladium-(II) are added. The reaction mixture is stirred at reflux for 4 h. After cooling to r.t. the mixture is partitioned between diethylether and sat. aq. NH$_4$Cl solution. The organic phase is washed with brine, dried and concentrated. The residue is chromatographed on silica gel (PE/EtOAc) to give the title compound. Yield: 1.97 g; LC (method 3): $t_R$=1.04 min; Mass spectrum (ESI$^+$): m/z=467 [M+H]$^+$.

Step 6: (6-(R)-(7-Fluoro-4-(4-(3-hydroxy-3-methyl-butoxy)-2,6-dimethylphenyl)-indan-1-yloxy)benzofuran-3-yl)acetic acid methyl ester 218 mg (0.47 mmol) of (6-(R)-(7-fluoro-4-(4,4,5,5-tetramethyl-[1,3,2]dioxaborolan-2-yl)-indan-1-yloxy)benzofuran-3-yl)acetic acid methyl ester (product of step 5) are dissolved in 4.0 ml toluene. 1.0 ml (0.5 mmol) of the 0.5 mol/l solution in toluene of 4-(4-bromo-3,5-dimethylphenoxy)-2-methylbutan-2-ol (product of step 2) and 100 μl water are added. 20.0 mg (0.05 mmol) of dicyclohexyl-(2′,6′-dimethoxy-biphenyl-2-yl)-phosphane and 200 mg (0.94 mmol) of potassium phosphate are added and the mixture is purged with argon. Then 6.0 mg (0.03 mmol) of palladium(II) acetate are added and the reaction mixture is stirred at 110° C. for 2 h. After cooling to r.t. to the mixture is added sat. aq. NH$_4$Cl solution. The phases are separated and the organic layer is extracted with EtOAc. The combined organic phases are dried and concentrated. The residue is chromatographed on silica gel (PE/EtOAc) to give the title compound. Yield: 201 mg; LC (method 3): $t_R$=0.95 min. 4-(4-Bromo-3,5-dimethylphenoxy)-2-methylbutan-2-ol may be substituted with 4-(4-chloro-3,5-dimethylphenoxy)-2-methylbutan-2-ol and the 4,4,5,5-tetramethyl-[1,3,2]dioxaborolane derivative with the corresponding boronic acid to give the title compound under the conditions described. The coupling may also be accomplished employing the reaction conditions described or variants thereof (e.g., using Pd(4-dimethylaminophenyl-di-tert-butylphosphine)$_2$Cl$_2$ as catalyst source) and the coupling partners with their reversed reactivity, i.e. 4-[3,5-dimethyl-4-(4,4,5,5-tetramethyl-[1,3,2]dioxaborolan-2-yl)-phenoxy]-2-methylbutanol or the corresponding boronic acid (Intermediate 23) and (6-(R)-(4-bromo-7-fluoroindan-1-yloxy)benzofuran-3-yl)acetic acid methyl ester.

Step 7: (6-(R)-(7-Fluoro-4-(4-(3-hydroxy-3-methyl-butoxy)-2,3-dimethylphenyl-indan-1-yloxy)benzofuran-3-yl)acetic acid 201 mg (0.37 mmol) of (6-(R)-(7-fluoro-4-(4-(3-hydroxy-3-methylbutoxy)-2,6-dimethylphenyl)-indan-1-yloxy)benzofuran-3-yl)acetic acid methyl ester (product of step 6) are dissolved in 2.0 ml EtOH. 800 μl (0.80 mmol) of KOH (1N in EtOH) are added and the reaction mixture is stirred at r.t. for 16 h. The mixture is diluted with EtOAc. 800 μl of 1N aq. HCl solution are added under ice cooling. The mixture is diluted with brine. The phases are separated, the organic layer is dried and concentrated. The residue is chromatographed on silica gel (PE/EtOAc) to give the title compound. Yield: 175 mg; LC (method 3): $t_R$=0.72 min; Mass spectrum (ESI$^+$): m/z=533 [M+H]$^+$.

The compound is also obtained using the carboxylic acid of the benzofuran-3-yl acetic ester derivative or a salt thereof for the coupling reaction, i.e. (6-(R)-(4-bromo-7-fluoroindan-1-yloxy)benzofuran-3-yl)acetic acid or (6-(R)-(7-fluoro-4-(4,4,5,5-tetramethyl-[1,3,2]dioxaborolan-2-yl)-indan-1-yloxy) benzofuran-3-yl)acetic acid. E.g., 4-[3,5-dimethyl-4-(4,4,5,5-tetramethyl-[1,3,2]dioxaborolan-2-yl)-phenoxy]-2-methylbutanol or the corresponding boronic acid (Intermediate 23) and (6-(R)-(4-bromo-7-fluoroindan-1-yloxy)benzofuran-3-yl)acetic acid (e.g., as acid or the piperazinium or morpholinium salt) are coupled in the presence of K$_2$OC$_3$ and Pd(4-dimethylaminophenyl-di-tert-butylphosphine)$_2$Cl$_2$ in a mixture of n-propanol and water (1:2) at 90° C. The reaction partners with their reversed reactivity at the carbons to be coupled also yield the title compound under the same conditions.

The carboxylic acid of Intermediate 1a is also obtained following the proceeding described below:

(6-(R)-(4-Bromo-7-fluoroindan-1-yloxy)benzofuran-3-yl)acetic acid

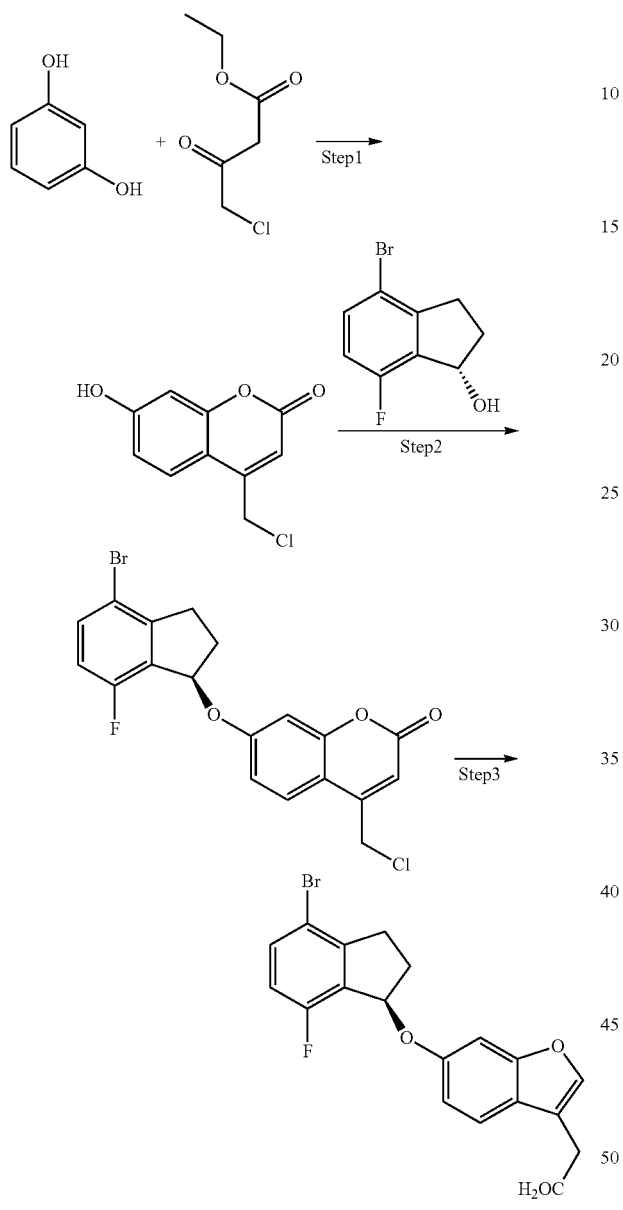

Step 1: 4-Chloromethyl-7-hydroxy-chromen-2-one 33.5 g (304 mmol) resorcine is dissolved in 105 ml acetic acid at 40° C. 25.0 g (152 mmol) 4-chloroacetic acid ethylester is added and the funnel is rinsed with 10 ml acetic acid. Then, 26.8 g (274 mmol) conc. $H_2SO_4$ (97%) is added and the funnel is rinsed with 10 ml acetic acid. The mixture is heated to 50° C. for approx. 2 h. After full conversion, 330 ml water is added. The reaction mixture is cooled to r.t. and the suspension is stirred overnight. The product is filtered off, washed with water (2×50 ml) and dried. Yield: 23.4 g; $R_f$=0.42 (silica gel, PE/EtOAc=6/4); Mass spectrum (ESI): m/z=211 $[M+H]^+$.

Step 2: 7-((R)-4-Bromo-7-fluoroindan-1-yloxy)-4-chloromethyl-chromen-2-one

Under argon 10.0 g (43.3 mmol) (S)-4-bromo-7-fluoroindan-1-ol and 9.57 g (45.4 mmol) 4-chloromethyl-7-hydroxy-chromen-2-one (product from step 1) are dissolved in 70 ml dry THF and cooled to −15° C. 10.9 g (54.1 mmol) tri-n-butylphosphine is added and the funnel is rinsed with 5 ml THF. Then, 10.9 g (54.1 mmol) diisopropyl azodicarboxylate is added and the funnel is rinsed with 5 ml THF. Stirring is continued at −15° C. for approx. 2.5 h. The mixture is heated to 60° C. and 50% of the solvent is distilled off. Afterwards, the remaining mixture is co-distilled twice with acetonitrile (2×80 ml). The obtained suspension is cooled to 0° C., the product is filtered off, washed with cold acetonitrile (2×20 ml) and finally dried in vacuum. Yield: 13.6 g; $R_f$=0.28 (silica gel, PE/EtOAc=8/2); Mass spectrum (ESI): m/z=423 $[M+H]^+$.

Step 3: [6-((R)-4-Bromo-7-fluoroindan-1-yloxy)benzofuran-3-yl]-acetic acid

To 15.0 g (35.4 mmol) 7-((R)-4-bromo-7-fluoroindan-1-yloxy)-4-chloromethyl-chromen-2-one (product from step 2) in 45 ml EtOH, 9.29 ml (177 mmol) aq. NaOH (50%) is added. The funnel is rinsed with 50 ml water and the mixture is heated to reflux for approx. 0.5 h. Then, over a time period of 30 min a mixture of 30 ml water and 14.7 ml (177 mmol) conc. HCl (37%) is added. The suspension is cooled to r.t., the product is filtered off, washed with EtOH/water (1:1, 2×30 ml) and dried. Yield: 14.0 g; $R_f$=0.38 (silica gel, PE/EtOAc/AcOH=6/4/0.1); Mass spectrum (ESI): m/z=405 $[M+H]^+$.

Intermediate 2

(6-(R)-(7-Fluoro-4-(4-(2-hydroxy-2-methyl-propoxy)-2,6-dimethylphenyl)-indan-1-yloxy)benzofuran-3-yl)acetic acid

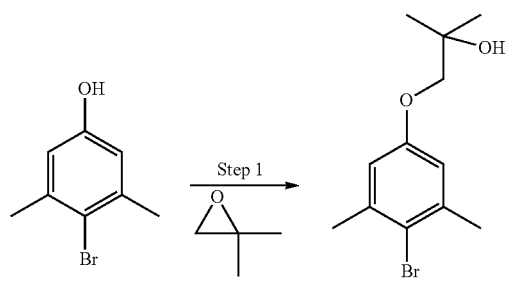

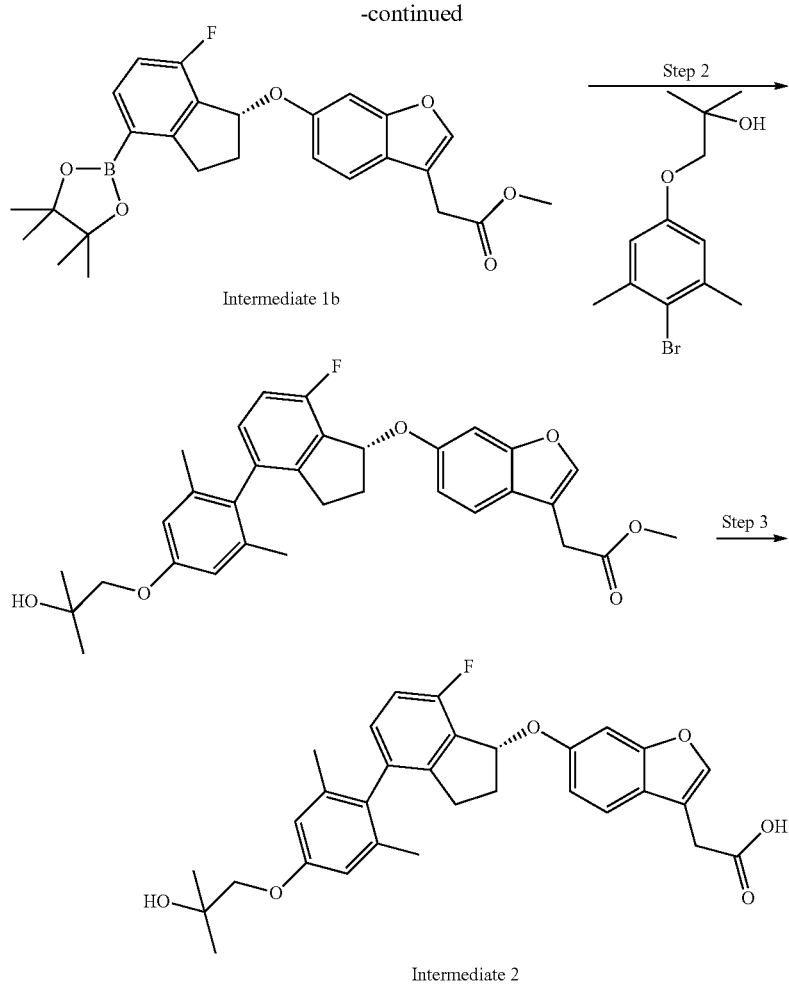

Intermediate 1b

Intermediate 2

Step 1: 1-(4-Bromo-3,5-dimethylphenoxy)-2-methylpropan-2-ol

In a microwave vial 2.20 g (0.03 mmol) of 2,2-dimethyloxirane are added to a suspension of 6.00 g (0.03 mmol) of 4-bromo-3,5-dimethylphenol and 11.0 g (0.08 mmol) $K_2OC_3$ in 6.0 ml DMF. The vial is sealed and the mixture is heated for 48 hours to 120° C. After cooling to r.t., the mixture is partitioned between sat. aq. $Na_2CO_3$ solution and EtOAc. The aq. phase is extracted twice with EtOAc and the combined organic phases are dried and concentrated. The residue is chromatographed on silica gel (CH/EtOAc 100:050:50) to give the title compound. Yield: 2.9 g; LC (method 4): $t_R$=1.76 min; Mass spectrum (ESI$^+$): m/z=273 [M+H]$^+$.

Step 2: (6-(R)-(7-Fluoro-4-(4-(2-hydroxy-2-methylpropoxy)-2,6-dimethylphenyl)-indan-1-yloxy)benzofuran-3-yl)acetic acid methyl ester The title compound is prepared from 1-(4-bromo-3,5-dimethylphenoxy)-2-methyl-propan-2-ol (product of step 1) and (6-(R)-(7-fluoro-4-(4,4,5,5-tetramethyl-[1,3,2]dioxaborolan-2-yl)-indan-1-yloxy)benzofuran-3-yl)acetic acid methyl ester (intermediate 1 b) following a procedure analogous to that described in step 6 of Intermediate 1. LC (method 3): $t_R$=0.91 min.

1-(4-Bromo-3,5-dimethylphenoxy)-2-methyl-propan-2-ol may be substituted with 1-(4-chloro-3,5-dimethylphenoxy)-2-methyl-propan-2-ol and the 4,4,5,5-tetramethyl-[1,3,2]dioxaborolane derivative with the corresponding boronic acid to provide the title compound under the conditions described.

The coupling may also be accomplished applying the conditions described or variants thereof (e.g., using Pd(4-dimethylaminophenyl-di-tert-butylphosphine)$_2Cl_2$ as catalyst source) and the coupling partners with their reversed reactivity, i.e. 1-[3,5-dimethyl-4-(4,4,5,5-tetramethyl-[1,3,2]dioxaborolan-2-yl)-phenoxy]-2-methyl-2-propanol or the corresponding boronic acid (e.g., prepared in analogy to Intermediate 23) and (6-(R)-(4-bromo-7-fluoroindan-1-yloxy)benzofuran-3-yl)acetic acid methyl ester.

Step 3: (6-(R)-(7-Fluoro-4-(4-(2-hydroxy-2-methylpropoxy)-2,6-dimethylphenyl)-indan-1-yloxy)benzofuran-3-yl)acetic acid The title compound is prepared from (6-(R)-(7-fluoro-4-(4-(2-hydroxy-2-methyl-propoxy)-2,6-dimethylphenyl)-indan-1-yloxy)benzofuran-3-yl)acetic acid methyl ester (product of step 2) following a procedure analogous to that described in step 7 of Intermediate 1. LC (method 3): $t_R$=0.68 min; Mass spectrum (ESI$^+$): m/z=519 [M+H]$^+$.

The title compound is also obtained using the carboxylic acid of the benzofuran-3-yl acetic ester derivative or a salt thereof for the coupling reaction, i.e. (6-(R)-(4-bromo-7-fluoroindan-1-yloxy)benzofuran-3-yl)acetic acid or (6-(R)-(7-fluoro-4-(4,4,5,5-tetramethyl-[1,3,2]dioxaborolan-2-yl)-indan-1-yloxy)benzofuran-3-yl)acetic acid. E.g., 1-[3,5-dimethyl-4-(4,4,5,5-tetramethyl-[1,3,2]dioxaborolan-2-yl)-phenoxy]-2-methyl-2-propanol or the corresponding boronic acid (e.g., prepared in analogy to Intermediate 23) and (6-(R)-(4-bromo-7-fluoroindan-1-yloxy)benzofuran-3-yl)acetic acid (e.g., as acid or the piperazinium or morpholinium salt) are coupled in the presence of $K_2OC_3$ and Pd(4-dimethylaminophenyl-di-tert-butylphosphine)$_2$Cl$_2$ in a mixture of n-propanol and water (1:2) at 90° C. The reaction partners with their reversed reactivity at the carbons to be coupled also yield the title compound under the same conditions.

Intermediate 3

(6-(R)-(4-(2,6-Dimethyl-4-(tetrahydropyran-4-yloxy)-phenyl)-7-fluoroindan-1-yloxy)benzofuran-3-yl)acetic acid

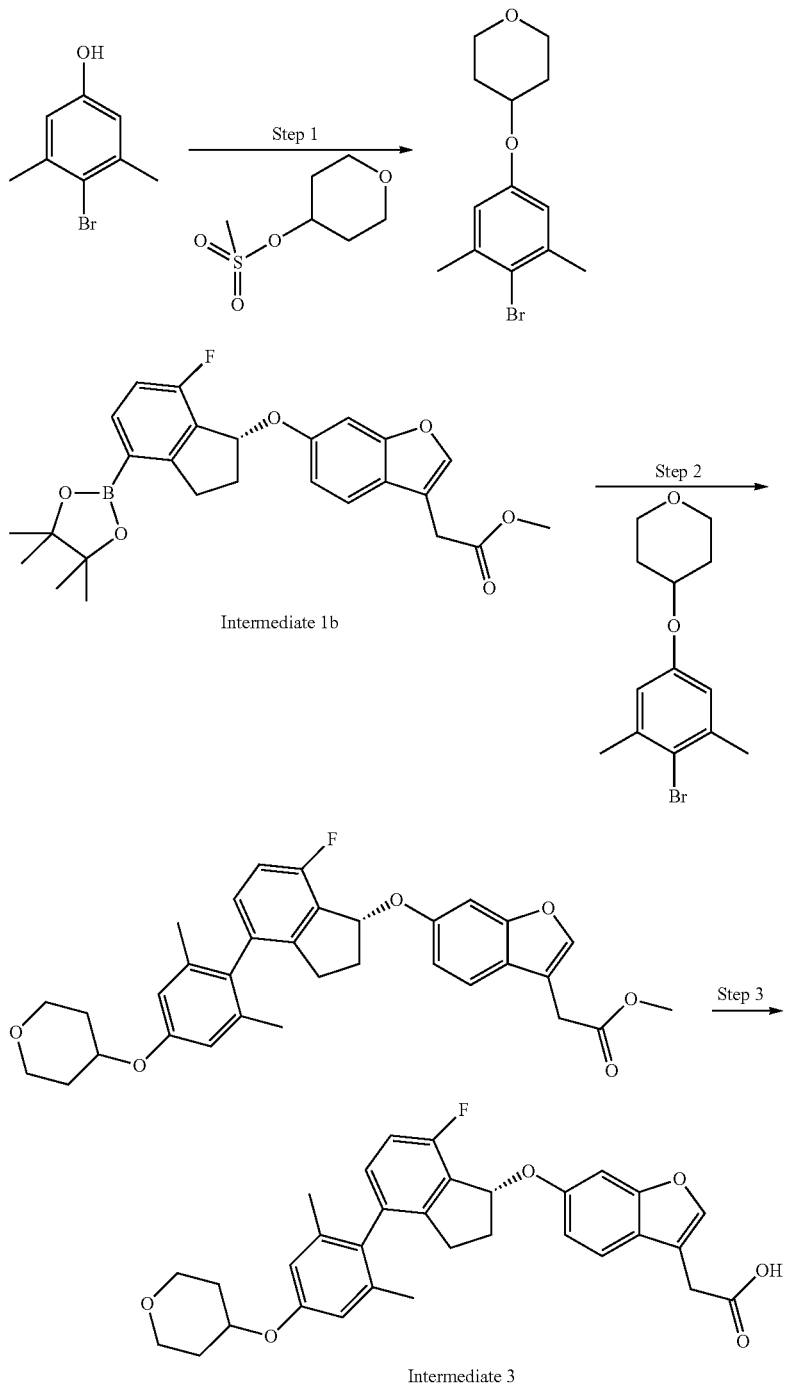

Intermediate 3

Step 1: 4-(4-Bromo-3,5-dimethylphenoxy)-tetrahydropyran

Reaction under argon atmosphere: 3.0 g (15 mmol) of 4-bromo-3,5-dimethylphenol are dissolved in 20.0 ml NMP. 20.0 g (61.4 mmol) of cesium carbonate and 11.0 g (61.0 mmol) of methanesulfonic acid tetrahydropyran-4-yl ester are added. The reaction mixture is stirred at 140° C. for 4 h. The solvent is evaporated. The residue is diluted with EtOAc and washed with water and brine. The organic layer is dried and the solvent is evaporated. The residue is chromatographed on silica gel (CH/EtOAc=99/1→60/40) to give the title compound. Yield: 4.0 g; LC (method 1): $t_R$=1.15 min; Mass spectrum (ESI+): m/z=285 [M+H]+.

Alternatively, instead of methanesulfonic acid tetrahydropyran-4-yl ester 4-chloro-tetrahydropyran, 4-bromo-tetrahydropyran, 4-iodo-tetrahydropyran, or p-toluenesulfonic acid tetrahydropyran-4-yl ester can be used. Starting from 4-hydroxypyran and 4-bromo-3,5-dimethylphenol the title compound may also be obtained using diisopropyl azodicarboxylate and tri-n-butylphosphine in tetrahydrofuran or 2-methyltetrahydrofuran at 20° C. (Mitsunobu reaction).

Step 2: (6-(R)-(4-(2,6-Dimethyl-4-(tetrahydropyran-4-yloxy)-phenyl)-7-fluoroindan-1-yloxy)benzofuran-3-yl)acetic acid methyl ester The title compound is prepared from 4-(4-bromo-3,5-dimethylphenoxy)-tetrahydropyran (product of step 1) and (6-(R)-(7-fluoro-4-(4,4,5,5-tetramethyl-[1,3,2]dioxaborolan-2-yl)-indan-1-yloxy)benzofuran-3-yl)acetic acid methyl ester (intermediate 1 b) following a procedure analogous to that described in step 6 of Intermediate 1. LC (method 3): $t_R$=1.01 min; Mass spectrum (ESI+): m/z=545 [M+H]+.

4-(4-Bromo-3,5-dimethylphenoxy)-tetrahydropyran may be substituted with 4-(4-chloro-3,5-dimethylphenoxy)-tetrahydropyran and the 4,4,5,5-tetramethyl-[1,3,2]dioxaborolane derivative with the corresponding boronic acid to give the title compound under the conditions described.

The coupling may also be accomplished applying the conditions described or variants thereof (e.g., using Pd(4-dimethylaminophenyl-di-tert-butylphosphine)$_2$Cl$_2$ as catalyst source) and the coupling partners with their reversed reactivity, i.e. 4-[3,5-dimethyl-4-(4,4,5,5-tetramethyl-[1,3,2]dioxaborolan-2-yl)-phenoxy]-tetrahydropyran or the corresponding boronic acid (e.g., prepared in analogy to intermediate 23) and (6-(R)-(4-bromo-7-fluoroindan-1-yloxy)benzofuran-3-yl)acetic acid methyl ester.

Step 3: (6-(R)-(4-(2,6-Dimethyl-4-(tetrahydropyran-4-yloxy)-phenyl)-7-fluoroindan-1-yloxy)benzofuran-3-yl)acetic acid The title compound is prepared from (6-(R)-(4-(2,6-dimethyl-4-(tetrahydropyran-4-yloxy)-phenyl)-7-fluoroindan-1-yloxy)benzofuran-3-yl)acetic acid methyl ester (product of step 2) following a procedure analogous to that described in step 7 of Intermediate 1. LC (method 3): $t_R$=0.80 min; Mass spectrum (ESI+): m/z=531 [M+H]+.

The title compound is also obtained using the carboxylic acid of the benzofuran-3-yl acetic ester derivative or a salt thereof for the coupling reaction, i.e. (6-(R)-(4-bromo-7-fluoroindan-1-yloxy)benzofuran-3-yl)acetic acid or (6-(R)-(7-fluoro-4-(4,4,5,5-tetramethyl-[1,3,2]dioxaborolan-2-yl)-indan-1-yloxy)benzofuran-3-yl)acetic acid. E.g., 4-[3,5-dimethyl-4-(4,4,5,5-tetramethyl-[1,3,2]dioxaborolan-2-yl)-phenoxy]-tetrahydropyran or the corresponding boronic acid (e.g., prepared in analogy to Intermediate 23) and (6-(R)-(4-bromo-7-fluoroindan-1-yloxy)benzofuran-3-yl)acetic acid (e.g., as acid or the piperazinium or morpholinium salt) are coupled in the presence of K$_2$OC$_3$ and Pd(4-dimethylaminophenyl-di-tert-butylphosphine)$_2$Cl$_2$ in a mixture of n-propanol and water (1:2) at 90° C. The reaction partners with their reversed reactivity at the carbons to be coupled also yield the title compound under the same conditions.

Intermediate 4

(6-(R)-(7-Fluoro-4-hydroxyindan-1-yloxy)benzofuran-3-yl)acetic acid

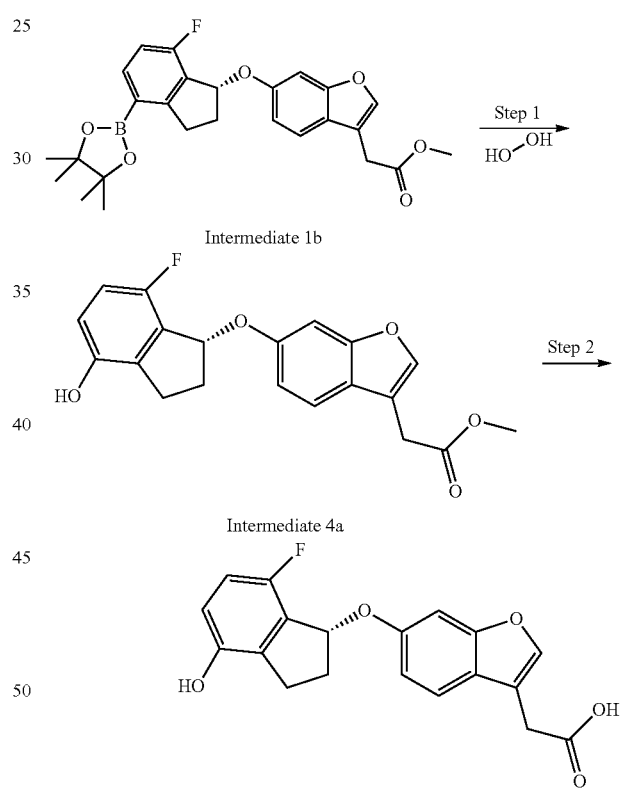

Step 1 (Intermediate 4a): (6-(R)-(7-Fluoro-4-hydroxyindan-1-yloxy)benzofuran-3-yl)acetic acid methyl ester To a solution of 1.30 g (2.79 mmol) of (6-(R)-(7-fluoro-4-(4,4,5,5-tetramethyl-[1,3,2]dioxaborolan-2-yl)-indan-1-yloxy)benzofuran-3-yl)acetic acid methyl ester (Intermediate 1b) in 10.0 ml acetic acid is added 1.0 ml (12 mmol) aq. H$_2$O$_2$ (w=25%). The mixture is stirred for 30 min at r.t. The reaction mixture is poured into 40 ml 1.25N aq. NaOH and extracted with DCM. The layers are separated and the organic layer is washed with water. After drying, the solvent is evaporated and the product is purified by chromatography on silica gel (PE/EtOAc) to give the title compound. Yield: 0.81 g; LC (method 3): $t_R$=0.31 min; Mass spectrum (ESI$^+$): m/z=357 [M+H]$^+$.

Step 2: (6-(R)-(7-Fluoro-4-hydroxyindan-1-yloxy)benzofuran-3-yl)acetic acid

The title compound is prepared from (6-(R)-(7-fluoro-4-hydroxyindan-1-yloxy)benzofuran-3-yl)acetic acid methyl ester (product of step 1) following a procedure analogous to that described in step 7 of Intermediate 1. LC (method 1): $t_R$=0.15 min; Mass spectrum (ESI$^+$): m/z=343 [M+H]$^+$.

The transformation may also be carried out using $H_2O_2$ (25 to 35% in water) in a mixture of EtOH and water (10:1) at 50° C.

Alternatively, the transformation may be accomplished with oxidants other than $H_2O_2$:
1. NaBO$_3$*4 H$_2$O in EtOH/acetic acid/H$_2$O (8:1:1) at 30° C.; optionally, toluene or another co-solvent is added.
2. N-methyl-morpholine-N-oxide in MeCN at 80° C.

Intermediate 5

(6-(R)-(7-Fluoro-4-(1-methyl-1H-indazol-6-yloxy)-indan-1-yloxy)benzofuran-3-yl)acetic acid

Step 1: (6-(R)-(7-Fluoro-4-(1-methyl-1H-indazol-6-yloxy)-indan-1-yloxy)benzofuran-3-yl)acetic acid methyl ester 250 mg (0.70 mmol) of (6-(R)-(7-fluoro-4-hydroxyindan-1-yloxy)benzofuran-3-yl)acetic acid methyl ester (Intermediate 4a), 130 mg (0.72 mmol) of copper(II) acetate and 500 µl (6.19 mmol) of pyridine are dissolved in 3.0 ml DCM. Mol sieve is added and the mixture is stirred for 5 min. Then the tube is sealed by a septum and 10 ml oxygen are purged through. A solution of 250 mg (1.42 mmol) of 1-methylindazol-6-boronic acid in 5.0 ml THF is added dropwise in 6 h. The reaction mixture is stirred at r.t. for 16 h. The reaction mixture is diluted with diethylether and filtered. The organic layer is washed with 1N aq. HCl, dried and the solvent is evaporated. The residue is purified by chromatography on silica gel (PE/EtOAc) to give the title compound. Yield: 245 mg; LC (method 3): $t_R$=0.80 min; Mass spectrum (ESI$^+$): m/z=487 [M+H]$^+$.

The title compound may also be obtained from (6-(R)-(7-fluoro-4-hydroxyindan-1-yloxy)benzofuran-3-yl)acetic acid methyl ester and 6-bromo-1-methylindazole with copper iodide, N,N-dimethylgylcine (for example as HCl salt), and cesium carbonate in 1,4-dioxane at 100° C.

Step 2 (6-(R)-(7-Fluoro-4-(1-methyl-1H-indazol-6-yloxy)-indan-1-yloxy)benzofuran-3-yl)acetic acid The title compound is prepared from (6-(R)-(7-fluoro-4-(1-methyl-1H-indazol-6-yloxy)-indan-1-yloxy)benzofuran-3-yl)acetic acid methyl ester (product of step 1) following a procedure analogous to that described in step 7 of Intermediate 1. LC (method 3): $t_R$=0.53 min; Mass spectrum (ESI$^+$): m/z=473 [M+H]$^+$.

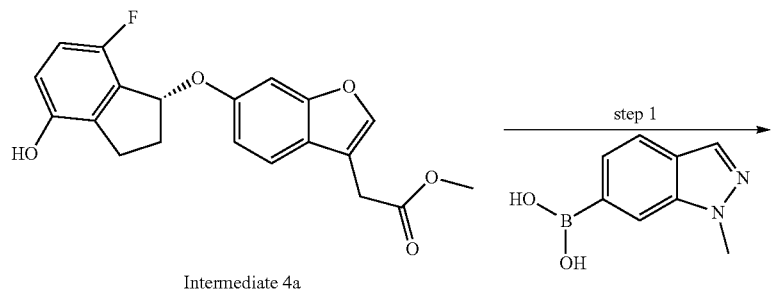

Intermediate 4a

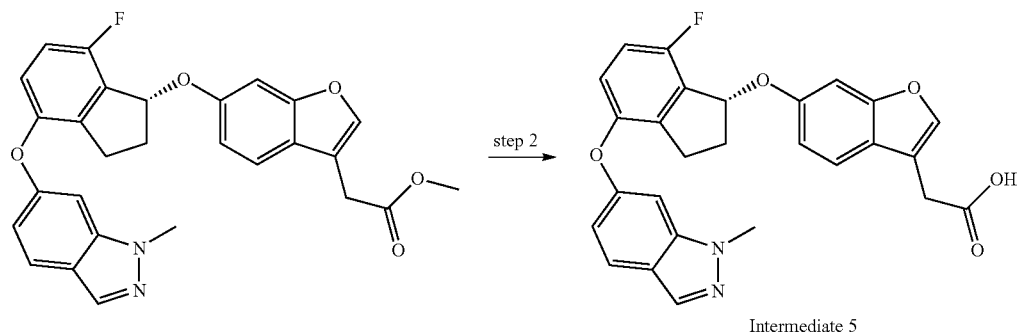

Intermediate 5

Intermediate 6

(6-(R)-(7-Fluoro-4-(4-methoxyphenoxy)-indan-1-yloxy)benzofuran-3-yl)acetic acid

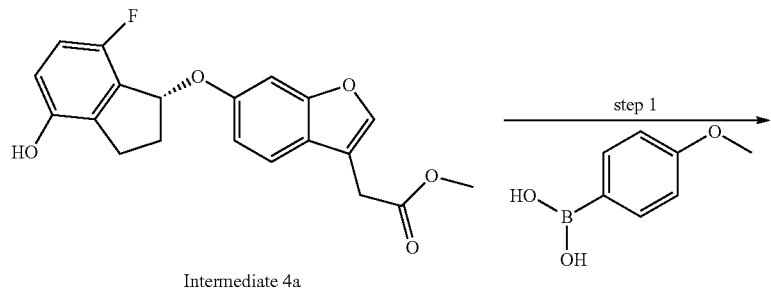

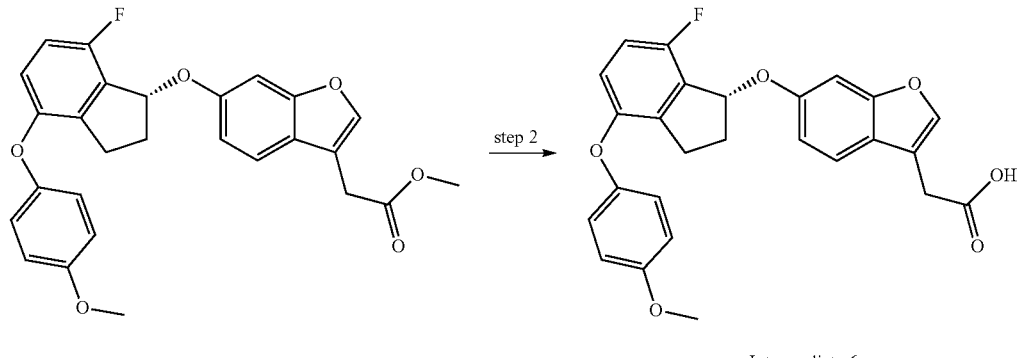

Step 1: (6-(R)-(7-Fluoro-4-(4-methoxyphenoxy)-indan-1-yloxy)benzofuran-3-yl)acetic acid methyl ester The title compound is prepared from (6-(R)-(7-fluoro-4-hydroxyindan-1-yloxy)benzofuran-3-yl)acetic acid methyl ester (Intermediate 4a) and 4-methoxyphenylboronic acid following a procedure analogous to that described in Step 1 of Intermediate 5. LC (method 3): $t_R$=0.87 min; Mass spectrum (ESI$^+$): m/z=463 [M+H]$^+$.

The title compound may also be obtained from (6-(R)-(7-fluoro-4-hydroxyindan-1-yloxy)benzofuran-3-yl)acetic acid methyl ester and 4-bromo-anisole with copper iodide, N,N-dimethylgylcine (for example as HCl salt), and cesium carbonate in 1,4-dioxane at 100° C.

Step 2: (6-(R)-(7-Fluoro-4-(4-methoxyphenoxy)-indan-1-yloxy)benzofuran-3-yl)acetic acid The title compound is prepared from (6-(R)-(7-fluoro-4-(4-methoxyphenoxy)-indan-1-yloxy)benzofuran-3-yl)acetic acid methyl ester (product of step 1) following a procedure analogous to that described in step 7 of Intermediate 1. LC (method 3): $t_R$=0.68 min; Mass spectrum (ESI$^+$): m/z=449 [M+H]$^+$.

Intermediate 7

(6-(R)-(4-Bromo-5-trifluoromethyl-indan-1-yloxy)benzofuran-3-yl)acetic acid

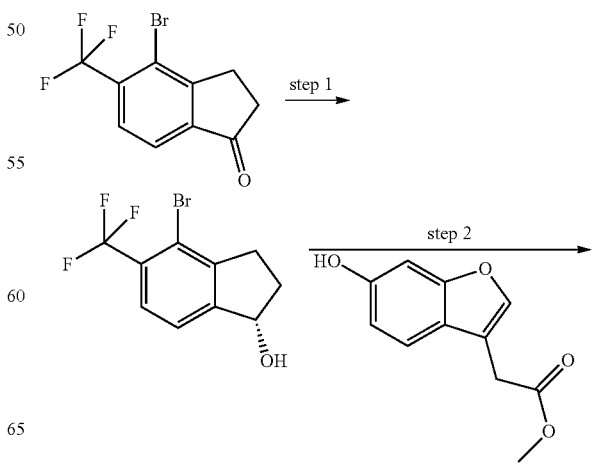

-continued

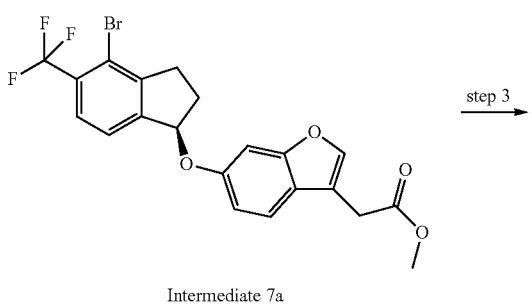

Intermediate 7a

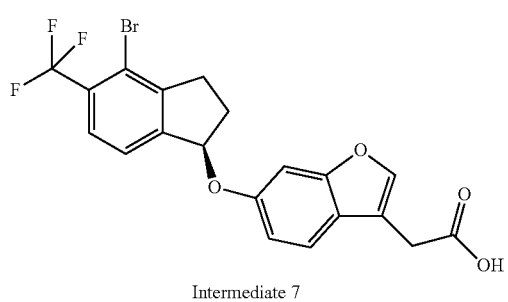

Intermediate 7

Step 1: (S)-4-Bromo-5-trifluoromethyl-indan-1-ol

Under argon atmosphere: 1.89 ml (13.6 mmol) TEA are dissolved in 15.0 ml DCM. Under ice cooling 0.59 ml (15.8 mmol) of formic acid are added. At r.t. 100 mg (3.58 mmol) of 4-bromo-5-trifluoromethyl-indan-1-one and 49.6 mg (0.07 mmol) of chloro{[(1S,2S)-(−)-2-amino-1,2-diphenylethyl](4-toluenesulfonyl)amido}-(mesitylene)-ruthenium(II) are added. The reaction mixture is stirred at r.t. for 48 h. The mixture is diluted with 20 ml 1N aq. HCl. The phases are separated. The aq. phase is washed with DCM. The combined organic layers are washed with brine, dried and the solvent is evaporated. The residue is chromatographed on silica gel (CH/EtOAc=75/25→50/50) to give the title compound. Yield: 1.03 g; LC (method 1): $t_R$=1.01 min.

Step 2 (Intermediate 7a): (6-(R)-(4-Bromo-5-trifluoromethyl-indan-1-yloxy)benzofuran-3-yl)acetic acid methyl ester Reaction under argon atmosphere: 800 mg (2.85 mmol) of (S)-4-bromo-5-trifluoromethyl-indan-1-ol (product of step 1) are dissolved in 15.0 ml THF. The mixture is cooled down in an ice/acetone bath. 763 mg (3.70 mmol) of (6-hydroxy-benzofuran-3-yl)acetic acid methyl ester and 1.1 ml (4.3 mmol) of tributylphosphane are added. Then a solution of 918 mg (3.98 mmol) of di-tert-butyl-azodicarboxylate in 3.0 ml THF is added dropwise over 45 min. The ice/acetone bath is removed and the reaction mixture is stirred for 45 min. 10 ml sat. NaHCO$_3$-solution are added and it is stirred for 10 min. The mixture is filtered through celite and the filtrate is washed with EtOAc. The organic layer is dried and the solvent is evaporated. The residue is purified by silica gel chromatography (CH/EtOAC=90/10→85/15) to give the title compound. Yield: 835 mg; LC (method 1): $t_R$=1.26 min.

Step 3: (6-(R)-(4-Bromo-5-trifluoromethyl-indan-1-yloxy)benzofuran-3-yl)acetic acid 130 mg (0.28 mmol) of (6-(R)-(4-bromo-5-trifluoromethyl-indan-1-yloxy)benzofuran-3-yl)acetic acid methyl ester (product of step 2) are dissolved in 1.0 ml THF and 1.0 ml MeOH. 250 µl (1 mmol) of 4N NaOH are added and the reaction mixture is stirred at r.t. for 3 h. The solvent is evaporated. The residue is diluted with water, acidified with 1N HCl and stirred for 1 h. The precipitate is filtered and dried in exsiccator. Yield: 121 mg; LC (method 1): $t_R$=1.18 min; Mass spectrum (ESI$^+$): m/z=455 [M+H]$^+$.

Intermediate 8

(6-(R)-(4-(4-(3-Methanesulfonyl-propoxy)-phenyl)-5-trifluoromethyl-indan-1-yloxy)benzofuran-3-yl)acetic acid

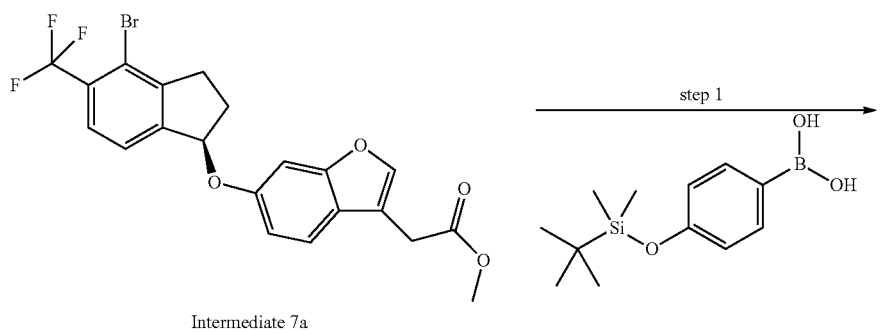

Intermediate 7a

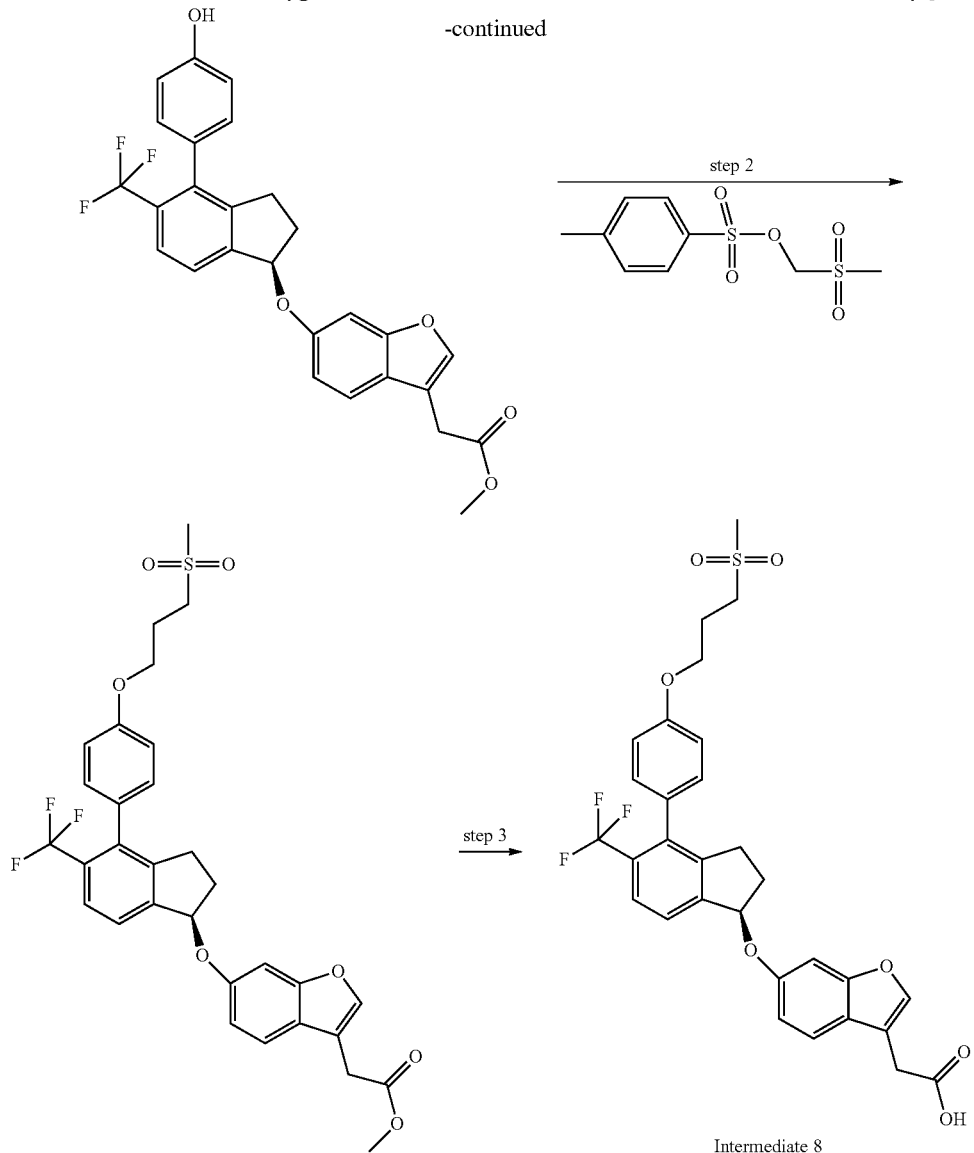

Intermediate 8

Step 1: (6-(R)-(4-(4-Hydroxyphenyl-5-trifluoromethyl-indan-1-1yloxy)benzofuran-3-yl)acetic acid methyl ester

Reaction under argon atmosphere: 613 mg (1.31 mmol) of (6-(R)-(4-bromo-5-trifluoromethyl-indan-1-yloxy)benzofuran-3-yl)acetic acid methyl ester (Intermediate 7a) and 362 mg (1.44 mmol) of 4-(tert-butyldimethylsilyloxy)phenylboronic acid are dissolved in 10.0 ml DMF. 1.76 ml (3.51 mmol) of 2N $NaCO_3$-solution are added. 105 mg (0.13 mmol) of (1,1'-bis(diphenylphosphino)ferrocene)dichloropalladium (II)-$CH_2Cl_2$-complex are added and the reaction mixture is stirred for 15 min at 120° C. in microwave. The solvent is evaporated. The residue is diluted with EtOAc and washed with water and brine. The organic layer is dried and the solvent is evaporated. The residue is purified by silica gel chromatography (CH/EtOAc=85/15→70/30) to give the title compound. Yield: 265 mg; LC (method 2): $t_R$=0.63 min; Mass spectrum ($ESI^+$): m/z=483 $[M+H]^+$.

Step 2: (6-(R)-(4-(4-(3-Methanesulfonyl-propoxy)-phenyl)-5-trifluoromethyl-indan-1-yloxy)benzofuran-3-yl)acetic acid methyl ester

The solution of 265 mg (0.55 mmol) of (6-(R)-(4-(4-hydroxyphenyl-5-trifluoromethyl-indan-1-1yloxy)benzofuran-3-yl)acetic acid methyl ester (product of step 1), 265 mg (0.91 mmol) of 3-(methylsulfonyl)propyl 4-methylbenzenesulfonate and 233 mg (0.71 mmol) of cesium carbonate in 3.0 ml DMF is stirred for 2 h at 60° C. The solvent is evaporated, the residue is dissolved in MeOH and purified by HPLC (reversed phase; $ACN/H_2O$/TFA) to give the title compound. Yield: 160 mg; LC (method 1): $t_R$=1.18 min; Mass spectrum ($ESI^+$): m/z=603 $[M+H]^+$.

The compound may also be obtained from (6-(R)-(4-bromo-5-trifluoromethyl-indan-1-yloxy)benzofuran-3-yl) acetic acid methyl ester (Intermediate 7a) and 2-[4-(3-methanesulfonyl-propoxy)-phenyl]-4,4,5,5-tetramethyl-[1,3,2] dioxaborolane or the corresponding boronic acid [e.g., prepared from 4-(4,4,5,5-tetramethyl-[1,3,2]dioxaborolan-2-yl)-phenol or the corresponding boronic acid and 3-(methylsulfonyl)propyl 4-methylbenzenesulfonate using Cs₂CO₃ or K₂CO₃ in DMF or NMP, or in analogy to Intermediate 23] applying the conditions described in Step 6 of Intermediate 1 or Step 1 of Intermediate 8.

Step 3: (6-(R)-(4-(4-(3-Methanesulfonyl-propoxy)-phenyl)-5-trifluoromethyl-indan-1-yloxy)benzofuran-3-yl)acetic acid The title compound is prepared from ((6-(R)-(4-(4-(3-methanesulfonyl-propoxy)-phenyl)-5-trifluoromethyl-indan-1-yloxy)benzofuran-3-yl)acetic acid methyl ester (product of step 2) following a procedure analogous to that described in Step 3 of Intermediate 7. LC (1): $t_R$=1.10 min; Mass spectrum (ESI⁺): m/z=606 [M+NH₄]⁺. The title compound may also be obtained using the carboxylic acid of the benzofuran-3-yl acetic ester derivative or a salt thereof for the coupling reaction, i.e. (6-(R)-(4-bromo-5-trifluoromethyl-indan-1-yloxy)benzofuran-3-yl)acetic acid. E.g., 2-[4-(3-methanesulfonyl-propoxy)-phenyl]-4,4,5,5-tetramethyl-[1,3,2]dioxaborolane or the corresponding boronic acid and (6-(R)-(4-bromo-5-trifluoromethyl-indan-1-yloxy)benzofuran-3-yl)acetic acid (e.g., as acid or the piperazinium or morpholinium salt) are coupled in the presence of K₂OC₃ and Pd(4-dimethylaminophenyl-di-tert-butylphosphine)₂Cl₂ in a mixture of n-propanol and water (1:2) at 90° C.

Intermediate 9

(6-(4-Morpholin-4-ylmethyl-5-trifluoromethyl-indan-1-yloxy)benzofuran-3-yl)acetic acid

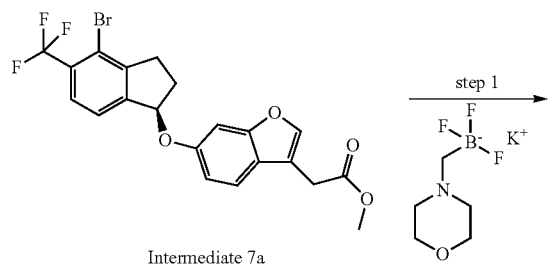

Intermediate 7a

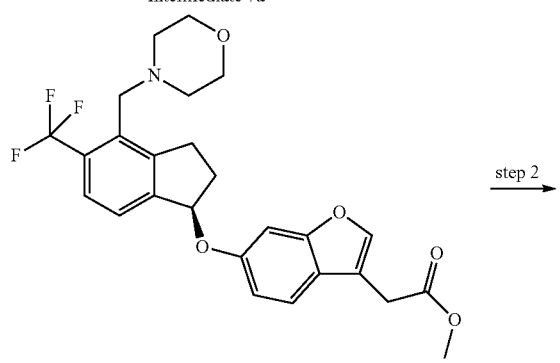

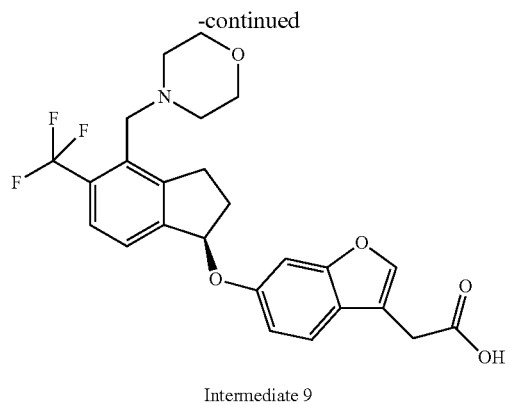

Intermediate 9

Step 1: (6-(4-Morpholin-4-ylmethyl-5-trifluoromethyl-indan-1-yloxy)benzofuran-3-yl)acetic acid methyl ester Reaction under argon atmosphere: 150 mg (0.32 mmol) of (6-(R)-(4-bromo-5-trifluoromethyl-indan-1-yloxy)benzofuran-3-yl)acetic acid methyl ester (Intermediate 7a) and 79.4 mg (0.38 mmol) of potassium(morpholin-4-yl)methyltrifluoroborate (alternatively, (morpholinium-4-ylmethyl)trifluoroborate may be used) are dissolved in 0.5 ml water and 5.0 ml THF. 312 mg (0.96 mmol) cesium carbonate, 51.8 mg (0.04 mmol) of (2-dicyclohexylphosphino-2',4',6'-tri-i-propyl-1,1'-biphenyl) and 5.0 mg (0.02 mmol) of palladium acetate are added. The reaction mixture is stirred at 100° C. for 3 h in microwave. The mixture is cooled down to r.t. and is diluted with water and EtOAc. The phases are separated. The aq. layer is extracted with EtOAc. The combined organic phases are washed with brine, dried and the solvent is evaporated. The residue is chromatographed on silica gel (CH/EtOAc=90/10→75/25) to give the title compound. Yield: 76 mg; LC (method 1): $t_R$=0.96 min.

Step 2: (6-(4-Morpholin-4-ylmethyl-5-trifluoromethyl-indan-1-yloxy)benzofuran-3-yl)acetic acid The title compound is prepared from (6-(4-morpholin-4-ylmethyl-5-trifluoromethyl-indan-1-yloxy)benzofuran-3-yl)acetic acid methyl ester (product of step 1) following a procedure analogous to that described in Step 3 of Intermediate 7. LC (method 1): $t_R$=0.87 min; Mass spectrum (ESI⁺): m/z=476 [M+H]⁺.

Intermediate 10

(6-(R)-(4-(2-Methyl-6,7-dihydro-4H-thiazolo(5,4-c)pyridin-5-ylmethyl)-5-trifluoromethyl-indan-1-yloxy)benzofuran-3-yl)acetic acid

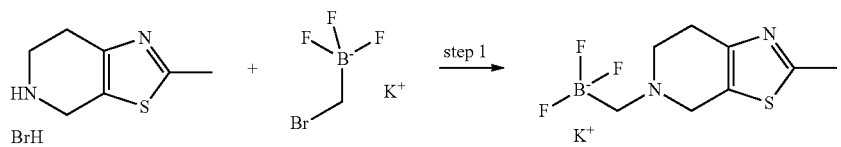

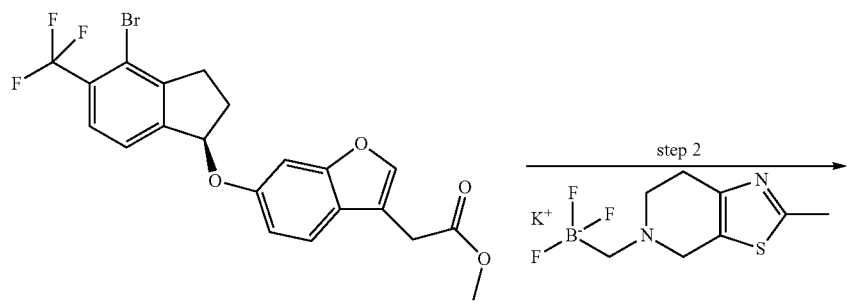

Intermediate 7a

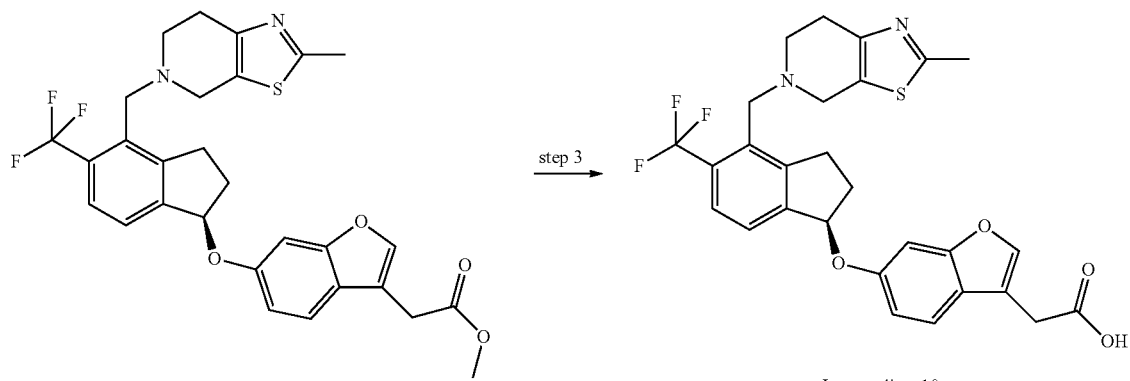

Intermediate 10

Step 1: Potassium trifluoro-((2-methyl-6,7-dihydro-4H-thiazolo(5,4-c)pyridin-5-yl)methyl)borate Reaction under nitrogen atmosphere: the mixture of 3.40 g (14.5 mmol) of 2-methyl-4,5,6,7-tetrahydrothiazolo(5,4-c)pyridinium bromide, 2.90 g (14.5 mmol) of bromomethyl potassium trifluoroborate, 240 mg (1.45 mmol) of potassium iodide and 2.00 g (14.5 mmol) of potassium carbonate in 30.0 ml THF is stirred for 4.5 h at reflux. The solvent is evaporated. The residue is diluted with 250 ml acetone and filtered. The precipitate is washed with 100 ml acetone and the solvent of the filtrate is evaporated. The residue is diluted with 30 ml diethylether and after 2 h it is filtered and the precipitate is dried. If the compound obtained is insufficiently pure the precipitate is chromatographed on silica gel (DCM/MeOH=96/4→80/20) to give the pure title compound possibly as internal ammonium salt. Yield: 1.0 g; LC (method 1): $t_R$=0.28 min; Mass spectrum (ESI$^+$): m/z=235 M$^-$.

Step 2: (6-(R)-(4-(2-Methyl-6,7-dihydro-4H-thiazolo(5,4-c)pyridin-5-ylmethyl)-5-trifluoromethyl-indan-1-yloxy)benzofuran-3-yl)acetic acid methyl ester The title compound is prepared from (6-(R)-(4-bromo-5-trifluoromethyl-indan-1-yloxy)benzofuran-3-yl)acetic acid methyl ester (Intermediate 7a) and potassium trifluoro-((2-methyl-6,7-dihydro-4H-thiazolo(5,4-c)pyridin-5-yl)methyl) borate (product of step 1; trifluoro-((2-methyl-6,7-dihydro-4H-thiazolo(5,4-c)pyridinium-5-yl)methyl)-borate may also be used) following a procedure analogous to that described in Step 1 of Intermediate 9. LC (method 1): $t_R$=1.02 min.

Step 3: (6-(R)-(4-(2-Methyl-6,7-dihydro-4H-thiazolo(5,4-c)pyridin-5-ylmethyl)-5-trifluoromethyl-indan-1-yloxy)benzofuran-3-yl)acetic acid The title compound is prepared from (6-(R)-(4-(2-methyl-6,7-dihydro-4H-thiazolo(5,4-c)pyridin-5-ylmethyl)-5-trifluoromethyl-indan-1-yloxy)benzofuran-3-yl)acetic acid methyl ester (product of step 1) following a procedure analogous to that described in Step 3 of Intermediate 7. LC (method 1): $t_R$=0.94 min; Mass spectrum (ESI$^+$): m/z=543 [M+H]$^+$.

Intermediate 11

(6-(R)-(4-Bromo-7-fluoroindan-1-yloxy)benzofuran-3-yl)acetic acid

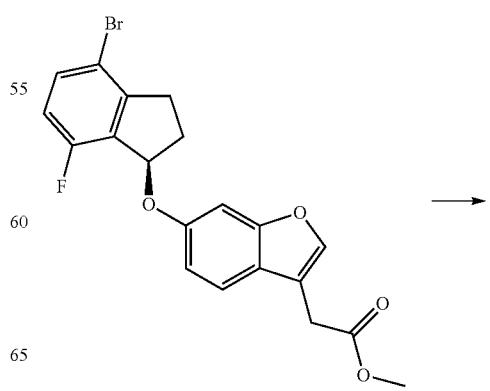

-continued

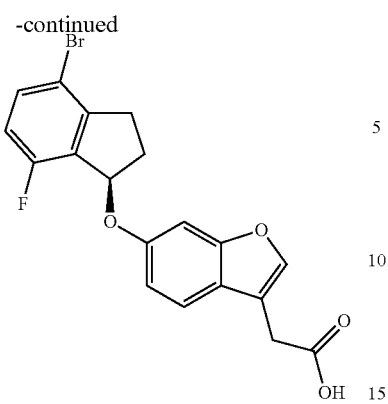

To the mixture of 1.00 g (2.39 mmol) of (6-(R)-(4-bromo-7-fluoroindan-1-yloxy)benzofuran-3-yl)acetic acid methyl ester (Intermediate 1a) and 10.0 ml MeOH are added 2.39 ml (9.54 mmol) of 4N aq. NaOH at r.t. The reaction mixture is stirred at 40° C. for 50 min. 2.39 ml 4N aq. HCl are added at r.t. and the mixture is stirred for 1 h at r.t. The precipitate is filtered, washed with water and dried in a vacuum drying cabinet. LC (method 4): $t_R$=4.43 min; Mass spectrum (ESI$^+$): m/z=405 [M+H]$^+$.

Intermediate 11 Morpholine (6-(R)-(4-Bromo-7-fluoroindan-1-yloxy)benzofuran-3-yl)acetic acid with morpholine

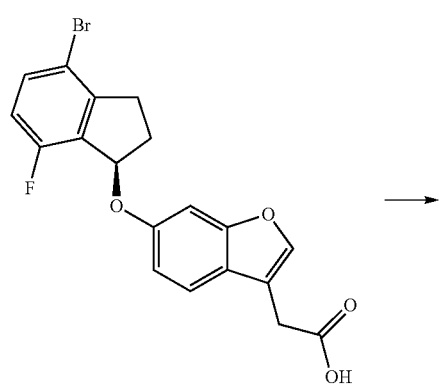

Under argon atmosphere: 2.94 g (7.26 mmol) of (6-(R)-(4-bromo-7-fluoroindan-1-yloxy)benzofuran-3-yl)acetic acid (Intermediate 11) are dissolved in 30.0 ml EtOH. The mixture is heated to 76° C. 0.64 ml (7.26 mmol) morpholine are added and it is stirred at 76° C. for 35 min. The mixture is cooled down to 36° C. and 30 ml isopropyl alcohol are added. Cooled down to r.t. The precipitate is filtered, washed with isopropyl alcohol and dried in a vacuum drying cabinet. Yield: 3.06 g; Mass spectrum (ESI$^+$): m/z=405 [M+H]$^+$.

Intermediate 11 Piperazine 6-(R)-(4-Bromo-7-fluoroindan-1-yloxy)benzofuran-3-yl)acetic acid with piperazine

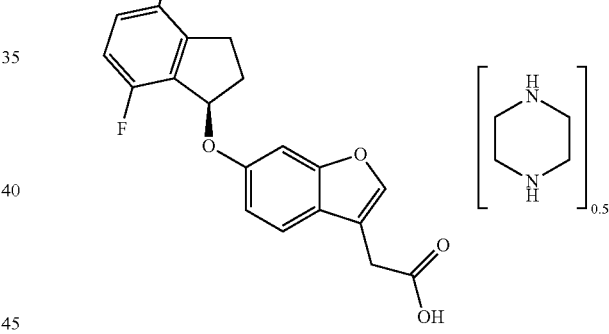

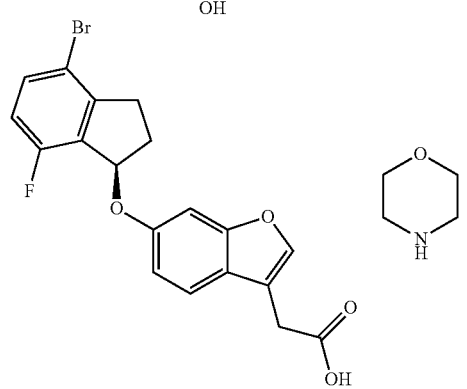

Reaction under argon atmosphere: 1.23 g (5.33 mmol) of (S)-4-bromo-7-fluoro-2,3-dihydro-1H-inden-1-ol (Intermediate 1, Step 3) and 1.00 g (4.85 mmol) of (6-hydroxy-benzofuran-3-yl)acetic acid methyl ester are dissolved in 8.0 ml THF. 1.87 ml (7.27 mmol) of tri-n-butylphosphine are added at r.t. The mixture is cooled down to −10° C. 1.51 ml (7.27 mmol) of diisopropylazodicarboxylate are added in 50 min at −10° C. At r.t. 4.85 ml (19.4 mmol) 4N aq. NaOH are added. The reaction mixture is cooled to 5° C. and 6.0 ml 4N aq. HCl are added. The mixture is extracted with isopropyl acetate, washed with brine, dried and the solvent is evaporated. The residue is diluted with 9.0 ml EtOH. The mixture is heated at 80° C. A solution of 0.17 g (1.94 mmol) of piperazine in 1.0 ml EtOH is added. The mixture is slowly cooled down to 0° C. and it is stirred at 0-5° C. for 16 h. The precipitate is filtered, washed with EtOH and dried in a vacuum drying cabinet. Yield: 1.33 g; LC (method 4): $t_R$=4.42 min; Mass spectrum (ESI$^+$): m/z=403 [M−H]$^−$.

Intermediate 12

(6-(R)-(7-Fluoro-4-(4-(3-hydroxy-3-methylbutoxy)-2,6-dimethylphenyl)-indan-1-yloxy)-2,3-dihydrobenzofuran-3-yl)acetic acid methyl ester

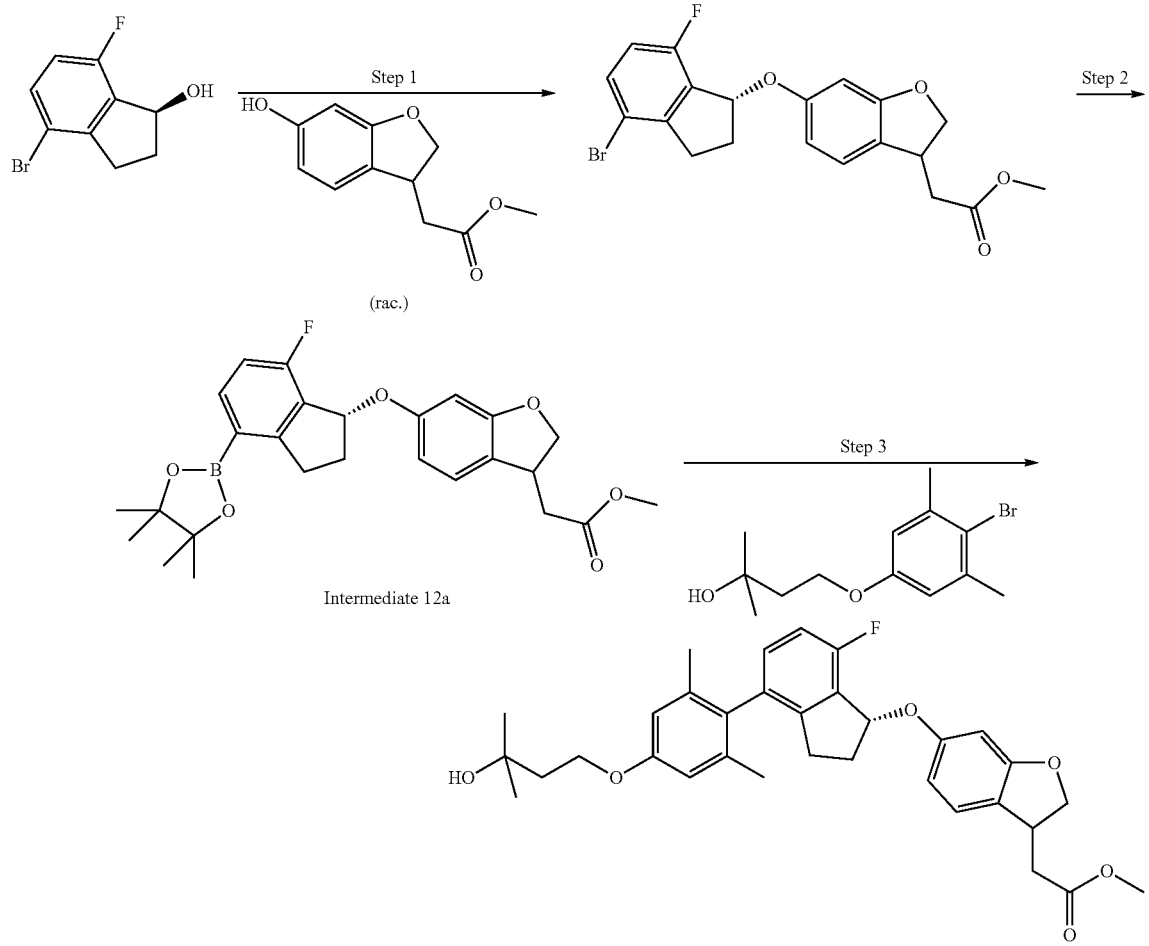

Step 1: (6-(R)-(4-Bromo-7-fluoroindan-1-yloxy)-2,3-dihydrobenzofuran-3-yl)acetic acid methyl ester 1.00 g (4.33 mmol) of (S)-4-bromo-7-fluoro-2,3-dihydro-1H-inden-1-ol (Intermediate 1, Step 3) is dissolved in 5.0 ml THF and cooled down in an ice/acetone bath. 0.95 g (4.56 mmol) of (6-hydroxy-2,3-dihydrobenzofuran-3-yl)acetic acid methyl ester and 1.35 ml (5.40 mmol) of tributylphosphane are added. A solution of 1.10 g (4.78 mmol) of di-tert-butyl-azodicarboxylate in 2.5 ml THF is added dropwise over 20 min. The reaction mixture is stirred for 45 min. 30 ml sat. NaHCO$_3$ solution is added and it is stirred for 10 min. The mixture is filtered through celite and washed with EtOAc. The organic layer is dried and the solvent is evaporated. The residue is chromatographed on silica gel (PE/EtOAc) to give the title compound. Yield: 1.40 g; LC (method 3): $t_R$=0.85 min.

Step 2 (Intermediate 12a): (6-(R)-(7-Fluoro-4-(4,4,5,5-tetramethyl-[1,3,2]dioxyborolan-2-yl)indan-1-yloxy)-2,3-dihydrobenzofuran-3-yl)acetic acid methyl ester Reaction under argon atmosphere: 1.40 g (3.32 mmol) of (6-(4-bromo-7-fluoroindan-1-yloxy)-2,3-dihydrobenzofuran-3-yl)acetic acid methyl ester (product of step 1) and 0.90 g (3.55 mmol) of bis-(pinacolato)diboron are dissolved in 10.0 ml 1,4-dioxane. 0.75 g (7.64 mmol) of potassium acetate and 50.0 mg (0.07 mmol) of 1,1'-bis(diphenylphosphino)ferrocene-dichloropalladium(II) are added and the reaction mixture is stirred at reflux for 4 h. The mixture is cooled to r.t and diluted with diethylether. The organic layer is washed with aq. NH$_4$Cl solution and the aq. layer is washed with diethylether. The combined organic layers are washed with brine, dried and the solvent is evaporated. The residue is chromatographed on silica gel (PE/EtOAc) to give the title compound. Yield: 1.39 g; LC (method 3): $t_R$=1.02 min; Mass spectrum (ESI$^+$): m/z=469 [M+H]$^+$.

Step 3: (6-(R)-(7-Fluoro-4-(4-(3-hydroxy-3-methylbutoxy)-2,6-dimethylphenyl)-indan-1-yloxy)-2,3-dihydrobenzofuran-3-yl)acetic acid methyl ester The title compound is prepared from (6-(R)-(7-fluoro-4-(4,4,5,5-tetramethyl-[1,3,2]dioxyborolan-2-yl)-indan-1-yloxy)-2,3-dihydrobenzofuran-3-yl)acetic acid methyl ester (product of step 2) and 4-(4-bromo-3,5-dimethylphenoxy)-2-methylbutan-2-ol following a procedure analogous to that described in Step 6 of Intermediate 1. LC (method 3): $t_R$=0.92 min. 4-(4-Bromo-3,5-dimethylphenoxy)-2-methylbutan-2-ol may be substituted with 4-(4-chloro-3,5-dimethylphenoxy)-2-methylbutan-2-ol and the 4,4,5,5-tetramethyl-[1,3,2]dioxaborolane derivative with the corresponding boronic acid to give the title compound under the same conditions.

The coupling may also be accomplished employing the conditions described or variants thereof (e.g., using Pd(4-dimethylaminophenyl-di-tert-butylphosphine)$_2$Cl$_2$ as the catalyst source) and the coupling partners with their opposite reactivity, i.e. 4-[3,5-dimethyl-4-(4,4,5,5-tetramethyl-[1,3,2] dioxaborolan-2-yl)-phenoxy]-2-methylbutan-2-ol or the corresponding boronic acid (Intermediate 23) and (6-(R)-(4-bromo-7-fluoroindan-1-yloxy)-2,3-dihydrobenzofuran-3-yl)acetic acid methyl ester.

Intermediate 13

(6-(R)-(7-Fluoro-4-(4-(2-hydroxy-2-methyl-propoxy)-2,6-dimethylphenyl)-indan-1-yloxy)-2,3-dihydrobenzofuran-3-yl)acetic acid methyl ester

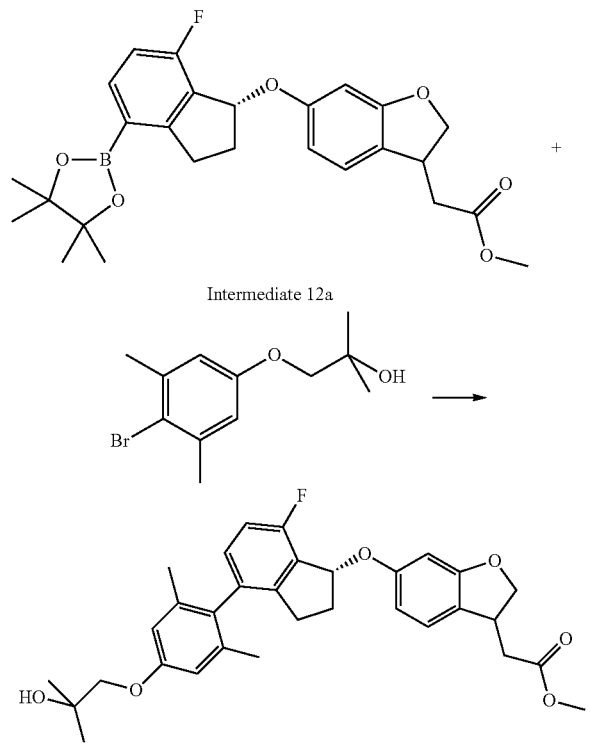

The title compound is prepared from (6-(R)-(7-fluoro-4-(4,4,5,5-tetramethyl-[1,3,2]dioxyborolan-2-yl)-indan-1-yloxy)-2,3-dihydrobenzofuran-3-yl)acetic acid methyl ester (Intermediate 12a) and 1-(4-bromo-3,5-dimethylphenoxy)-2-methyl-propan-2-ol following a procedure analogous to that described in Step 6 of Intermediate 1. LC (method 3): t$_R$=0.89 min.

1-(4-Bromo-3,5-dimethylphenoxy)-2-methyl-propan-2-ol may be substituted with 1-(4-chloro-3,5-dimethylphenoxy)-2-methyl-propan-2-ol and the 4,4,5,5-tetramethyl-[1,3,2]dioxaborolane derivative with the corresponding boronic acid to give the title compound under the same reaction conditions.

The coupling may also be accomplished employing the conditions described or variants thereof (e.g., using Pd(4-dimethylaminophenyl-di-tert-butylphosphine)$_2$Cl$_2$ as the catalyst source) and the coupling partners with their reversed reactivity, i.e. 1-[3,5-dimethyl-4-(4,4,5,5-tetramethyl-[1,3,2] dioxaborolan-2-yl)-phenoxy]-2-methylpropan-2-ol or the corresponding boronic acid and (6-(R)-(4-bromo-7-fluoroindan-1-yloxy)-2,3-dihydrobenzofuran-3-yl)acetic acid methyl ester.

Intermediate 14

(6-(R)-(4-(2,6-dimethyl-4-(tetrahydropyran-4-yloxy) phenyl)-7-fluoroindan-1-yloxy)-2,3-dihydrobenzofuran-3-yl)acetic acid methyl ester

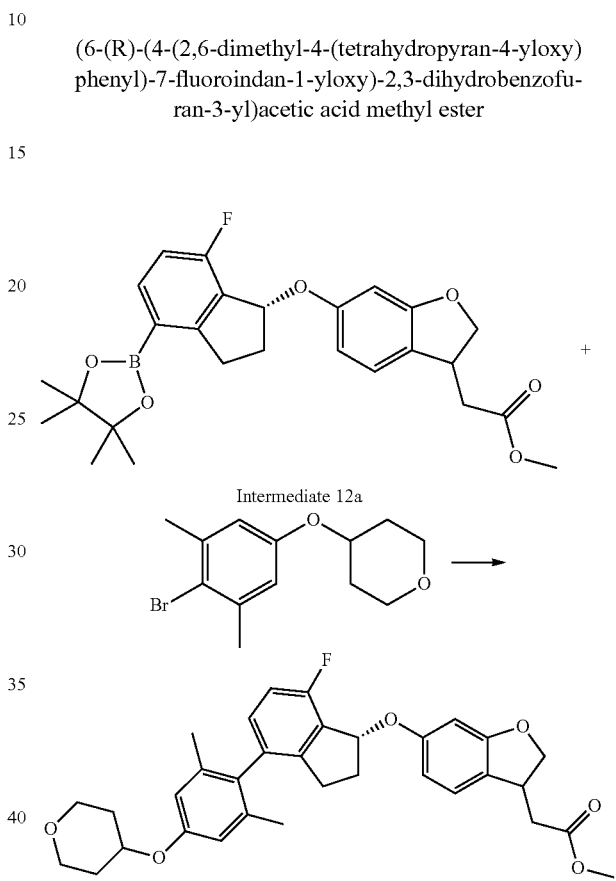

The title compound is prepared from (6-(R)-(7-fluoro-4-(4,4,5,5-tetramethyl-[1,3,2]dioxyborolan-2-yl)-indan-1-yloxy)-2,3-dihydrobenzofuran-3-yl)acetic acid methyl ester (Intermediate 12a) and 4-(4-bromo-3,5-dimethylphenoxy)-tetrahydropyran following a procedure analogous to that described in Step 6 of Intermediate 1. LC (method 3): t$_R$=0.98 min.

4-(4-Bromo-3,5-dimethylphenoxy)-tetrahydropyran may be substituted with 4-(4-chloro-3,5-dimethylphenoxy)-tetrahydropyran and the 4,4,5,5-tetramethyl-[1,3,2]dioxaborolane derivative with the corresponding boronic acid.

The coupling may also be accomplished employing the conditions described or variants thereof (e.g., using Pd(4-dimethylaminophenyl-di-tert-butylphosphine)$_2$Cl$_2$ as the catalyst source) and the coupling partners with their reversed reactivity, i.e. 4-[3,5-dimethyl-4-(4,4,5,5-tetramethyl-[1,3,2] dioxaborolan-2-yl)-phenoxy]-tetrahydropyran or the corresponding boronic acid and (6-(R)-(4-bromo-7-fluoroindan-1-yloxy)-2,3-dihydrobenzofuran-3-yl)acetic acid methyl ester.

Intermediate 15

(6-(R)-(7-Fluoro-4-hydroxyindan-1-yloxy)-2,3-dihydrobenzofuran-3-yl)acetic acid methyl ester

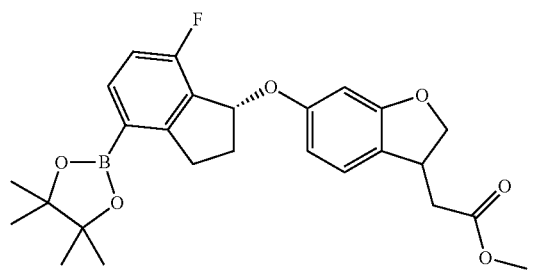

Intermediate 12a

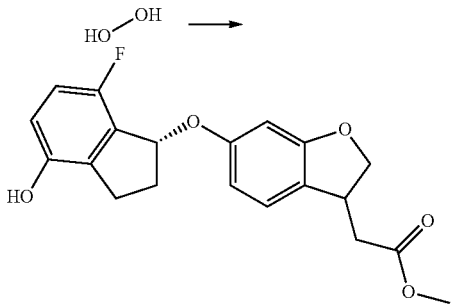

The title compound is prepared from (6-(R)-(7-fluoro-4-(4,4,5,5-tetramethyl-[1,3,2]-dioxyborolan-2-yl)-indan-1-yloxy)-2,3-dihydrobenzofuran-3-yl)acetic acid methyl ester (Intermediate 12a) and $H_2O_2$ following a procedure analogous to that described in Step 1 of Intermediate 4. LC (method 3): $t_R$=0.28 min.

The transformation may also be carried out using $H_2O_2$ (25 to 35% in water) in a mixture of EtOH and water (10:1) at 50° C.

Alternatively, the transformation may be accomplished with oxidants other than $H_2O_2$:
1. $NaBO_3*4H_2O$ in EtOH/acetic acid/$H_2O$ (8:1:1) at 20-30° C.; optionally, toluene or another co-solvent is added.
2. N-methyl-morpholine-N-oxide in MeCN at 80° C.

Intermediate 16

(6-(7-Fluoro-4-(1-methyl-1H-indazol-6-yloxy)-indan-1-yloxy)-2,3-dihydrobenzofuran-3-yl)acetic acid methyl ester

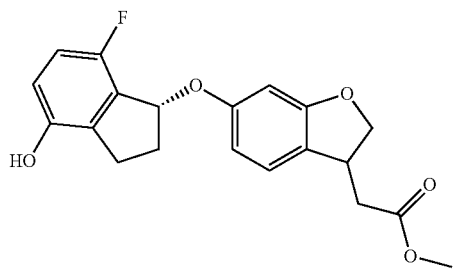

Intermediate 15

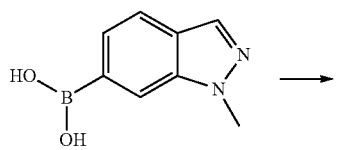

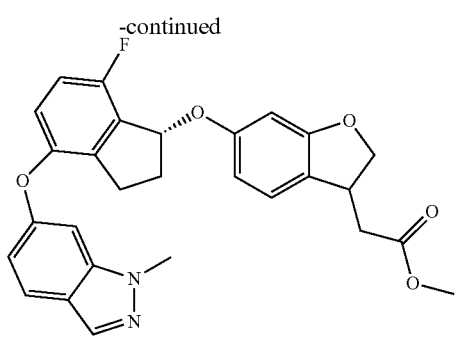

The title compound is prepared from (6-(R)-(7-fluoro-4-hydroxyindan-1-yloxy)-2,3-dihydrobenzofuran-3-yl)acetic acid methyl ester (Intermediate 15) and 1-methylindazol-6-boronic acid following a procedure analogous to that described in Step 1 of Intermediate 5. LC (method 3): $t_R$=0.77 min.

The title compound may also be obtained from (6-(R)-(7-fluoro-4-hydroxyindan-1-yloxy)-2,3-dihydrobenzofuran-3-yl)acetic acid methyl ester and 6-bromo-1-methylindazole (e.g., prepared from 4-bromo-2-fluoro-benzaldehyde and methylhydrazine in NMP at 100° C.] with copper iodide, N,N-dimethylgylcine (for example as HCl salt), and cesium carbonate in 1,4-dioxane at 100° C.

Intermediate 17

(6-(R)-(7-Fluoro-4-(4-methoxyphenoxy)-indan-1-yloxy)-2,3-dihydrobenzofuran-3-yl)acetic acid methyl ester

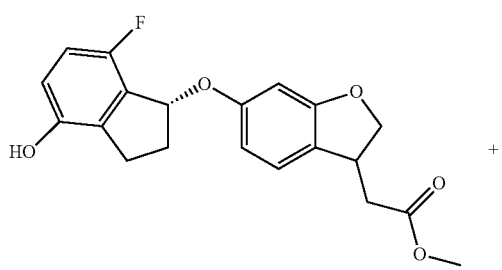

Intermediate 15

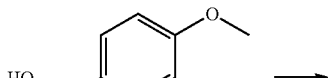

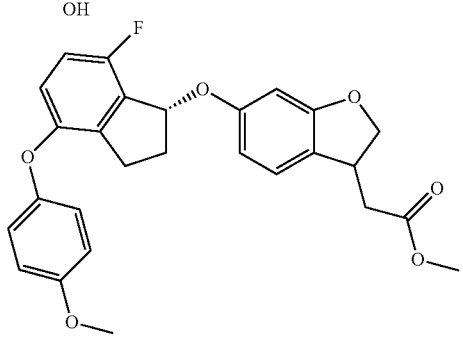

The title compound is prepared from (6-(R)-(7-fluoro-4-hydroxyindan-1-yloxy)-2,3-dihydrobenzofuran-3-yl)acetic acid methyl ester (Intermediate 15) and 4-methoxyphenylboronic acid following a procedure analogous to that described in Step 1 of Intermediate 5. LC (method 3): $t_R$=0.86 min.

The title compound may also be obtained from (6-(R)-(7-fluoro-4-hydroxyindan-1-yloxy)-2,3-dihydrobenzofuran-3-yl)acetic acid methyl ester and 4-bromo-anisole with copper iodide, N,N-dimethylgylcine (for example as HCl salt), and cesium carbonate in 1,4-dioxane at 100° C.

Intermediate 18

(6-(R)-(4-Bromo-5-trifluoromethyl-indan-1-yloxy)-2,3-dihydrobenzofuran-3-yl)acetic acid methyl ester

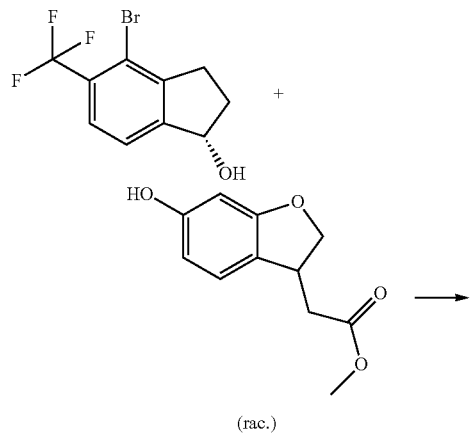

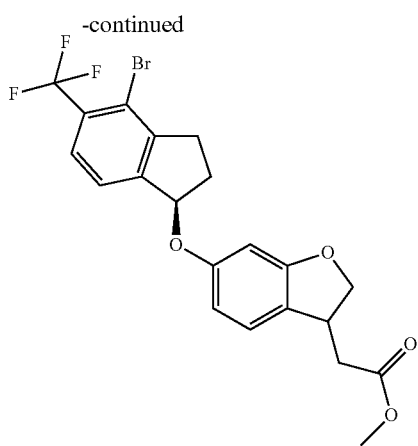

The title compound is prepared from (S)-4-bromo-5-trifluoromethyl-indan-1-ol (Intermediate 7, step 1) and (6-hydroxy-2,3-dihydrobenzofuran-3-yl)acetic acid methyl ester following a procedure analogous to that described in Step 2 of Intermediate 7. LC (method 1): $t_R$=1.26 min.

Intermediate 19

(6-(R)-(4-(4-(3-Methanesulfonyl-propoxy)-phenyl)-5-trifluoromethyl-indan-1-yloxy)-2,3-dihydrobenzofuran-3-yl)acetic acid methyl ester

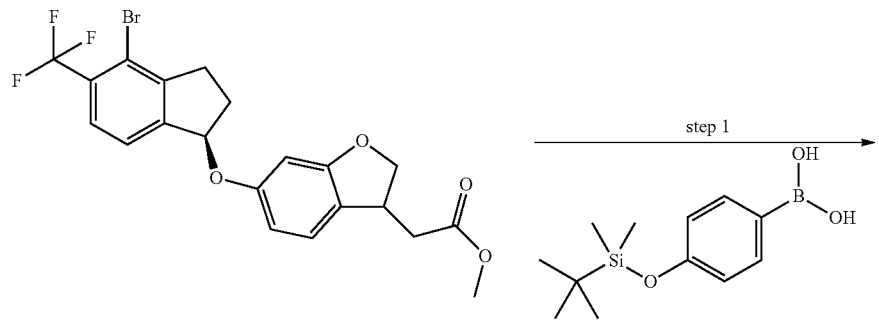

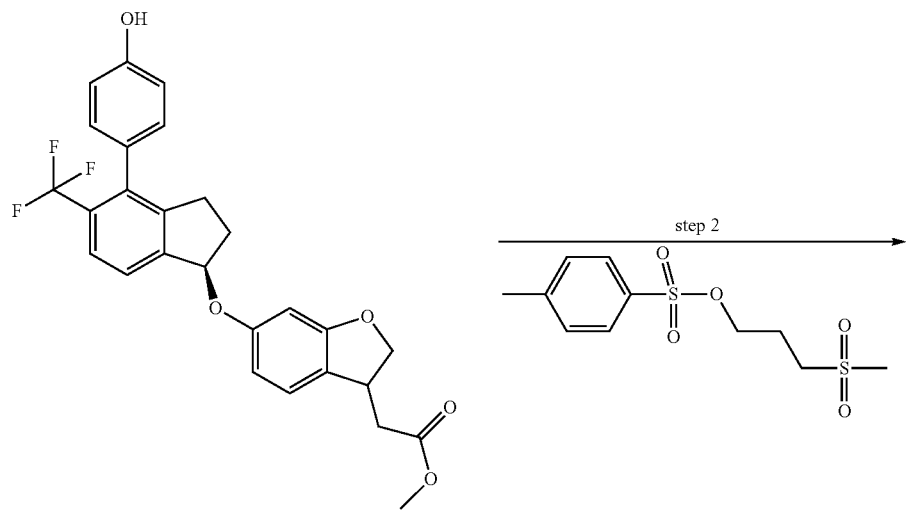

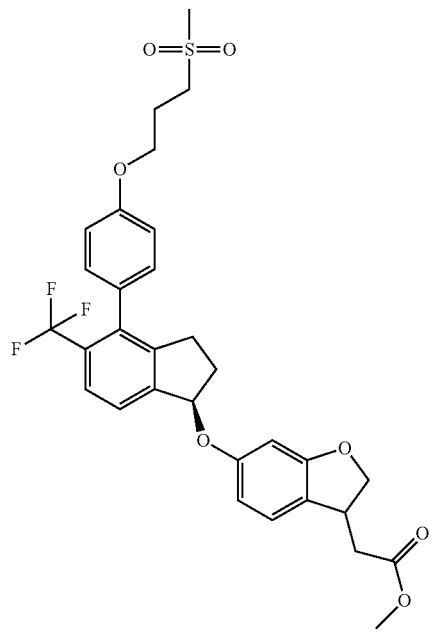

Step 1: (6-(R)-(4-(4-Hydroxyphenyl)-5-trifluoromethyl-indan-1-yloxy)-2,3-dihydrobenzofuran-3-yl)acetic acid methyl ester The title compound is prepared from (6-(R)-(4-bromo-5-trifluoromethyl-indan-1-yloxy)-2,3-dihydrobenzofuran-3-yl)acetic acid methyl ester (Intermediate 18) and 4-(tert-butyldimethylsilyloxy)phenylboronic acid following a procedure analogous to that described in Step 1 of Intermediate 8. LC (method 2): $t_R$=0.60 min; Mass spectrum (ESI$^+$): m/z=485 [M+H]$^+$.

Step 2: (6-(R)-(4-(4-(3-Methanesulfonyl-propoxy)-phenyl)-5-trifluoromethyl-indan-1-yloxy)-2,3-dihydrobenzofuran-3-yl)acetic acid methyl ester The title compound is prepared from (6-(R)-(4-(4-hydroxyphenyl)-5-trifluoromethyl-indan-1-yloxy)-2,3-dihydrobenzofuran-3-yl)acetic acid methyl ester (step 1) and 3-(methylsulfonyl)propyl 4-methylbenzenesulfonate following a procedure analogous to that described in Step 2 of Intermediate 8. LC (method 1): $t_R$=1.17 min; Mass spectrum (ESI$^+$): m/z=627 [M+Na]$^+$.

The compound may also be obtained from (6-(R)-(4-bromo-5-trifluoromethyl-indan-1-yloxy)-2,3-dihydrobenzofuran-3-yl)acetic acid methyl ester (Intermediate 18) and 2-[4-(3-methanesulfonyl-propoxy)-phenyl]-4,4,5,5-tetramethyl-[1,3,2]dioxaborolane or the corresponding boronic acid (e.g., prepared from 4-(4,4,5,5-tetramethyl-[1,3,2]dioxaborolan-2-yl)-phenol or the corresponding boronic acid and 3-(methylsulfonyl)propyl 4-methylbenzenesulfonate using $Cs_2CO_3$ or $K_2OC_3$ in DMF or NMP, or in analogy to Intermediate 23) applying the conditions described in Step 6 of Intermediate 1 or Step 1 of Intermediate 8.

Intermediate 20

(6-(R)-(4-Morpholin-4-ylmethyl-5-trifluoromethyl-indan-1-yloxy)-2,3-dihydrobenzo-furan-3-yl)acetic acid methyl ester

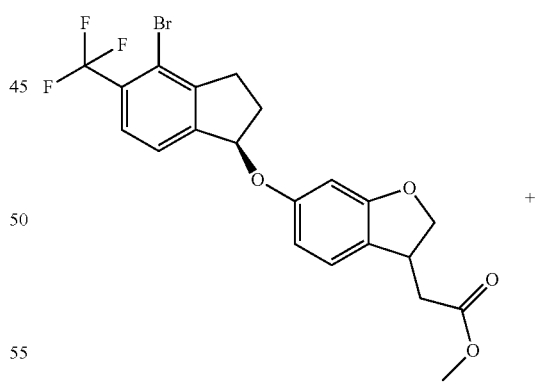

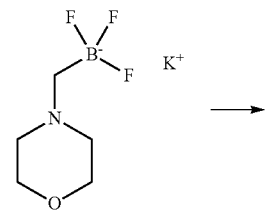

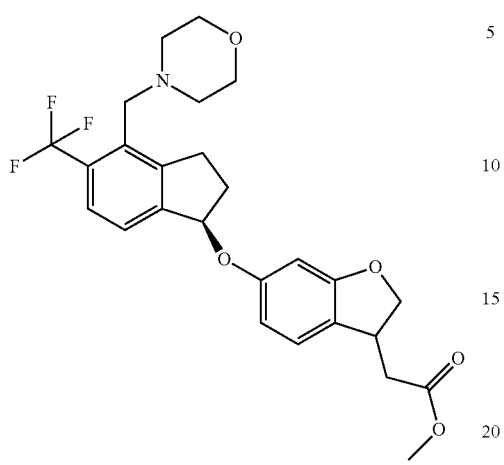

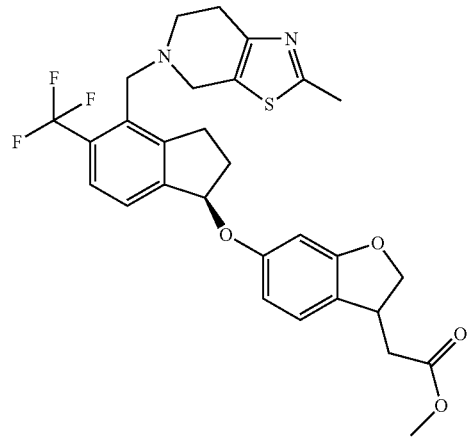

The title compound is prepared from (6-(R)-(4-bromo-5-trifluoromethyl-indan-1-yloxy)-2,3-dihydrobenzofuran-3-yl)acetic acid methyl ester (Intermediate 18) and potassium (morpholin-4-yl)methyltrifluoroborate (alternatively, (morpholinium-4-ylmethyl)trifluoroborate may be used) following a procedure analogous to that described in Step 1 of Intermediate 9. LC (method 1): $t_R$=0.94 min.

Intermediate 21

(6-(R)-(4-(2-Methyl-6,7-dihydro-4H-thiazolo(5,4-c)pyridin-5-ylmethyl)-5-trifluoromethyl-indan-1-yloxy)-2,3-dihydrobenzofuran-3-yl)acetic acid methyl ester The title compound is prepared from (6-(R)-(4-bromo-5-trifluoromethyl-indan-1-yloxy)-2,3-dihydrobenzofuran-3-yl)acetic acid methyl ester (Intermediate 18) and potassium trifluoro-((2-methyl-6,7-dihydro-4H-thiazolo(5,4-c)pyridin-5-yl)methyl)-borate (Intermediate 10, step 1; alternatively, trifluoro-(2-methyl-6,7-dihydro-4H-thiazolo(5,4-c)pyridinium-5-ylmethyl)borate may be used) following a procedure analogous to that described in Step 1 of Intermediate 9. LC (method 1): $t_R$=1.01 min.

Intermediate 22

(6-(4-Bromo-7-fluoroindan-1-yloxy)-2,3-dihydrobenzofuran-3-yl)acetic acid methyl ester

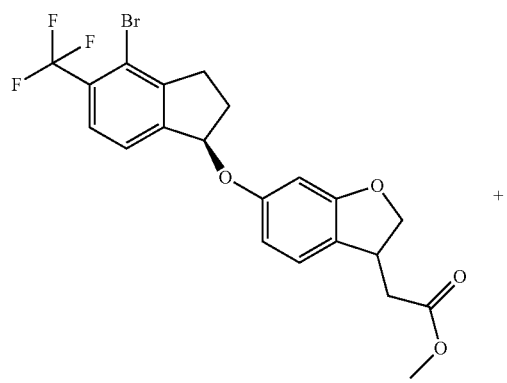

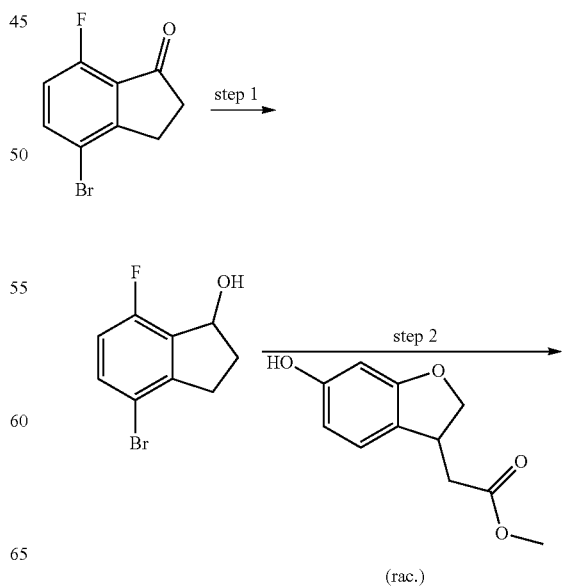

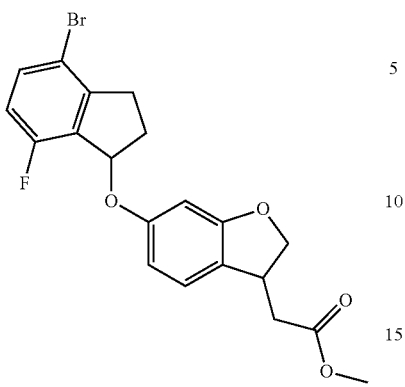

Step 1: 4-Bromo-7-fluoroindan-1-ol

Reaction under argon atmosphere: to a mixture of 1.69 g (43.7 mmol) of sodium borohydride in 120 ml isopropyl alcohol is added 20.0 g (87.3 mmol) of 4-bromo-7-fluoro-1-indanone portionwise. The reaction mixture is stirred at r.t. for 2 h. The solvent is evaporated. To the residue are added 100 g ice and 200 ml 1N aq. HCl. The mixture is extracted with EtOAc. The combined organic layers are washed with brine, dried and the solvent is evaporated. The residue is chromatographed on silica gel (PE/EtOAc=100/0→70/30) to give the title compound. Yield: 15.4 g; LC (method 4): $t_R$=3.05 min; Mass spectrum (ESI$^+$): m/z=213 [M+H—H$_2$O]$^+$.

Step 2: (6-(4-Bromo-7-fluoroindan-1-yloxy)-2,3-dihydrobenzofuran-3-yl)acetic acid methyl ester Reaction under argon atmosphere: to a solution of 15.3 g (66.3 mmol) of 4-bromo-7-fluoroindan-1-ol (product of step 1) and 11.0 g (53.0 mmol) of (6-hydroxy-2,3-dihydrobenzofuran-3-yl)acetic acid methyl ester in 60.0 ml DCM are added 29.7 ml (116 mmol) of tributylphosphine. 24.4 ml (116 mmol) of diisopropylazodicarboxylate are added dropwise and under cooling in an ice/EtOH bath at 5° C.-15° C. over 20 min. It is stirred at r.t. for 1 h. The solvent is evaporated and the residue is chromatographed on silica gel (PE/EtOAc=100/0→95/5) to give the title compound. Yield: 16.9 g; LC (method 4): $t_R$=4.84 min; Mass spectrum (ESI$^+$): m/z=421 [M+H]$^+$.

Intermediate 23

4-(4-Boronic acid-3,5-dimethylphenoxy)-2-methylbutan-2-ol

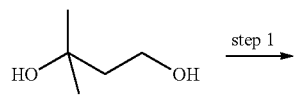

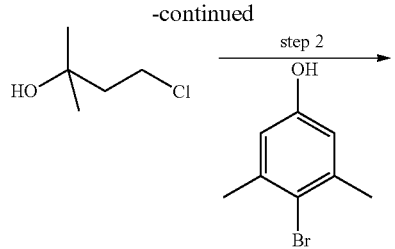

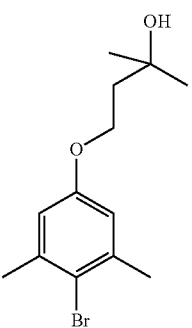

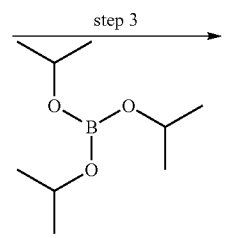

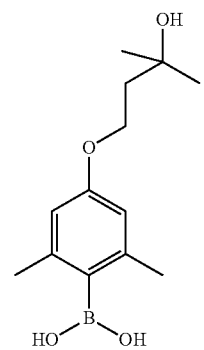

Step 1: 4-Chloro-2-methylbutan-2-ol 10.0 g (96.0 mmol) 3-methyl-1,3-butandiol is dissolved in 30.0 ml toluene and 10.7 g (106 mmol) TEA is added. The funnel is rinsed with 10.0 ml toluene. The mixture is heated to 80° C. and a mixture of 11.6 g (101 mmol) methanesulfonyl chloride and 3.00 ml toluene is added. After complete addition, the funnel is rinsed with 7.00 ml toluene and the reaction mixture is heated to reflux for approx. 3 h. After full conversion (GC) the mixture is cooled to 20° C. and 40.0 ml water is added. Stirring is continued for a short period and the aqueous phase is separated. Then, approx. 10 ml of the organic phase is distilled off in vacuum. The crude toluene solution of the product is used for the next step.

Step 2: 4-(4-Bromo-3,5-dimethylphenoxy)-2-methylbutan-2-ol 10.0 g (49.7 mmol) 4-bromo-3,5-dimethylphenol and 10.3 g (74.6 mmol) K$_2$OC$_3$ are mixed with 20.0 mL N-methylpyrrolidone and heated to 100° C. 37.0 g (64.7 mmol) 4-chloro-2-methylbutan-2-ol (toluene solution from step 1) is added and the funnel is rinsed with 10.0 ml N-methylpyrrolidone. The reaction mixture is heated to 115° C. for approx. 3 h before 30.0 ml of the solvent is distilled off in vacuum. After full conversion the mixture is cooled to 20° C., 60.0 ml water is added and stirring is continued for 5 min. 90.0 ml n-heptane is added and the aqueous phase is separated. The organic phase is washed twice with 30.0 ml water. 20.0 ml solvent is distilled off and the mixture is cooled to 15° C. Seeds are added and stirring is continued for 1 h at 15° C. The suspension is cooled to −15° C. and stirred for 1 h. The product is filtered off, washed twice with cooled n-heptane and dried. Yield: 11.7 g; TLC: R$_f$=0.40 (silicagel, EtOAc:PE 2:8).

Step 3: 4-(4-boronic acid-3,5-dimethylphenoxy)-2-methylbutan-2-ol

Under argon, 20.0 g (69.6 mmol) of 4-(4-bromo-3,5-dimethylphenoxy)-2-methylbutan-2-ol (product of step 2) are dissolved in 200 ml THF and cooled down to −67° C. 42.8 g (143 mmol) of a solution of n-hexyl lithium in hexan (2.3 mol/l) are added dropwise over 1 h. The mixture is stirred at −67° C. for 10 min, then water is added and the mixture is dissolved with ACN. 24.0 ml (104 mmol) of triisopropyl borate are added dropwise at −70° C. and it is stirred for 1 h. 120 ml water are added dropwise and the mixture is stirred 2 h to reach r.t. The mixture is acidified with 4N aq. HCl to reach pH 2.2. The phases are separated and the organic layer is washed with brine. 160 ml toluene is added and 180 ml solvent is evaporated. 60 ml toluene are added and the mixture is stirred for 16 h at 10° C. The mixture is cooled down to 0° C. and filtered. The precipitate is washed with toluene and then dried at 45° C. Yield: 13.9 g; TLC: r$_f$=0.20 (silicagel, EtOAc:CH 4:6); Mass spectrum (ESI$^+$): m/z=251 [M−H]$^−$. Intermediate 23 may be reacted in coupling reactions with compounds of general formula I and V, more specifically in coupling reactions with Intermediates 11 or 22, or with the compounds of Examples 12-21 and 26-34.

Examples 1 to 11

For Examples 1 to 6, 0.16 mmol of starting material are dissolved in 2.0 ml EtOH. 500 μl (0.50 mmol) of a 1N aq. KOH solution are added and the reaction mixture is stirred at r.t. for 16 h. The reaction mixture is diluted with EtOAc and 500 μl of a 1N aq. HCl are added. Brine is added and then the phases are separated. The organic layer is dried and the solvent is evaporated. The residue is chromatographed on silica gel (PE/EtOAc) to give the title compound. Yields are generally in the range of 70 to 80%.

The following compounds are prepared analogously to Examples 1-6.

For Examples 7 to 10 is used 1.0 ml THF and 1.0 ml MeOH as solvent and 3.8 eq of 4N NaOH as base. The mixture is diluted with water and acidified with 1N aq. HCl. The mixture is stirred for 1 h at r.t. The precipitate is filtered and dried. For Example 11 is used MeOH as solvent and 2.5 eq of 4N NaOH as base. The reaction mixture is stirred at 40° C.-45° C. for 70 min. MeOH is evaporated. The residue is acidified with 100 ml 4N aq. HCl and extracted with tert-butylmethylether. The combined organic layers are washed with brine, dried and the solvent is evaporated.

| Ex. | starting material | product | Mass spectrum | t$_R$ (min) (method) |
|---|---|---|---|---|
| 1 | Intermediate 12 | | 535 (M + H)$^+$ | 0.69 (3) |
| 2 | Intermediate 13 | | 521 (M + H)$^+$ | 0.64 (3) |
| 3 | Intermediate 14 | | 533 (M + H)$^+$ | 0.77 (3) |

-continued

| Ex. | starting material | product | Mass spectrum | $t_R$ (min) (method) |
|---|---|---|---|---|
| 4 | Intermediate 15 | | 345 (M + H)⁺ | 0.89 (1) |
| 5 | Intermediate 16 | | 475 (M + H)⁺ | 0.48 (3) |
| 6 | Intermediate 17 | | 451 (M + H)⁺ | 0.65 (3) |
| 7 | Intermediate 18 | | 457 (M + H)⁺ | 1.17 (1) |

| Ex. | starting material | product | Mass spectrum | $t_R$ (min) (method) |
|---|---|---|---|---|
| 8 | Intermediate 19 | 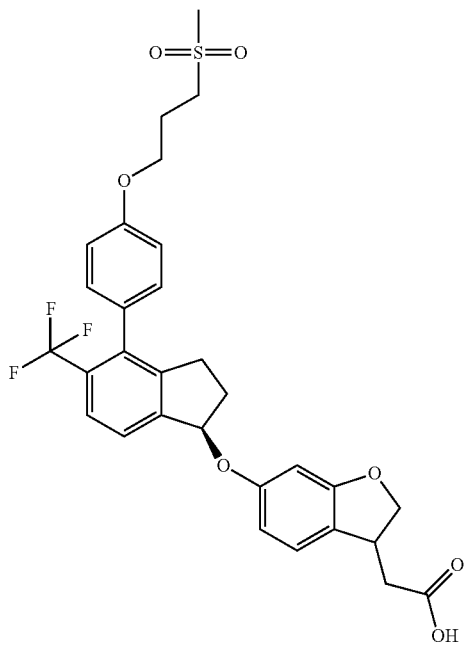 [SMILES: CS(=O)(=O)CCCOc1ccc(-c2c(C(F)(F)F)ccc3c2CC[C@H]3Oc2ccc3c(c2)OCC3CC(=O)O)cc1] | 608 $(M + NH_4)^+$ | 1.08 (1) |
| 9 | Intermediate 20 | 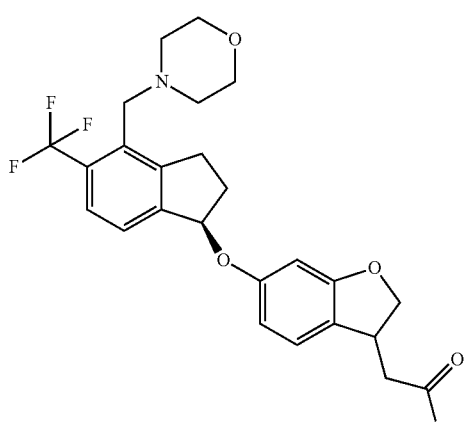 | 478 $(M + H)^+$ | 0.84 (1) |
| 10 | Intermediate 21 | 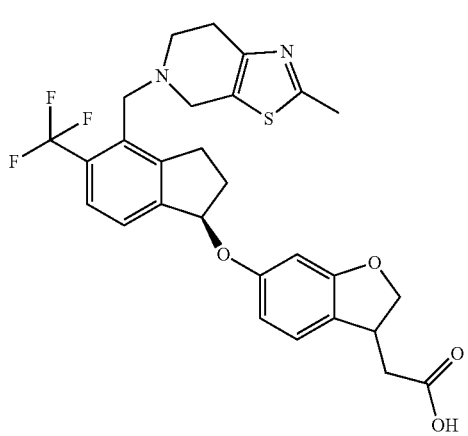 [SMILES: Cc1nc2c(s1)CN(Cc1c(C(F)(F)F)ccc3c1CC[C@H]3Oc1ccc3c(c1)OCC3CC(=O)O)CC2] | 545 $(M + H)^+$ | 0.92 (1) |

-continued

| Ex. | starting material | product | Mass spectrum | $t_R$ (min) (method) |
|---|---|---|---|---|
| 11 | Intermediate 22 | (structure) | 407 (M + H)+ | 4.36 (4) |

Examples 12 to 21

(6-(R)-(4-Bromo-7-fluoroindan-1-yloxy)-2-(3S)-dihydrobenzofuran-3-yl)acetic acid

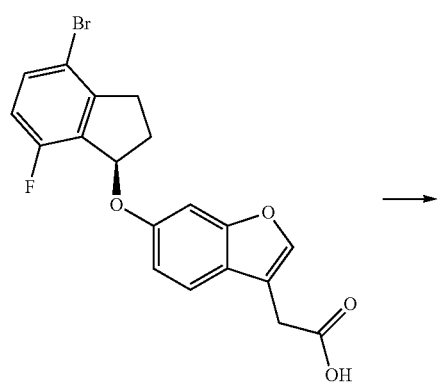

| Ex. | Catalyst | Mol % | Ligand | Mol % | Title compound area (%) | dr |
|---|---|---|---|---|---|---|
| 13 | [Ru(p-cymene)Cl₂]₂ | 1 | Josi-Phos | 1 | 98.6 | 10:90 |
| 14 | [Ru(p-cymene)Cl₂]₂ | 1 | Josi-Phos | 2 | 97.3 | 10:90 |
| 15 | Rh(COD)₂OTf | 2 | Josi-Phos | 2 | 97.5 | 6:94 |
| 16 | Rh(COD)₂OTf | 2 | S,S-Et-Ferrotane | 2 | 85.4 | 6:94 |
| 17 | [Ru(p-cymene)Cl₂]₂ | 1 | S,S-Et-Ferrotane | 2 | 97.7 | 39:61 |
| 18 | Rh(COD)₂OTf | 2 | Solvias J-13-1 | 2 | 97.8 | 83:17 |
| 19 | [Ru(p-cymene)Cl₂]₂ | 1 | Solvias J-13-1 | 2 | 99 | 91:9 |
| 20 | Rh(COD)₂OTf | 2 | cataCXiumT2 | 2 | 91 | 86:14 |
| 21 | [Ru(p-cymene)Cl₂]₂ | 1 | cataCXiumT2 | 2 | 99 | 5.5:94.5 |

Example 22

(6-(R)-(4-Bromo-7-fluoroindan-1-yloxy)-2-(3S)-dihydrobenzofuran-3-yl)acetic acid with morpholine

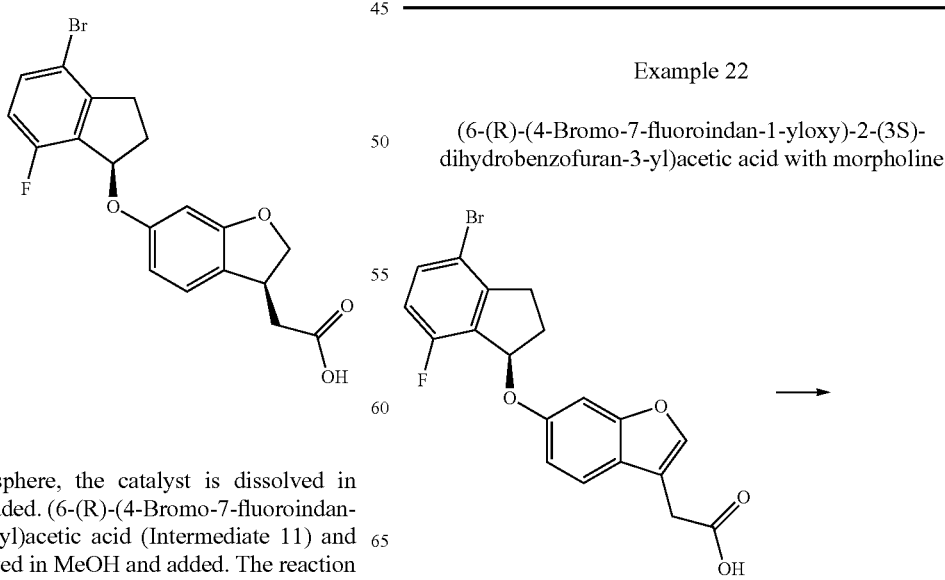

Under argon atmosphere, the catalyst is dissolved in MeOH, the ligand is added. (6-(R)-(4-Bromo-7-fluoroindan-1-yloxy)benzofuran-3-yl)acetic acid (Intermediate 11) and 1.2 eq TEA are dissolved in MeOH and added. The reaction mixture is hydrogenated at 25 bar and 50° C. for 20 h.

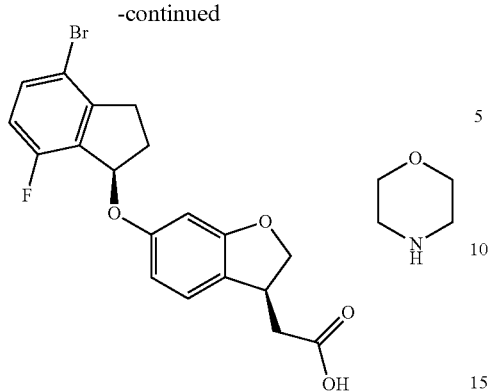

10.0 g (24.7 mmol) [6-((R)-4-bromo-7-fluoroindan-1-yloxy)benzofuran-3-yl]acetic acid is dissolved in 10 ml MeOH and 57.8 mg (0.12 mmol) bis(1,5-cyclooctadiene) rhodium(I) trifluoromethanesulfonate and 64.5 mg (0.12 mmol) (S)-1-[(R)-2-(di-2-furylphosphino)ferrocenyl]-ethyl-di-tert.-butylphosphine is added. 2.35 ml (12.0 mmol) NaOMe (30% sol. in MeOH) is added and the mixture is hydrogenated at 13.8 bar and r.t. until hydrogen uptake has ceased. The reaction mixture is filtered through a pad of charcoal and the solvent is distilled off at elevated temperature in vacuum until formation of a suspension. Then, 100 ml EtOAc is added and 25% of the solvent is distilled off. 25 ml water and 25 ml EtOAc is added and the organic phase is separated. The aqueous phase is extracted with 25 ml EtOAc and the combined organic phases are evaporated to half of the volume. The resulting suspension is co-distilled with 150 ml isopropanol in total and 2.58 ml (30.0 mmol) morpholine is added at 75° C. The mixture is cooled and seeds and 30 ml isopropanol is added. After stirring overnight at r.t. the suspension is cooled in an ice bath. The product is filtered off, washed with cold isopropanol (2×12 ml) and dried. Yield: 9.43 g; $R_f$=0.40 (PE/EtOAc/AcOH=6/4/0.1); Mass spectrum (ESI): m/z=405 [M−H]−.

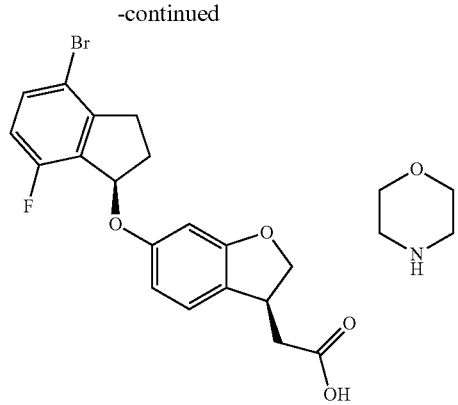

To 310 mg (0.50 mmol) of [Ru(p-cymene)Cl$_2$]$_2$ and 270 mg (0.50 mmol) of Josi-Phos are added 20.0 ml MeOH. The mixture is purged for 10 min with argon. A solution of 10.07 g (68.4 mmol) of (6-(R)-(4-bromo-7-fluoroindan-1-yloxy) benzofuran-3-yl)acetic acid (Intermediate 11) in 50.0 ml THF and 3.5 ml (25 mmol) TEA are added to the mixture. The reaction mixture is purged for 20 min with argon. The reaction mixture is hydrogenated at 50° C. and with 10 bar for 34 h. The reaction mixture is cooled to r.t. and filtered. The filtrate is extracted with 2N aq. HCl and isopropylacetate. The combined organic layers are washed with brine, dried and the solvent is evaporated. The residue is diluted with 150 ml EtOH and 35 ml of the solvent are evaporated. The mixture is heated to reflux and 2.2 ml (25 mmol) of morpholine are added. The mixture is slowly cooled down to r.t. and 35 ml EtOH are evaporated. The mixture is stirred at r.t. for 48 h. The precipitate is filtered and washed with EtOH. The precipitate is dried at 50° C. to give the title compound. Yield: 9.4 g; LC (method 4): $t_R$=4.37 min; Mass spectrum (ESI+): m/z=405 [M−H]−.

Example 23

(6-(R)-(4-Bromo-7-fluoroindan-1-yloxy)-2-(3S)-dihydrobenzofuran-3-yl)acetic acid with morpholine

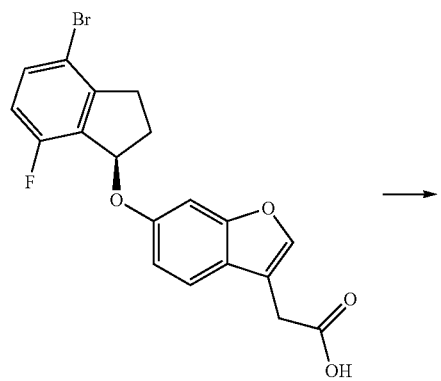

Example 24

(6-(R)-(4-Bromo-7-fluoroindan-1-yloxy)-2-(3S)-dihydrobenzofuran-3-yl)acetic acid with morpholine

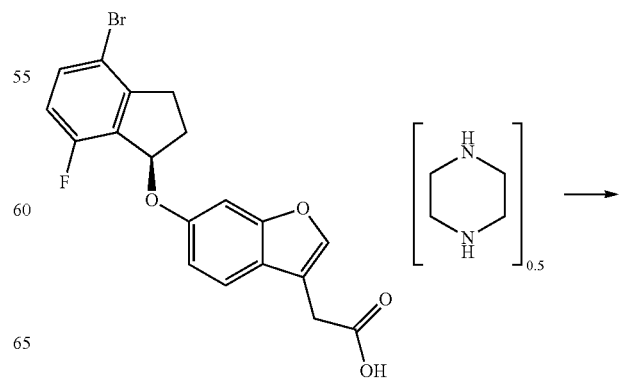

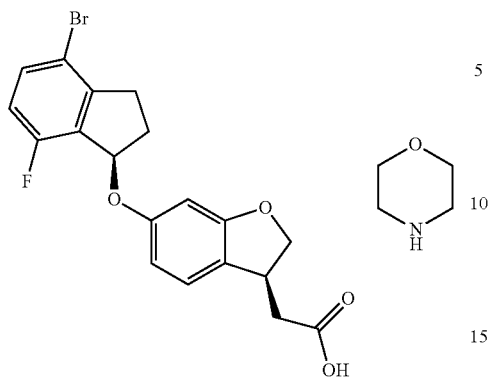

To 54.6 mg (0.09 mmol) of [Ru(p-cymene)Cl₂]₂ and 48.1 mg (0.09 mmol) of Josi-Phos are added 10.0 ml MeOH. The mixture is purged for 10 min with argon. A solution of 2.00 g (2.23 mmol) of (6-(R)-(4-bromo-7-fluoroindan-1-yloxy)benzofuran-3-yl)acetic acid with piperazine (Intermediate 11 piperazine) in 20.0 ml MeOH and 2.5 ml (18 mmol) TEA are added to the mixture. The reaction mixture is purged for 15 min with argon. The reaction mixture is hydrogenated at 50° C. and with 10 bar for 1.5 h. 400 mg activated carbon is added, the mixture is stirred at reflux for 10 min, then the mixture is filtered. The solvent is evaporated. The residue is extracted with 4N aq. HCl and isopropylacetate. The combined organic layers are washed with brine, dried and the solvent is evaporated. The residue is diluted with 20 ml isopropyl alcohol and heated to reflux. 0.40 ml (4.46 mmol) of morpholine are added, then the mixture is cooled down to r.t. 5.0 ml isopropyl alcohol are added and the mixture is cooled down to 0° C.-5° C. and stirred for 1 h at this temperature. The precipitate is filtered and washed with isopropyl alcohol. The precipitate is dried at 50° C. to give the title compound. Yield: 1.24 g; LC (method 4): t_R=4.37 min; Mass spectrum (ESI⁺): m/z=405 [M−H]⁻.

Example 25

(6-(R)-(4-Bromo-7-fluoroindan-1-yloxy)-2-(3S)-dihydrobenzofuran-3-yl)acetic acid with piperazine

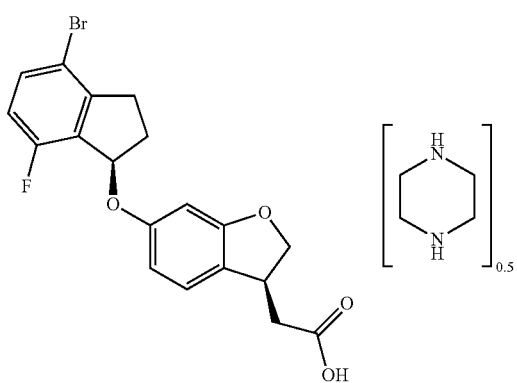

To 6.8 mg (0.01 mmol) of [Ru(p-cymene)Cl₂]₂ and 6.0 mg (0.01 mmol) of Josi-Phos are added 10.0 ml MeOH. The mixture is purged for 10 min with argon. A solution of 2.00 g (2.23 mmol) of (6-(R)-(4-bromo-7-fluoroindan-1-yloxy)benzofuran-3-yl)acetic acid with piperazine (Intermediate 11 piperazine) in 20.0 ml MeOH and 2.5 ml (18 mmol) TEA are added to the mixture. The reaction mixture is purged for 15 min with argon. The reaction mixture is hydrogenated at 50° C. and with 10 bar for 6 h. 400 mg activated carbon is added, the mixture is stirred at reflux for 10 min, then the mixture is filtered. The solvent is evaporated. The residue is diluted with 50 ml isopropyl alcohol, 29 ml solvent are evaporated. The mixture is stirred for 16 h at r.t. The precipitate is filtered and washed with isopropyl alcohol. The precipitate is dried at 50° C. to give the title compound. Yield: 1.18 g; LC (method 4): t_R=4.37 min; Mass spectrum (ESI⁺): m/z=405 [M−H]⁻.

Examples 26 to 34

(6-(R)-(4-Bromo-7-fluoroindan-1-yloxy)-2-(3S)-dihydrobenzofuran-3-yl)acetic acid

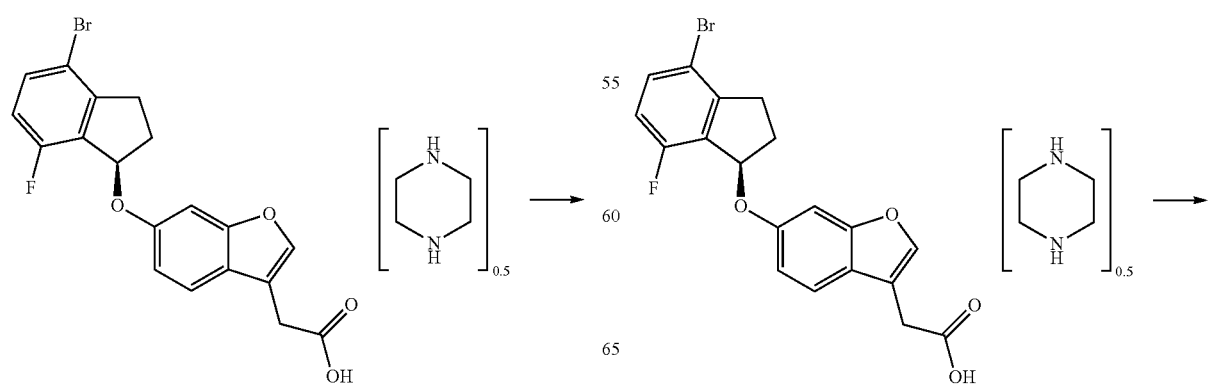

-continued

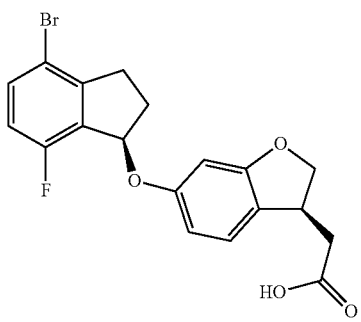

Under argon atmosphere, the catalyst is dissolved in MeOH, the ligand is added. (6-(R)-(4-Bromo-7-fluoroindan-1-yloxy)benzofuran-3-yl)acetic acid with piperazine (Intermediate 11 piperazine) and 1.2 eq TEA are dissolved in MeOH and added. The reaction mixture is hydrogenated at 25 bar and 50° C. for 20 h.

| Ex. | Catalyst | Mol % | Ligand | Mol % | Title compound area (%) | dr |
|---|---|---|---|---|---|---|
| 26 | [Ru(p-cymene)Cl₂]₂ | 2 | Josi-Phos | 2 | 98.4 | 6:94 |
| 27 | [Ru(p-cymene)Cl₂]₂ | 2 | Josi-Phos | 4 | 93.5 | 6:94 |
| 28 | Rh(COD)₂OTf | 4 | Josi-Phos | 4 | 73 | 7:93 |
| 29 | Rh(COD)₂OTf | 4 | S,S-Et-Ferrotane | 4 | 19 | ND |
| 30 | [Ru(p-cymene)Cl₂]₂ | 2 | S,S-Et-Ferrotane | 4 | 0 | ND |
| 31 | Rh(COD)₂OTf | 4 | Solvias J-13-1 | 4 | 18 | ND |
| 32 | [Ru(p-cymene)Cl₂]₂ | 2 | Solvias J-13-1 | 4 | 99.4 | 92:8 |
| 33 | Rh(COD)₂OTf | 4 | cataCXiumT2 | 4 | 1 | ND |
| 34 | [Ru(p-cymene)Cl₂]₂ | 2 | cataCXiumT2 | 4 | 99.6 | 5:95 |

Examples 35 to 52

(6-(R)-(4-Bromo-7-fluoroindan-1-yloxy)-2-(3S)-dihydrobenzofuran-3-yl)acetic acid with morpholine

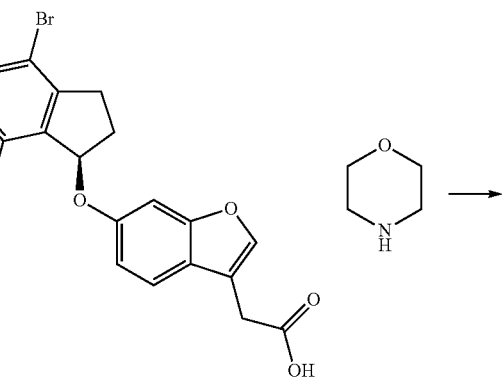

Under argon atmosphere, the catalyst is dissolved, the ligand is added. (6-(R)-(4-Bromo-7-fluoroindan-1-yloxy)benzofuran-3-yl)acetic acid with morpholine (Intermediate 11 morpholine) is dissolved and added. The reaction mixture is hydrogenated at 25 bar and 50° C. For Ex. 61 and Ex. 62: The reaction mixture is hydrogenated at 50° C. and with 12 bar for 1.5 h. 50 ml isopropyl alcohol are added and 30 ml of the solvent are evaporated. 200 mg activated carbon is added, the mixture is stirred at reflux for 10 min, then the mixture is filtered. The mixture is stirred for 16 h at r.t. and then for 1 h at 0° C.-5° C. The precipitate is filtered and washed with isopropyl alcohol. The precipitate is dried at 50° C.

| Ex. | Catalyst | Mol % | Ligand | Mol % | solvent | Title compound area (%) | dr |
|---|---|---|---|---|---|---|---|
| 35 | [Ru(p-cymene)Cl₂]₂ | 0.25 | Josi-Phos | 1 | MeOH | 100 | 9:91 |
| 36 | Rh(COD)₂OTf | 0.5 | Josi-Phos | 1 | MeOH | 100 | 7:93 |
| 37 | [Ru(p-cymene)Cl₂]₂ | 0.125 | Josi-Phos | 0.5 | MeOH | 100 | 9:91 |
| 38 | Rh(COD)₂OTf | 0.25 | Josi-Phos | 0.5 | MeOH | 100 | 7:93 |
| 39 | [Ru(p-cymene)Cl₂]₂ | 0.0625 | Josi-Phos | 0.25 | MeOH | 79 | ND |
| 40 | Rh(COD)₂OTf | 0.125 | Josi-Phos | 0.25 | MeOH | 100 | 8:92 |
| 41 | [Ru(p-cymene)Cl₂]₂ | 0.03125 | Josi-Phos | 0.125 | MeOH | 40 | ND |
| 42 | Rh(COD)₂OTf | 0.0625 | Josi-Phos | 0.125 | MeOH | 93 | 8:92 |
| 43 | [Ru(p-cymene)Cl₂]₂ | 0.25 | Josi-Phos | 1 | DCM | 100 | 5:95 |
| 44 | Rh(COD)₂OTf | 0.5 | Josi-Phos | 1 | DCM | 100 | 11:89 |
| 45 | [Ru(p-cymene)Cl₂]₂ | 0.125 | Josi-Phos | 0.5 | DCM | 100 | 5:95 |
| 46 | Rh(COD)₂OTf | 0.25 | Josi-Phos | 0.5 | DCM | 100 | 11:89 |

-continued

| Ex. | Catalyst | Mol % | Ligand | Mol % | solvent | Title compound area (%) | dr |
|---|---|---|---|---|---|---|---|
| 47 | [Ru(p-cymene)Cl$_2$]$_2$ | 0.0625 | Josi-Phos | 0.25 | DCM | 13 | ND |
| 48 | Rh(COD)$_2$OTf | 0.125 | Josi-Phos | 0.25 | DCM | 94 | ND |
| 49 | [Ru(p-cymene)Cl$_2$]$_2$ | 0.03125 | Josi-Phos | 0.125 | DCM | 2 | ND |
| 50 | Rh(COD)$_2$OTf | 0.0625 | Josi-Phos | 0.125 | DCM | 77 | ND |
| 51 | [Ru(p-cymene)Cl$_2$]$_2$ | 0.1 | Josi-Phos | 0.2 | MeOH | 67 | ND |
| 52 | Rh(COD)$_2$OTf | 4 | Josi-Phos | 4 | MeOH | 39 | ND |

Examples 53 to 63

Intermediates 1 to 11 can be hydrogenated in analogy to Examples 12 to 52, based on the following general method:

To 0.6 mg (1.0 μmol) of [Ru(p-cymene)Cl$_2$]$_2$ and 2.0 mg (3.8 μmol) of Josi-Phos is added 1.0 ml MeOH. The mixture is purged for 10 min with argon. A solution of 0.19 mmol of Intermediate in 2.0 ml MeOH and 1 eq of K$_2$OC$_3$ is added to the mixture. The reaction mixture is purged for 15 min with argon. The reaction mixture is hydrogenated at 50° C. and with 24 bar for 14 h. The reaction mixture is cooled to r.t. and purified by chromatography (reversed phase; ACN/H$_2$O) to give the title compound. Yields are generally in the range of 60 to 80%.

| Ex. | starting material | product | Mass spectrum | t$_R$ (min) (method) | de (area %) |
|---|---|---|---|---|---|
| 53 | Intermediate 1 | | 535 (M + H)$^+$ | 4.41 (4) | 88.65 |
| 54 | Intermediate 2 | | 521 (M + H)$^+$ | 4.35 (4) | 87.73 |
| 55 | Intermediate 3 | | 533 (M + H)$^+$ | 4.60 (4) | 89.67 |

-continued

| Ex. | starting material | product | Mass spectrum | $t_R$ (min) (method) | de (area %) |
|---|---|---|---|---|---|
| 56 | Intermediate 4 | | 345 $(M + H)^+$ | 3.38 (4) | 89.35 |
| 57 | Intermediate 5 | | 475 $(M + H)^+$ | 4.16 (4) | 92.07 |
| 58 | Intermediate 6 | | 451 $(M + H)^+$ | 4.42 (4) | 86.07 |
| 59 | Intermediate 7 | | 457 $(M + H)^+$ | 4.64 (4) | 89.45 |

-continued

| Ex. | starting material | product | Mass spectrum | $t_R$ (min) (method) | de (area %) |
|---|---|---|---|---|---|
| 60 | Intermediate 8 | | 608 $(M + NH_4)^+$ | 4.14 (4) | 78.97 |
| 61 | Intermediate 9 | | 478 $(M + H)^+$ | 4.25 (4) | 95.00 |
| 62 | Intermediate 10 | | 545 $(M + H)^+$ | 4.57 (4) | 94.49 |

| Ex. | starting material | product | Mass spectrum | $t_R$ (min) (method) | de (area %) |
|---|---|---|---|---|---|
| 63 | Intermediate 11 | (structure shown) | 407 $(M + H)^+$ | 4.36 (4) | 92.37 |

Examples 53, 54, and 55 are also obtained via coupling {(S)-6-[(R)-4-bromo-7-fluoroindan-1-yloxy]-2,3-dihydrobenzofuran-3-yl}-acetic acid (Example 63) or {(S)-6-[(R)-7-fluoro-4-(4,4,5,5-tetramethyl-[1,3,2]dioxaborolan-2-yl)-indan-1-yloxy]-2,3-dihydrobenzofuran-3-yl}-acetic acid with the corresponding coupling partner bearing a metal or pseudo-metal group, e.g., boronic acid or ester, or a leaving group, e.g., Cl or Br, at the carbon to be coupled. Accordingly, Example 53 is obtained from, e.g., 4-[3,5-dimethyl-4-(4,4,5,5-tetramethyl-[1,3,2]dioxaborolan-2-yl)-phenoxy]-2-methylbutanol or the corresponding boronic acid (Intermediate 23) and [(S)-6-((R)-4-bromo-7-fluoroindan-1-yloxy)-2,3-dihydrobenzofuran-3-yl]-acetic acid (e.g., as acid or the piperazinium or morpholinium salt) or from, e.g., 4-(4-bromo-3,5-dimethylphenoxy)-2-methylbutanol and {(S)-6-[(R)-7-fluoro-4-(4,4,5,5-tetramethyl-[1,3,2]dioxaborolan-2-yl)-indan-1-yloxy]-2,3-dihydrobenzofuran-3-yl}-acetic acid (e.g., as acid or the piperazinium or morpholinium salt), as described below.

Example 53

((S)-6-{(R)-7-Fluoro-4-[4-(3-hydroxy-3-methylbutoxy)-2,6-dimethylphenyl]-indan-1-yloxy}-2,3-dihydrobenzofuran-3-yl)acetic acid

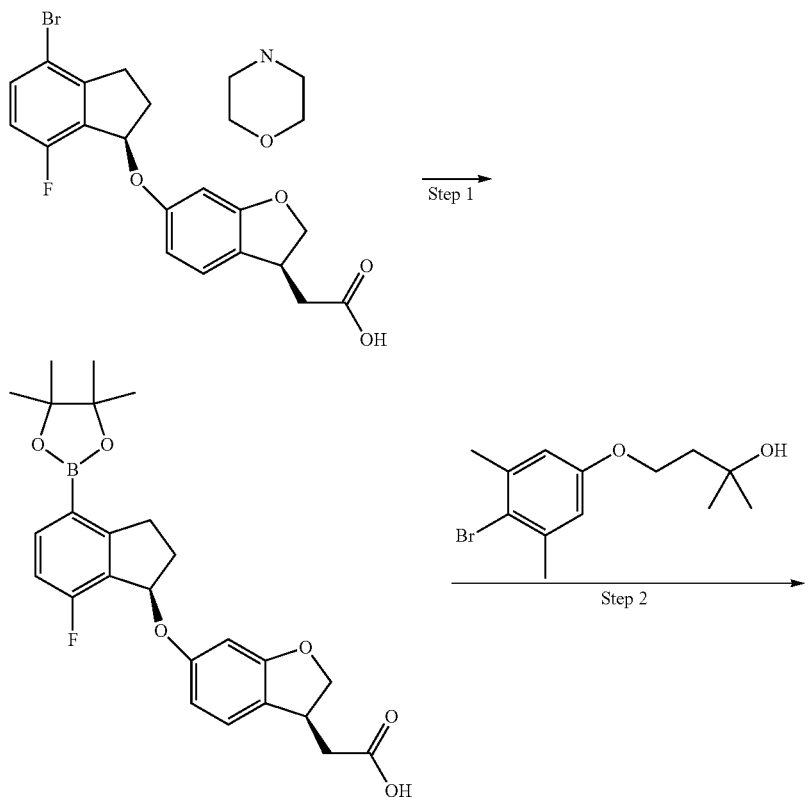

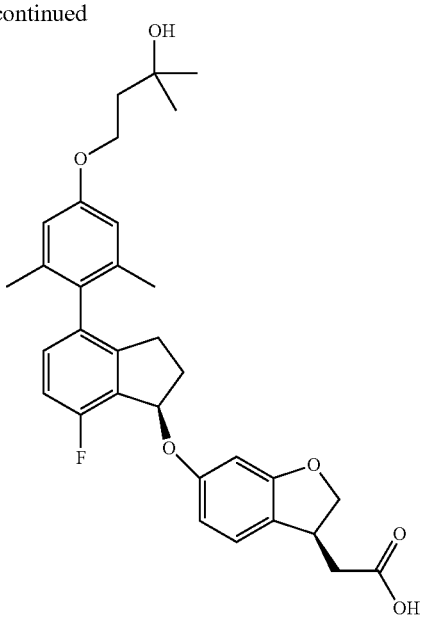

Step 1: {(S)-6-[(R)-7-Fluoro-4-(4,4,5,5-tetramethyl-[1,3,2]dioxaborolan-2-yl)-indan-1-yloxy]-2,3-dihydrobenzofuran-3-yl}-acetic acid a) 30.0 g (60.7 mmol) [(S)-6-((R)-4-bromo-7-fluoroindan-1-yloxy)-2,3-dihydrobenzo-furan-3-yl]-acetic acid morpholine salt is dissolved in 480 ml EtOH/water (1:1) and 6.30 ml conc. HCl (64.0 mmol, 37%) is added. The mixture is heated to reflux and stirred for 30 min. After cooling in an ice bath the suspension is filtered off, washed with cold water and dried to yield [(S)-6-((R)-4-bromo-7-fluoroindan-1-yloxy)-2,3-dihydrobenzo-furan-3-yl]-acetic acid.
b) Under argon, 30.0 g (73.7 mmol) [(S)-6-((R)-4-bromo-7-fluoroindan-1-yloxy)-2,3-dihydrobenzo-furan-3-yl]-acetic acid, 20.6 g (81.0 mmol) bis(pinacolato)diboron and 16.3 g (166 mmol) potassium acetate are suspended in 150 ml 2-methyltetrahydrofuran. The mixture is degassed and 165 mg (0.74 mmol) palladium(II) acetate and 528 mg (1.47 mmol) di(1-adamantyl)-n-butylphosphine are added. The mixture is degassed again and heated to 80° C. until completion of the reaction. Then, 150 ml water is added at 70° C. The aqueous phase is separated and the organic phase is cooled to r.t. and stirred overnight. The resulting suspension is cooled to 0° C. and 75 ml MCH is added. The crude product is filtered off, washed with cold 2-methyltetrahydrofuran/methylcyclohexane (2:1) and cold methylcyclohexane and dried. Further purification is achieved by recrystallization from 2-methyltetrahydrofuran or suspending the product in methylcyclohexane. Yield: 24.4 g; $R_f$=0.69 (PE/EtOAc/AcOH=0.69); Mass spectrum (ESI): m/z=455 [M+H]$^+$.

Step 2: ((S)-6-{(R)-7-Fluoro-4-[4-(3-hydroxy-3-methylbutoxy)-2,6-dimethylphenyl]-indan-1-yloxy}-2,3-dihydrobenzofuran-3-yl)acetic acid Under argon, 10.0 g (22.0 mmol) {(S)-6-[(R)-7-fluoro-4-(4,4,5,5-tetramethyl-[1,3,2]dioxaborolan-2-yl)-indan-1-yloxy]-2,3-dihydrobenzofuran-3-yl}-acetic acid, 7.59 g (26.4 mmol) 4-(4-bromo-3,5-dimethylphenoxy)-2-methylbutan-2-ol and 9.13 g (66.0 mmol) $K_2OC_3$ are suspended in 10 ml THF and 90 ml water. The mixture is degassed and 156 mg (0.22 mmol) Pd(4-dimethylaminophenyl-di-tert-butylphosphine)$_2$Cl$_2$ is added. The mixture is degassed and heated to reflux for approx. 1.5 h. The reaction mixture is cooled to r.t. and 90 ml THF is added at 40° C. Then, 10.9 g (0.11 mol) conc. HCl (37%) is added to adjust to pH=4. The organic phase is separated. After addition of 100 ml water, THF is distilled off in vacuum at 54° C. 100 ml isopropanol is added and the suspension is heated to 80° C. The resulting solution is cooled to 0° C. and stirred overnight. The precipitated product is filtered off, washed twice with cold water/isopropanol mixture (1:2) and dried. Yield: 9.53 g; $R_f$=0.28 (silica gel, PE/EtOAc/AcOH=5/5/0.1); Mass spectrum (ESI): m/z=535 [M+H]$^+$.

Examples 54 and 55 are analogously obtained from [(S)-6-((R)-4-bromo-7-fluoroindan-1-yloxy)-2,3-dihydrobenzofuran-3-yl]-acetic acid (e.g., as acid or the piperazinium or morpholinium salt) and the corresponding boronic acid or ester of the coupling partner, e.g., 1-[3,5-dimethyl-4-(4,4,5,5-tetramethyl-[1,3,2]dioxaborolan-2-yl)-phenoxy]-2-methyl-propan-2-ol and 4-[3,5-dimethyl-4-(4,4,5,5-tetramethyl-[1,3,2]dioxa-borolan-2-yl)-phenoxy]-tetrahydropyran, respectively. Examples 54 and 55 are also obtained from {(S)-6-[(R)-7-fluoro-4-(4,4,5,5-tetramethyl-[1,3,2]dioxaborolan-2-yl)-indan-1-yloxy]-2,3-dihydrobenzofuran-3-yl}-acetic acid (e.g., as acid or the piperazinium or morpholinium salt) and the corresponding bromide or chloride of the coupling partner, e.g., 1-(4-bromo-3,5-dimethylphenoxy)-2-methyl-propan-2-ol and 4-[3,5-dimethyl-4-(4,4,5,5-tetramethyl-[1,3,2]dioxaborolan-2-yl)-phenoxy]-tetrahydropyran, respectively, under the conditions described above for Example 53.

Example 60 is also obtained from [(S)-6-((R)-4-bromo-5-trifluoromethyl-indan-1-yloxy)-2,3-dihydrobenzofuran-3-yl]-acetic acid (e.g., as acid or the piperazinium or morpholinium salt) and the corresponding boronic acid or ester of the coupling partner, e.g., 2-[4-(3-methanesulfonyl-propoxy)-phenyl]-4,4,5,5-tetramethyl-[1,3,2]dioxaborolane, following the procedure described in Step 2 of Example 53 described above.

Examples 57 and 58 are also obtained from [(S)-6-((R)-4-bromo-7-fluoroindan-1-yloxy)-2,3-dihydrobenzofuran-3-yl]-acetic acid via coupling {(S)-6-[(R)-4-hydroxy-7-fluoroindan-1-yloxy)-2,3-dihydrobenzofuran-3-yl}-acetic acid methyl ester and the corresponding aryl bromide, 6-bromo-1-methyl-indazole and 4-bromo-anisole, respectively, following the proceeding described for Example 57 in the scheme below.

Example 57

{(S)-6-[(R)-7-Fluoro-4-(1-methyl-1H-indazol-6-yloxy)-indan-1-yloxy]-2,3-dihydrobenzofuran-3-yl}-acetic acid

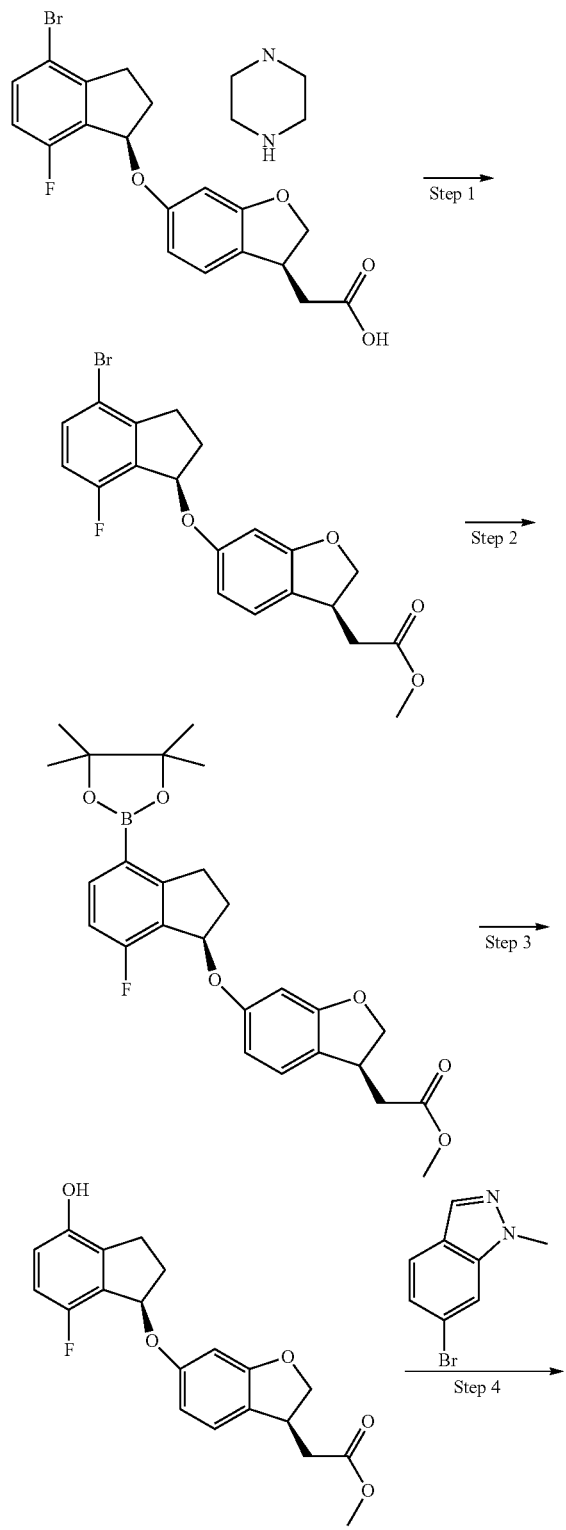

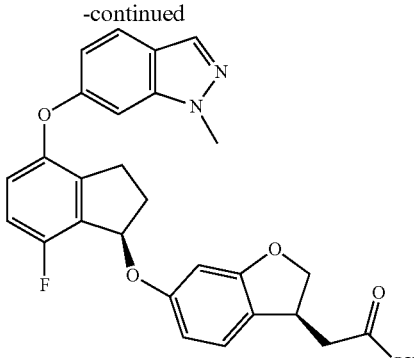

Step 1: [(S)-6-((R)-4-Bromo-7-fluoroindan-1-yloxy)-2,3-dihydrobenzofuran-3-yl]-acetic acid methyl ester 5.87 g (11.9 mmol) [(S)-6-((R)-4-bromo-7-fluoroindan-1-yloxy)-2,3-dihydrobenzo-furan-3-yl]-acetic acid morpholine salt is suspended in 22 ml MeOH. Then, 3.56 ml (14.2 mmol) HCl (4 M in dioxane) is added and the funnel is rinsed with 1.50 ml MeOH. The mixture is stirred overnight at r.t. and seeds are added. After 30 min, 5.90 ml water is added and stirring is continued. The precipitated product is filtered off, washed with 14.6 ml MeOH/water (4:1) and dried. Yield: 4.25 g; $R_f$=0.39 (silica gel, PE/EtOAc=8/2); Mass spectrum (ESI): m/z=421 [M+H]$^+$.

Step 2: {(S)-6-[(R)-7-Fluoro-4-(4,4,5,5-tetramethyl-[1,3,2]dioxaborolan-2-yl)-indan-1-yloxy]-2,3-dihydrobenzofuran-3-yl}-acetic acid methyl ester Under argon, 4.05 g (9.63 mmol) [(S)-6-((R)-4-bromo-7-fluoroindan-1-yloxy)-2,3-dihydrobenzo-furan-3-yl]-acetic acid methyl ester, 2.57 g (10.1 mmol) bis(pinacolato)diboron, 2.13 g (21.7 mmol) potassium acetate and 70.5 mg (0.08 mmol) PdCl$_2$(1,1'-bis(diphenylphosphino)ferrocene)×DCM are mixed in 10 ml toluene and heated to reflux. After 21 h, the mixture is cooled to r.t., filtered and the filter cake is washed with toluene (2 ml). To the combined filtrates 0.4 g charcoal is added and stirring is continued. The mixture is filtered again and the cake is washed with toluene (1 ml). After evaporation to dryness the titled compound is obtained. Yield: 4.41 g; $R_f$=0.38 (silica gel, PE/EtOAc=8/2); Mass spectrum (ESI): m/z=469 [M+H]$^+$.

Step 3: [(S)-6-((R)-7-Fluoro-4-hydroxyindan-1-yloxy)-2,3-dihydrobenzofuran-3-yl]-acetic acid methyl ester 4.41 g (8.72 mmol) {(S)-6-[(R)-7-fluoro-4-(4,4,5,5-tetramethyl-[1,3,2]dioxaborolan-2-yl)-indan-1-yloxy]-2,3-dihydrobenzofuran-3-yl}-acetic acid methyl ester is dissolved in 10 ml EtOH and 2.20 ml glacial acetic acid and 2.20 ml water are added. The funnel is rinsed with 7.50 ml EtOH. Then, 2.28 g (14.8 mmol) sodium perborate is added in portions at r.t. and the mixture is stirred. After complete addition, 1.40 ml water and 1.6 ml toluene is added. The organic phase is separated and 1.60 ml water is added. After cooling to 0° C., the 2-phasic mixture is seeded and stirring is continued. The precipitated product is filtered off, washed with cold toluene and dried. Yield: 2.86 g; $R_f$=0.22 (silica gel, PE/EtOAc=7/3); Mass spectrum (ESI): m/z=359 [M+H]$^+$.

Step 4: {(S)-6-[(R)-7-Fluoro-4-(1-methyl-1H-indazol-6-yloxy)-indan-1-yloxy]-2,3-dihydrobenzofuran-3-yl}-acetic acid 2.04 g (5.68 mmol) [(S)-6-((R)-7-fluoro-4-hydroxyindan-1-yloxy)-2,3-dihydrobenzo-furan-3-yl]-acetic acid methyl ester (product of step 3), 1.26 g (5.97 mmol) 6-bromo-1-methyl-1H-indazole, 3.70 g (11.4 mmol) Cs$_2$CO$_3$, 0.24 g (1.70 mmol) N,N-dimethylglycine hydrochloride and 0.11 mg (0.57 mmol) CuI are mixed with 20 ml 1,4-dioxane and heated to reflux for 20 h. The mixture is cooled to r.t. and 20 ml THF is added. The suspension is filtered, the filter cake is washed with 12 ml 1,4-dioxane/toluene (1:1) and the combined filtrates are evaporated to dryness. The residue is dissolved in 18 ml acetone at 50° C. and filtered through a pad of charcoal. At r.t. 27 ml water is added to the filtrate and the mixture is cooled to 0° C. The precipitate is filtered off, washed with water and dried. Upon saponification with aq. NaOH in methanol the titled compound is obtained (see general procedure above). Yield: 1.62 g R$_f$=0.40 (silica gel, PE/EtOAc/AcOH=5/5/0.1); Mass spectrum (ESI): m/z=475 [M+H]$^+$.

6-Bromo-1-methyl-1H-indazole may be obtained as follows: At 0° C. 5.00 g (24.6 mmol) 4-bromo-2-fluoro-benzaldehyde and 5.11 g (36.9 mmol) K$_2$CO$_3$ is added to 10 ml NMP. Then, 13 ml (264 mmol) methylhydrazine is added dropwise. The mixture is heated to 100° C. and stirred overnight. After cooling to r.t. 40 ml water is added. The product is filtered off, washed with water and dried.

Examples 61 and 62 are also obtained from {(S)-6-[(R)-4-bromo-5-trifluoromethyl-indan-1-yloxy]-2,3-dihydrobenzofuran-3-yl}-acetic acid (Example 59) via coupling {(S)-6-[(R)-4-bromo-5-trifluoromethyl-indan-1-yloxy]-2,3-dihydrobenzofuran-3-yl}-acetic acid methyl ester and the corresponding trifluoroborate, potassium (morpholin-4-yl)methyltrifluoroborate and potassium trifluoro-((2-methyl-6,7-dihydro-4H-thiazolo(5,4-c)pyridin-5-yl)methyl)borate, respectively, following the proceeding described for Example 61 in the scheme below.

Example 61

{(S)-6-[(R)-4-Morpholin-4-ylmethyl-5-trifluoromethyl-indan-1-yloxy]-2,3-dihydrobenzofuran-3-yl}-acetic acid

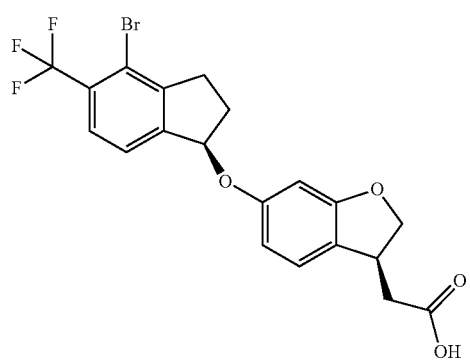 [SMILES: O=C(O)C[C@@H]1COc2cc(O[C@@H]3CCc4c3ccc(C(F)(F)F)c4Br)ccc21]

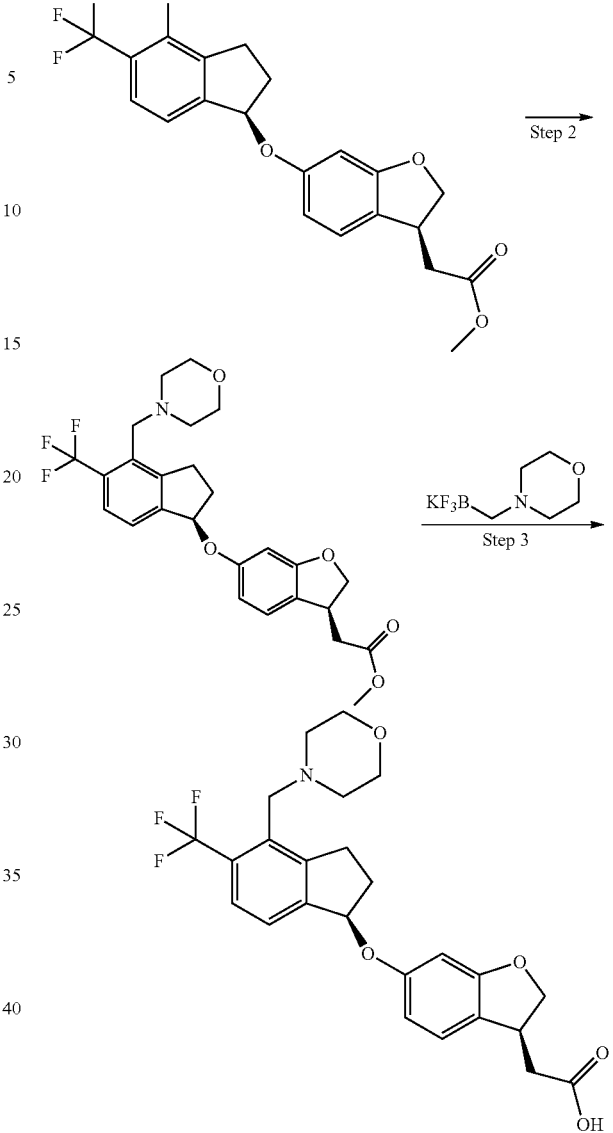

Step 1: {(S)-6-[(R)-4-Bromo-5-trifluoromethyl-indan-1-yloxy]-2,3-dihydrobenzofuran-3-yl}-acetic acid methyl ester The title compound is prepared from {(S)-6-[(R)-4-bromo-5-trifluoromethyl-indan-1-yloxy]-2,3-dihydrobenzofuran-3-yl}-acetic acid (Example 59) following a procedure analogous to that described in Step 1 of Example 57.

Step 2: {(S)-6-[(R)-4-Morpholin-4-ylmethyl-5-trifluoromethyl-indan-1-yloxy]-2,3-dihydrobenzofuran-3-yl}-acetic acid methyl ester The title compound is prepared from {(S)-6-[(R)-4-bromo-5-trifluoromethyl-indan-1-yloxy]-2,3-dihydrobenzofuran-3-yl}-acetic acid methyl ester and potassium (morpholin-4-yl)methyltrifluoroborate following a procedure analogous to that described in Step 1 of Intermediate 9.

Step 3: {(S)-6-[(R)-4-Morpholin-4-ylmethyl-5-trifluoromethyl-indan-1-yloxy]-2,3-dihydrobenzofuran-3-yl}-acetic acid The title compound is prepared from {(S)-6-[(R)-4-morpholin-4-ylmethyl-5-trifluoromethyl-indan-1-yloxy]-2,3-dihydrobenzofuran-3-yl}-acetic acid methyl ester by saponification with aq. NaOH in methanol as described above for Examples 1-11.

Example 64

((S)-6-{(R)-4-[2,6-Dimethyl-4-(2-methyl-2H-tetrazol-5-yl)-phenyl]-7-fluoroindan-1-yloxy}-2,3-dihydrobenzofuran-3-yl)acetic acid

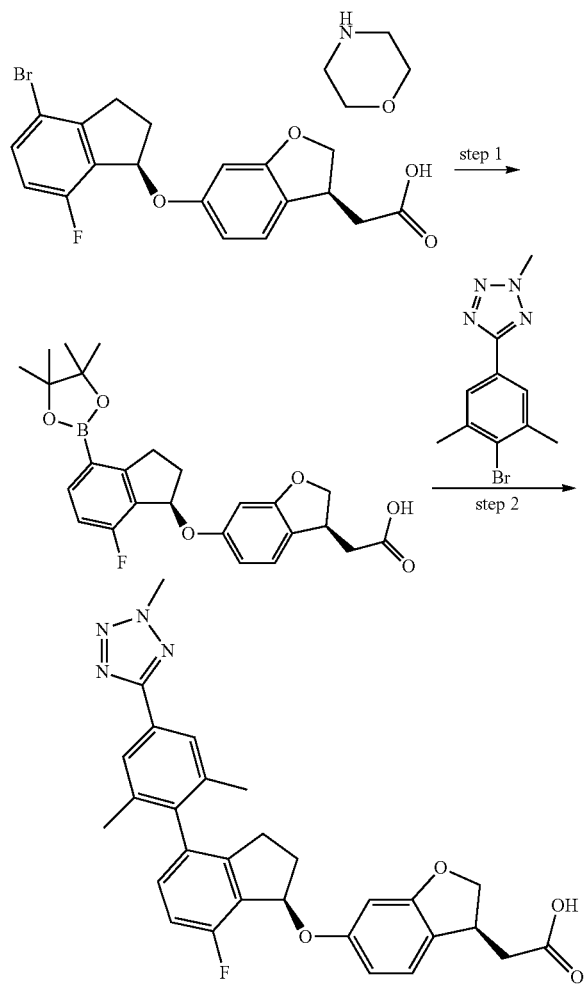

Step 1: {(S)-6-[(R)-7-Fluoro-4-(4,4,5,5-tetramethyl-[1,3,2]dioxaborolan-2-yl)-indan-1-yloxy]-2,3-dihydrobenzofuran-3-yl}-acetic acid 30.0 g (60.7 mmol) [(S)-6-((R)-4-bromo-7-fluoroindan-1-yloxy)-2,3-dihydrobenzo-furan-3-yl]-acetic acid morpholine salt is dissolved in 480 ml EtOH/water (1:1) and 6.30 ml conc. aq. HCl (64.0 mmol, 37%) is added. The mixture is heated to reflux and stirred for 30 min. After cooling in an ice bath the suspension is filtered off, washed with cold water and dried to yield [(S)-6-((R)-4-bromo-7-fluoroindan-1-yloxy)-2,3-dihydrobenzo-furan-3-yl]-acetic acid.

Under argon 30.0 g (73.7 mmol) [(S)-6-((R)-4-bromo-7-fluoroindan-1-yloxy)-2,3-dihydrobenzo-furan-3-yl]-acetic acid, 20.6 g (81.0 mmol) bis(pinacolato)diboron and 16.3 g (166 mmol) KOAc are suspended in 150 ml MeTHF. The mixture is degassed and 165 mg (0.74 mmol) Pd(OAc)$_2$ and 528 mg (1.47 mmol) di(1-adamantyl)-n-butylphosphine is added. The mixture is degassed again and heated to 80° C. until completion of the reaction. Then, 150 ml water is added at 70° C. The aqueous phase is separated and the organic phase is cooled to r.t. and stirred overnight. The resulting suspension is cooled to 0° C. and 75 ml MCH is added. The crude product is filtered off, washed with cold MeTHF/MCH (2:1) and cold MCH and dried. Further purification is achieved by recrystallization from MeTHF or suspending the product in MCH.

Step 2: ((S)-6-{(R)-4-[2,6-Dimethyl-4-(2-methyl-2H-tetrazol-5-yl)-phenyl]-7-fluoroindan-1-yloxy}-2,3-dihydrobenzofuran-3-yl)acetic acid Under argon 1 ml dioxane and 9 ml water is added to 1.00 g (2.20 mmol) {(S)-6-[(R)-7-fluoro-4-(4,4,5,5-tetramethyl-[1,3,2]dioxaborolan-2-yl)-indan-1-yloxy]-2,3-dihydrobenzofuran-3-yl}-acetic acid, 0.63 g (2.31 mmol) 5-(4-bromo-3,5-dimethylphenyl)-2-methyl-2H-tetrazole and 1.19 g (5.50 mmol) K$_3$PO$_4$. The mixture is degassed and 15.6 mg (0.02 mmol) PdCl$_2$(amphos) is added. The mixture is heated to 100° C. and stirred until completion of the reaction. After cooling to r.t. 25 ml aq. HCl (4N) is added and the product is extracted with iPrOAc (3×25 ml). The combined extracts are washed with brine, dried and evaporated to dryness. The crude product is recrystallized from hot EtOH/water (6:1) and dried in vacuum. Yield: 0.93 g; R$_f$=0.38 (PE/EtOAc/AcOH=5/5/0.1); Mass spectrum (ESI): m/z=515 [M+H]$^+$.

Alternatively, the product is synthesized from {(S)-6-[(R)-7-fluoro-4-(4,4,5,5-tetramethyl-[1,3,2]dioxaborolan-2-yl)-indan-1-yloxy]-2,3-di hydrobenzofuran-3-yl}-acetic acid methyl ester and 5-(4-bromo-3,5-dimethylphenyl)-2-methyl-2H-tetrazole following the procedure described above and subsequent saponification of the resulting ester.

5-(4-Bromo-3,5-dimethylphenyl)-2H-tetrazole may be obtained as follows: To a solution of 135 g (0.642 mol) 4-bromo-3,5-dimethylbenzonitrile in 960 mL anhydrous xylene, 141.6 g (1.028 mol) sodium azide and 10.48 g (1.028 mol) triethylammonium chloride is added. The mixture is heated to 115° C. and stirred overnight. After cooling to r.t. the reaction mixture is poured into 2 L of ice water and the pH is adjusted to pH=1 by acidification with conc. aq. hydrochloric acid. Stirring is continued for 1 h. The crude product is filtered off, washed with n-hexane (1x 500 mL) and water (3×600 mL) and dried to yield the intermediate 5-(4-bromo-3,5-dimethylphenyl)-2H-tetrazole. 166 g (0.29 mol) 5-(4-bromo-3,5-dimethylphenyl)-2H-tetrazole is dissolved in 3.2 L DMF and cooled to −10° C., before 305 g (2.15 mol) iodomethane is added. Afterwards, a solution of 71.3 g (0.742 mol) sodium tert-butoxide in 810 mL anhydrous THF is added slowly over a period of 25 min whilst keeping the temperature constant. After full conversion the reaction mixture is warmed to r.t. and poured into 1 L water. The resulting suspension is stirred for an additional hour at r.t. The crude product is filtered off, washed with water (3×1 L) and dried. After recrystallization from acetonitrile/water (1:1) mixture 90.8 g of the title compound is obtained as off white solid.

The invention claimed is:
1. A compound of formula (I)

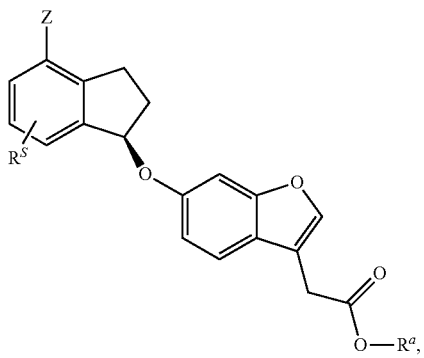

wherein:
R$^S$ is F or CF$_3$;
R$^a$ is H or C$_{1-4}$-alkyl; and
Z is a leaving group or an optionally protected hydroxyl group,
or a salt of the compound of formula (I) wherein R$^a$ is H.

2. The compound of formula (I) according to claim 1, wherein R$^a$ is —CH$_3$, or a salt thereof.

3. The compound of formula (I) according to claim 1, wherein:
Z is Cl, Br, I, or an optionally protected hydroxyl group.

4. (6-(R)-(4-Bromo-7-fluoroindan-1-yloxy)benzofuran-3-yl)acetic acid, or a salt thereof.

5. (6-(R)-(4-Bromo-7-fluoroindan-1-yloxy)benzofuran-3-yl)acetic acid methyl ester.

6. A process for preparing a compound of formula (I') according to claim 1, comprising reacting a compound of formula (II) with a compound of formula (III):

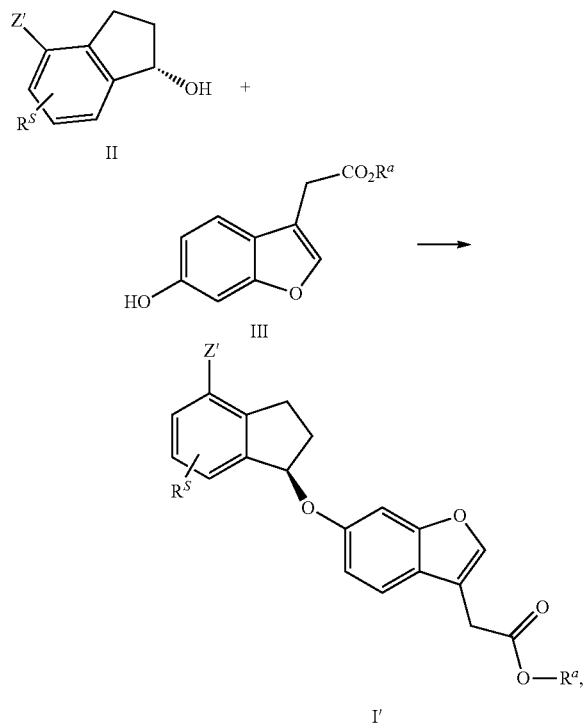

wherein R$^S$ is F or CF$_3$, R$^a$ is C$_{1-4}$-alkyl and, Z' is a leaving group or a protected hydroxyl group.

7. The process of claim 6, further comprising ester cleavage to convert R$^a$ to H.

8. The process of claim 6, wherein R$^a$ is —CH$_3$.

9. The process of claim 6, wherein Z is Cl, Br, I, or a protected hydroxyl group.

10. A process for preparing indanyloxydihydrobenzofuranylacetic acids of formulae IV.I, IV.II, and IV.III

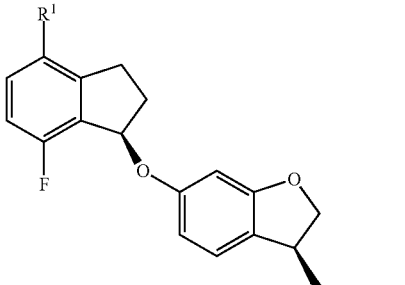

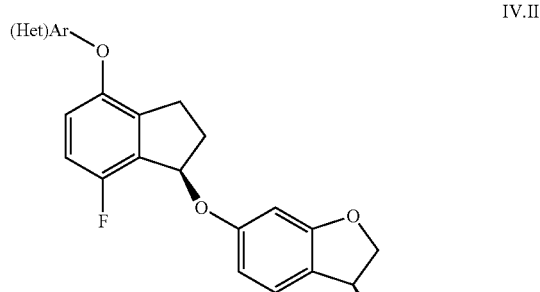

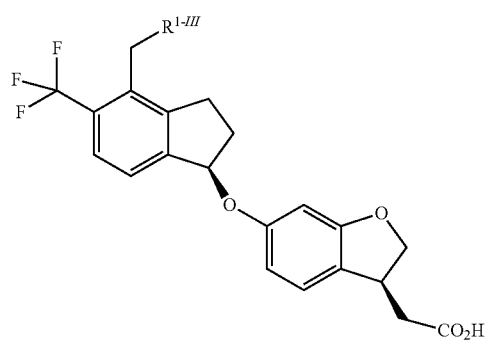

wherein in formula IV.I
R$^1$ is selected from the group consisting of a phenyl ring, a tetrazolyl ring, and a 5- or 6-membered heteroaromatic ring which contains 1, 2, or 3 heteroatoms independently selected from =N—, —NH—, —O—, and —S—, wherein optionally a second ring is annulated to the phenyl or heteroaromatic ring, and the second ring is 5- or 6-membered, partially unsaturated or aromatic and optionally contains 1, 2, or 3 heteroatoms independently selected from =N—, —NH—, —O—, and —S— with the proviso that only up to two of the heteroatoms are O and S and no O—O, S—S, and S—O bond is formed, and wherein in the second ring independently of the presence of heteroatoms 1 or 2 CH$_2$ groups are optionally replaced by —C(=O)—, —S(=O)—, or —S(=O)$_2$—, and the phenyl ring, tetrazolyl ring, heteroaromatic ring, annulated phenyl ring, and annulated heteroaromatic ring are substituted with one group R$^3$, and each of the phenyl ring, tetrazolyl ring, heteroaromatic ring, annulated phenyl ring, and annulated heteroaromatic ring is optionally additionally substituted with 1 to 4 groups independently selected from $R^4$, and wherein in the heteroaromatic ring and/or the second ring the H-atom in one or more NH groups is replaced by $R^N$ or $R^3$;

$R^3$ is $C_{1-6}$-alkyl, $C_{2-6}$-alkenyl, $C_{2-6}$-alkinyl, $C_{3-6}$-cycloalkyl, $C_{1-4}$-alkyl-NH—, $(C_{1-4}$-alkyl$)_2$N—, $C_{1-6}$-alkyl-O—, $C_{3-6}$-cycloalkyl-O—, $C_{1-4}$-alkyl-S—, $C_{1-4}$-alkyl-S(=O)—, or $C_{1-4}$-alkyl-S(=O)$_2$, wherein each alkyl and cycloalkyl group and each alkyl and cycloalkyl sub-group within the groups mentioned is substituted with 1 to 3 groups independently selected from $R^5$ and optionally substituted with 1 or more F atoms, or $C_{1-4}$-alkyl-C(=O)—, heterocyclyl-C(=O)—, HNR$^N$—C(=O)—, $C_{1-4}$-alkyl-NR$^N$—C(=O)—, $C_{3-6}$-cycloalkyl-NR$^N$—C(=O)—, heterocyclyl-NR$^N$—C(=O)—, phenyl-NR$^N$—C(=O)—, heteroaryl-NR$^N$—C(=O)—, HO$_2$C—, $C_{1-4}$-alkyl-O—C(=O)—, $C_{3-6}$-cycloalkyl-O—C(=O)—, heterocyclyl-O—C(=O)—, —NHR$^N$, $C_{1-4}$-alkyl-C(=O)NR$^N$—, $C_{3-6}$-cycloalkyl-C(=O)NR$^N$—, heterocyclyl-C(=O)NR$^N$—, phenyl-C(=O)NR$^N$—, heteroaryl-C(=O)NR$^N$—, $C_{1-4}$-alkyl-S(=O)$_2$NR$^N$—, $C_{3-6}$cycloalkyl-S(=O)$_2$NR$^N$—, heterocyclyl-S(=O)$_2$NR$^N$—, phenyl-S(=O)$_2$NR$^N$—, heteroaryl-S(=O)$_2$NR$^N$—, heterocyclyl-O—, phenyl-O—, heteroaryl-O—, $C_{3-6}$-cycloalkyl-S—, heterocyclyl-S—, phenyl-S—, heteroaryl-S—, $C_{3-6}$-cycloalkyl-S(=O)—, heterocyclyl-S(=O)—, phenyl-S(=O)—, heteroaryl-S(=O)—, $C_{3-6}$-cycloalkyl-S(=O)$_2$—, heterocyclyl-S(=O)$_2$—, phenyl-S(=O)$_2$—, heteroaryl-S(=O)$_2$—, HNR$^N$—S(=O)$_2$—, $C_{1-4}$-alkyl-NR$^N$—S(=O)$_2$—, heterocyclyl, phenyl, and heteroaryl, wherein each alkyl, cycloalkyl, and heterocyclyl group or sub-group within the groups mentioned is optionally substituted with 1 to 3 groups independently selected from $R^5$ and optionally substituted with 1 or more F atoms, and wherein each phenyl and heteroaryl group is optionally substituted with 1 to 5 substituents independently selected from $R^6$;

wherein heterocyclyl is selected from
  a cyclobutyl group wherein 1 CH$_2$ group is replaced by —NH— or —O—,
  a saturated or partially unsaturated $C_{5-7}$-cycloalkyl group wherein 1 CH$_2$ group is replaced by —C(=O)—, —NH—, —O—, —S(=O)— or —S(=O)$_2$— and/or 1 CH group by N;
  a saturated or partially unsaturated $C_{5-7}$-cycloalkyl group wherein 1 CH$_2$ group is replaced by —NH— or —O—, a second CH$_2$ group is replaced by —NH—, —C(=O)—, —S(=O)— or —S(=O)$_2$— and/or 1 CH group is replaced by N; and
  a saturated or partially unsaturated $C_{5-7}$-cycloalkyl group wherein 2 CH$_2$ groups are replaced by —NH— or 1 CH$_2$ group by —NH— and the other by —O— and a third CH$_2$ group is replaced by —C(=O)—, —S(=O)— or —S(=O)$_2$— and/or 1 CH group by N;

wherein heteroaryl is selected from
  a tetrazolyl ring, and a 5- or 6-membered heteroaromatic ring which contains 1, 2, or 3 heteroatoms independently selected from =N—, —NH—, —O—, and —S—, wherein in heteroaromatic groups containing a —HC=N— unit this group is optionally replaced by —NH—C(=O)—;
  wherein in heteroaryl and heterocyclyl rings with one or more NH groups each of them is replaced by NR$^N$ or NR$^5$, $R^4$ is selected from the group consisting of F, Cl, Br, I, CN, —OH, $C_{1-4}$-alkyl, $C_{3-6}$-cycloalkyl, HO—$C_{1-4}$-alkyl, —NR$^N$H, $C_{1-4}$-alkyl-NR$^N$—, $C_{1-4}$-alkyl-O—, $C_{3-6}$-cycloalkyl-O—, $C_{1-4}$-alkyl-S(=O)—, and $C_{1-4}$-alkyl-S(=O)$_2$—, wherein any alkyl and cycloalkyl group or sub-group within the groups mentioned is optionally substituted with 1 or more F atoms;

$R^5$ is selected from the group consisting of Cl, Br, I, $C_{1-4}$-alkyl-, CN, $C_{3-6}$-cycloalkyl, heterocyclyl-C(=O)—, H$_2$N—C(=O)—, $C_{1-4}$-alkyl-NR$^N$—C(=O)—, $C_{3-6}$-cycloalkyl-NR$^N$—C(=O)—, heterocyclyl-NR$^N$—C(=O)—, phenyl-NR$^N$—C(=O)—, heteroaryl-NR$^N$—C(=O)—, HO—C(=O)—, $C_{1-4}$-alkyl-O—C(=O)—, —NHR$^N$, $C_{1-4}$-alkyl-NR$^N$—, $C_{1-4}$-alkyl-C(=O)NR$^N$—, $C_{3-6}$-cycloalkyl-C(=O)NR$^N$—, heterocyclyl-C(=O)NR$^N$—, phenyl-C(=O)NR$^N$—, heteroaryl-C(=O)NR$^N$—, $C_{1-4}$-alkyl-S(=O)$_2$NR$^N$—, $C_{3-6}$-cycloalkyl-S(=O)$_2$NR$^N$—, heterocyclyl-S(=O)$_2$NR$^N$—, phenyl-S(=O)$_2$NR$^N$—, heteroaryl-S(=O)$_2$NR$^N$—, —OH, $C_{1-4}$-alkyl-O—, $C_{1-4}$alkyl-O—$C_{1-4}$-alkyl-O—, $C_{3-6}$-cycloalkyl-O—, heterocyclyl-O—, phenyl-O—, heteroaryl-O—, $C_{1-4}$-alkyl-S—, $C_{3-6}$-cycloalkyl-S—, heterocyclyl-S—, phenyl-S—, heteroaryl-S—, $C_{1-4}$-alkyl-S(=O)—, $C_{3-6}$-cycloalkyl-S(=O)—, heterocyclyl-S(=O)—, phenyl-S(=O)—, heteroaryl-S(=O)—, $C_{1-4}$-alkyl-S(=O)$_2$—, $C_{3-6}$-cycloalkyl-S(=O)$_2$—, heterocyclyl-S(=O)$_2$—, phenyl-S(=O)$_2$—, heteroaryl-S(=O)$_2$—, H$_2$N—S(=O)$_2$—, $C_{1-4}$-alkyl-NR$^N$—S(=O)$_2$—, heterocyclyl, phenyl, and heteroaryl, wherein any alkyl, cycloalkyl and heterocyclyl group or sub-group within the groups mentioned is optionally substituted with 1 or more F atoms and optionally substituted with 1 or 2 groups independently selected from H$_3$C—, HO—, H$_3$C—O—, and —CN;

wherein heterocyclyl is selected from
  a cyclobutyl group wherein 1 CH$_2$ group is replaced by —NR$^N$— or —O—,
  a saturated or partially unsaturated $C_{5-7}$-cycloalkyl group wherein 1 CH$_2$ group is replaced by —C(=O)—, —NR$^N$—, —O—, —S(=O)— or —S(=O)$_2$— and/or 1 CH group by N;
  a saturated or partially unsaturated $C_{5-7}$-cycloalkyl group wherein 1 CH$_2$ group is replaced by —NR$^N$— or —O—, a second CH$_2$ group is replaced by —NR$^N$—, —C(=O)—, —S(=O)— or —S(=O)$_2$— and/or 1 CH group is replaced by N; and
  a saturated or partially unsaturated $C_{5-7}$-cycloalkyl group wherein 2 CH$_2$ groups are replaced by —NR$^N$— or 1 CH$_2$ group by —NR$^N$— and the other by —O—, and a third CH$_2$ group is replaced by —C(=O)—, —S(=O)— or —S(=O)$_2$— and/or 1 CH group by N;

and wherein heteroaryl is selected from
  a tetrazolyl ring, and a 5- or 6-membered heteroaromatic ring which contains 1, 2, or 3 heteroatoms independently selected from =N—, —NH—, —O—, and —S—, wherein in heteroaromatic groups containing a —HC=N— unit this group is optionally replaced by —NR$^N$—C(=O)—, and wherein in heteroaromatic rings with one or more NH groups each of them is replaced by NR$^N$, and each heteroaryl group is optionally substituted with 1 to 3 substituents independently selected from F, Cl, —CH$_3$, —CN, and —O—CH$_3$;

R$^6$ is selected from the group consisting of F, Cl, Br, I, CN, C$_{1-4}$-alkyl, C$_{3-6}$-cycloalkyl-, HO—C$_{1-4}$-alkyl-, C$_{1-4}$-alkyl-O—C$_{1-4}$-alkyl-, R$^N$HN—, C$_{1-4}$-alkyl-O—, —S(=O)—C$_{1-4}$-alkyl, and S(=O)$_2$—C$_{1-4}$-alkyl, wherein any alkyl and cycloalkyl group or sub-group within the groups mentioned is optionally substituted with one or more F atoms; and R$^N$ is independently selected from the group consisting of H, C$_{1-4}$-alkyl, C$_{1-4}$-alkyl-C(=O)—, C$_{1-4}$-alkyl-NH—C(=O)—, C$_{1-4}$-alkyl-N(C$_{1-4}$-alkyl)-C(=O)—, C$_{1-4}$-alkyl-O—C(=O)—, and C$_{1-4}$-alkyl-S(=O)$_2$—;

wherein in formula IV.II (Het)Ar is linked via a carbon atom and is selected from the group (Het)Ar-G1 consisting of phenyl, naphthyl and a mono- or bicyclic heteroaromatic group having 5 to 10 ring member atoms of which 2 to 9 ring members are carbon atoms and either one ring member is an unsubstituted or substituted heteroatom selected from N, NH, NR$^{N-II}$, O, S, S(=O), and S(=O)$_2$, or one ring member is N and a second ring member is selected from N, NH, NR$^{N-II}$, O, S, S(=O), and S(=O)$_2$, or two ring members are N and a third ring member is selected from N, NH, NR$^{N-II}$, O, S, S(=O), and S(=O)$_2$, wherein in naphthyl the ring not attached to the indanyl-O atom of formula IV.II is optionally partially saturated, wherein in bicyclic heteroaromatic groups the ring not attached to the indanyl-O atom of formula IV.II is optionally partially saturated, while at least one aromatic ring includes a heteroatom, and optionally one ring member in the partially or fully saturated bridge is replaced by N, NH, NR$^{N-II}$, O, S, S(O), or S(=O)$_2$, or one ring member in the partially or fully saturated bridge is replaced by N, NH, or NR$^{N-II}$ and second ring member is replaced by NH, NR$^{N-II}$, O, S, C(=O), S(=O), or S(=O)$_2$, or two not vicinal ring members in a fully saturated bridge are replaced by O atoms, wherein any of these groups is optionally and independently substituted with 1 to 5 R$^{1-II}$ groups;

R$^{1-II}$ is selected from the group consisting of F, Cl, Br, I, CN, NO$_2$, NH$_2$, C$_{1-4}$-alkyl-NH—, (C$_{1-4}$-alkyl)$_2$N—, C$_{1-4}$-alkyl, C$_{2-4}$-alkenyl, C$_{2-4}$-alkinyl, OH, HO—C$_{1-4}$-alkyl, C$_{1-4}$-alkyl-O—, C$_{1-4}$-alkyl-O—C$_{1-4}$-alkyl, C$_{1-4}$-alkyl S—, C$_{1-4}$-alkyl-S(=O)—, C$_{1-4}$-alkyl-S(=O)$_2$—, C$_{3-6}$-cycloalkyl, and C$_{3-6}$-cycloalkyl-O—, wherein any alkyl and cycloalkyl group or submoiety is optionally substituted with 1 to 5 F atoms;

R$^{N-II}$ is selected from the group consisting of C$_{1-4}$-alkyl, C$_{3-4}$-alkenyl, HO—C$_{1-4}$-alkyl, C$_{1-4}$-alkyl-O C$_{1-4}$-alkyl, C$_{1-4}$-alkyl-C(=O)—, C$_{1-4}$-alkyl-S(=O)$_2$—, and C$_{3-6}$-cycloalkyl-, wherein any alkyl and cycloalkyl group or submoiety is optionally substituted with 1 to 5 F atoms;

wherein in formula IV.III

R$^{1-III}$ is selected from the group consisting of a monocyclic or bicyclic group having 5 to 12 ring member atoms of which 4 to 11 ring members are C atoms and 1 to 3 ring members are heteroatoms selected from N and NR$^{N-III}$, or 1 or 2 ring members are heteroatoms selected from N and NR$^{N-III}$ and 1 ring member is selected from O and S, or 1 ring member is N and 2 ring members are independently selected from O and S, with the proviso that no O—O, S—S, or S—O bond is formed, wherein the ring member atom attached to the —CH$_2$— group in formula IV.III is an N atom, wherein 1 CH$_2$ ring member attached to a ring member N atom is optionally replaced by a —C(=O)— group, wherein the monocyclic or bicyclic group is saturated or partially unsaturated, with the proviso that in bicyclic groups the ring attached to the —CH$_2$— group in formula IV.III is not aromatic, and wherein the bicyclic group is optionally a fused, bridged, or spiro ring system;

wherein any of these groups is optionally and independently substituted with 1 to 3 R$^{2-III}$ groups;

R$^{2-III}$ is selected from the group consisting of F, Cl, Br, I, C$_{1-4}$-alkyl, NC—, HO—C$_{1-4}$-alkyl, HO—, C$_{1-4}$-alkyl-O—, C$_{1-4}$-alkyl-O—C$_{1-4}$-alkyl, C$_{1-4}$-alkyl-S—, C$_{1-4}$-alkyl-S(=O)—, C$_{1-4}$-alkyl-S(=O)$_2$—, C$_{3-6}$-cycloalkyl-, and C$_{3-6}$-cycloalkyl-O—, wherein any alkyl and cycloalkyl group or submoiety is optionally substituted with 1 to 3 F atoms; and R$^{N-III}$ is selected from the group consisting of H, C$_{1-4}$-alkyl-C(O)—, and C$_{1-4}$-alkyl-O—C(O)—;

wherein any alkyl group or sub-group is straight-chained or branched, unless specified otherwise, the process comprising:

a) performing asymmetric catalytic hydrogenation in the presence of a transition metal catalyst and a chiral auxiliary, optionally in the presence of a base, on the compound of formula I or a salt thereof:

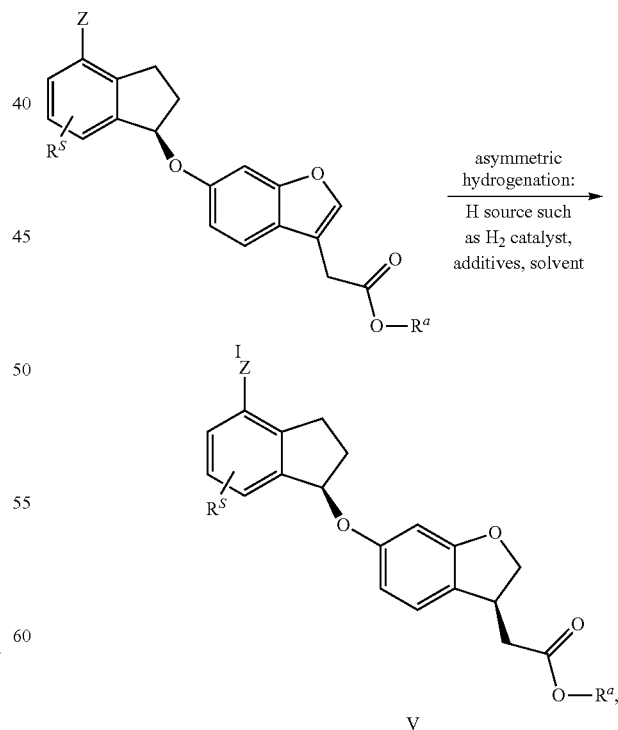

wherein R$^S$ is F or CF$_3$, R$^a$ is H or C$_{1-4}$-alkyl, and Z is a leaving group or protected hydroxyl group, and b) reacting the compound of formula V based on the identity of Z, as follows:

b-1) if Z is Cl, Br, I, reacting the compound of formula V with a compound of formula R¹—X, wherein X is B(OH)₂, B(OCMe₂CMe₂O), B(O₂CCH₂)₂NCH₃, BF₃K, ZnHal, or MgHal (where Hal is Cl, Br, or I), to obtain a compound of formula IV', which is subsequently saponified if $R^a$ of the compound of formula IV' is $C_{1-4}$-alkyl, to obtain a compound of formula IV

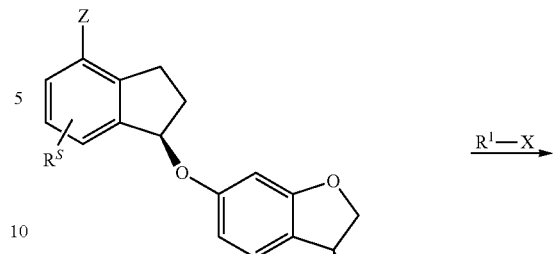

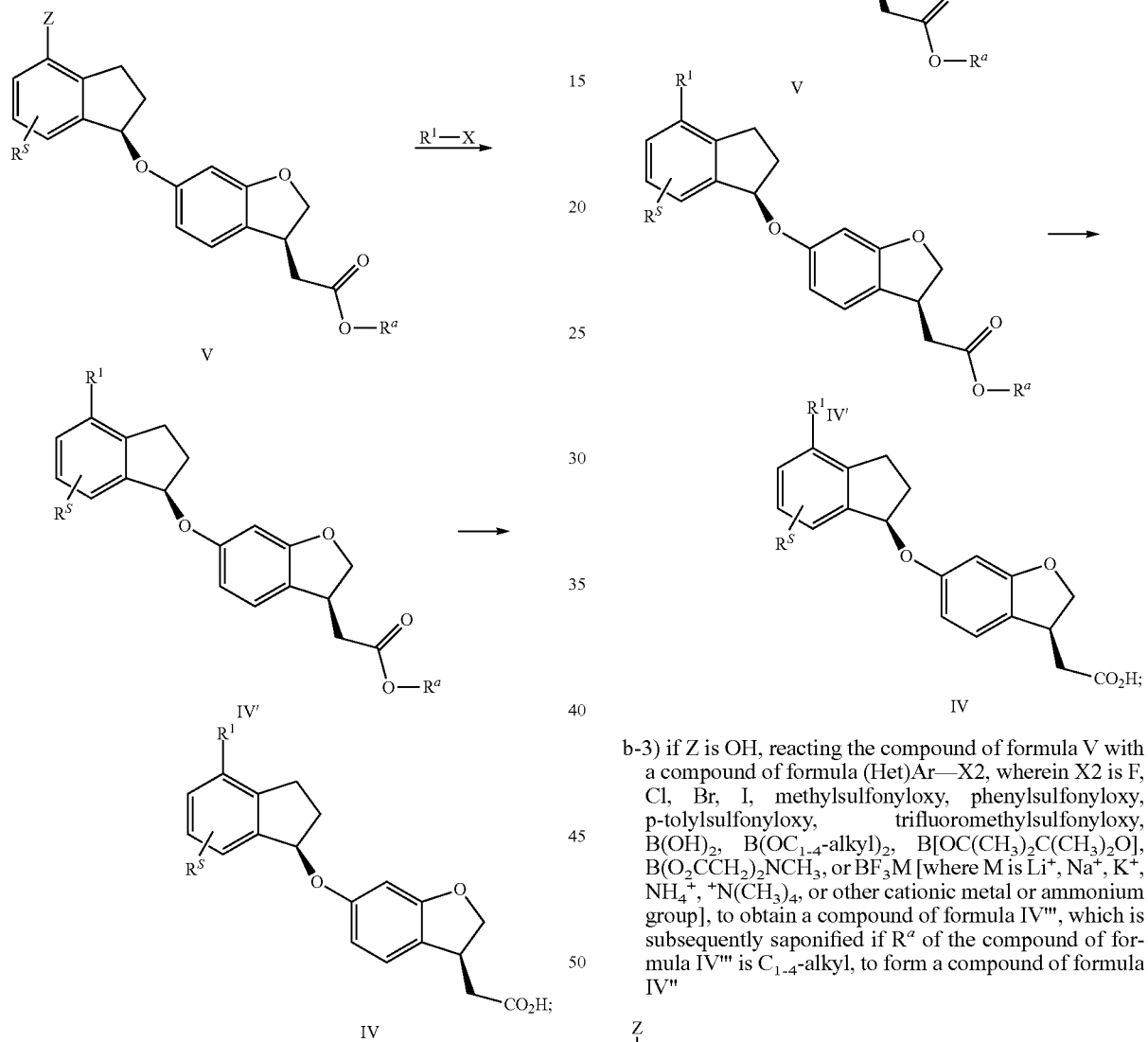

b-2) if Z is B(OH)₂, B(OC₁₋₄-alkyl)₂, B[OC(CH₃)₂C(CH₃)₂O], B(O₂CCH₂)₂NCH₃, or BF₃M [where M is Li⁺, Na⁺, K⁺, NH₄⁺, ⁺N(CH₃)₄, or other cationic metal or ammonium group], reacting the compound of formula V with a compound of formula R¹—X1, wherein X1 is Cl, Br, I, methylsulfonyloxy, phenylsulfonyloxy, p-tolylsulfonyloxy, or trifluoromethylsulfonyloxy, to obtain a compound of formula IV', which is subsequently saponified if $R^a$ of the compound of formula IV' is $C_{1-4}$-alkyl, to form a compound of formula IV b-3) if Z is OH, reacting the compound of formula V with a compound of formula (Het)Ar—X2, wherein X2 is F, Cl, Br, I, methylsulfonyloxy, phenylsulfonyloxy, p-tolylsulfonyloxy, trifluoromethylsulfonyloxy, B(OH)₂, B(OC₁₋₄-alkyl)₂, B[OC(CH₃)₂C(CH₃)₂O], B(O₂CCH₂)₂NCH₃, or BF₃M [where M is Li⁺, Na⁺, K⁺, NH₄⁺, ⁺N(CH₃)₄, or other cationic metal or ammonium group], to obtain a compound of formula IV''', which is subsequently saponified if $R^a$ of the compound of formula IV''' is $C_{1-4}$-alkyl, to form a compound of formula IV'''

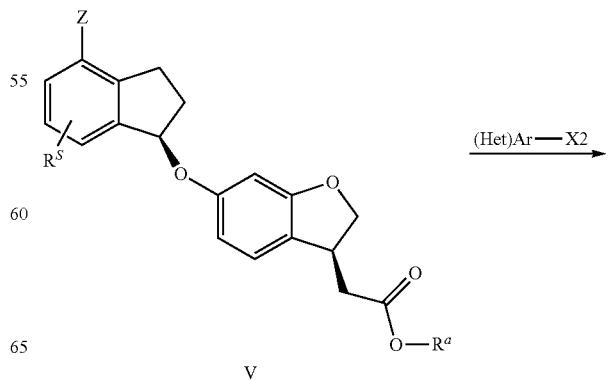

-continued

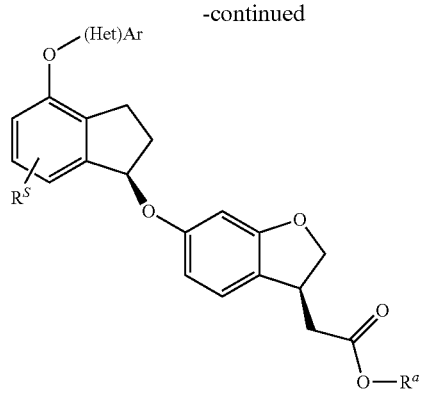

IV''' b-4) if Z is Cl, Br, I, methylsulfonyloxy, phenylsulfonyloxy, p-tolylsulfonyloxy, trifluoromethylsulfonyloxy, B(OH)$_2$, B(OC$_{1-4}$-alkyl)$_2$, B[OC(CH$_3$)$_2$C(CH$_3$)$_2$O], B(O$_2$CCH$_2$)$_2$NCH$_3$, or BF$_3$M [where M is Li$^+$, Na$^+$, K$^+$, NH$_4^+$, $^+$N(CH$_3$)$_4$, or other cationic metal or ammonium group], reacting the compound of formula V with a compound of formula (Het)Ar—OH, to obtain a compound of formula IV', which is subsequently saponified if R$^a$ of the compound of formula IV' is C$_{1-4}$-alkyl, to form a compound of formula IV -continued

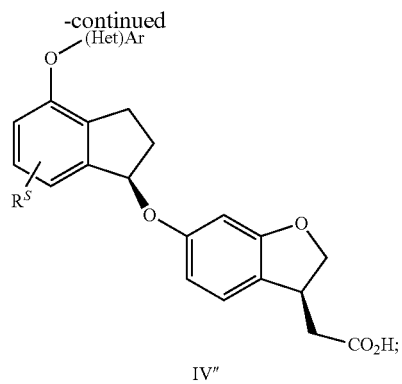

IV'' or b-5) if Z is Cl, Br, I, methylsulfonyloxy, phenylsulfonyloxy, p-tolylsulfonyloxy, trifluoromethylsulfonyloxy, reacting the compound of formula V with a compound of formula R$^{1-III}$—CH$_2$—X3, wherein X3 is B(OH)$_2$, B(OC$_{1-4}$-alkyl)$_2$, B[OC(CH$_3$)$_2$C(CH$_3$)$_2$O], B(O$_2$CCH$_2$)$_2$NCH$_3$, or BF$_3$M [where M is Li$^+$, Na$^+$, K$^+$, NH$_4^+$, $^+$N(CH$_3$)$_4$, or other cationic metal or ammonium group], and subsequent saponification of a compound of formula IV$^V$, wherein R$^a$ is C$_{1-4}$-alkyl, to obtain a compound of formula IV$^V$, which is subsequently saponified if R$^a$ of the compound of formula IV$^V$ is C$_{1-4}$-alkyl, to form a compound of formula IV$^I$

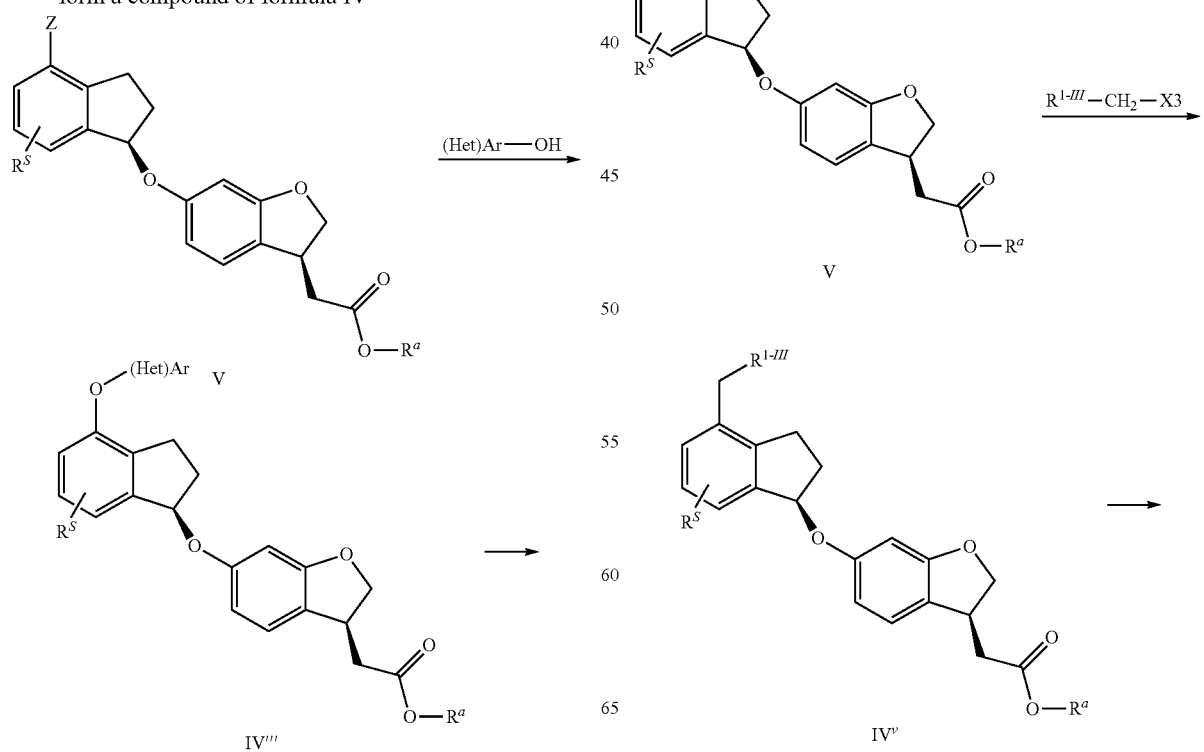

-continued

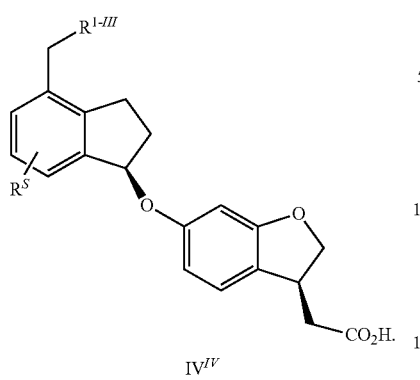

IV$^{IV}$

11. The process of claim 10, wherein the transition metal catalyst is Ir, Rh, Ru, Pd, or Fe catalyst.

12. The process of claim 10, wherein Z is Cl, Br, I, or an optionally protected hydroxyl group.

13. A process for preparing indanyloxydihydrobenzofuranylacetic acids of formulae IV.I, IV.II, and IV.III

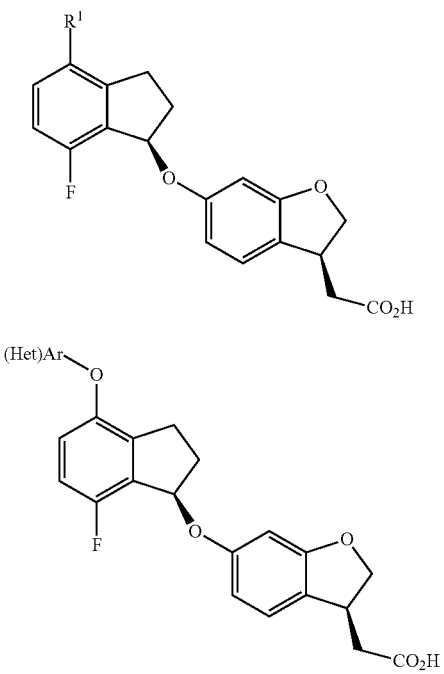

wherein $R^1$, (Het)Ar, and $R^{1\text{-}III}$ are defined as in claim 10, comprising:

c) reacting the compound of formula I, wherein $R^S$ is F or $CF_3$ and $R^a$ is H or $C_{1\text{-}4}$-alkyl, based on the identity of Z, as follows:

c-1) if Z is Cl, Br, I, reacting the compound of formula I with a compound of formula $R^1$—X, wherein X is $B(OH)_2$, $B(OCMe_2CMe_2O)$, $B(O_2CCH_2)_2NCH_3$, $BF_3K$, ZnHal, or MgHal (where Hal is Cl, Br, or I), to obtain a compound of formula VI,

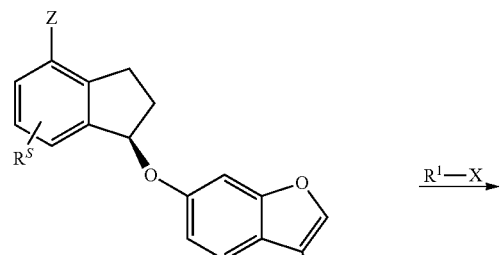

I

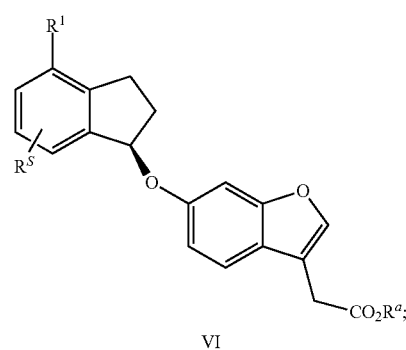

VI c-2) if Z is $B(OH)_2$, $B(OC_{1\text{-}4}\text{-alkyl})_2$, $B[OC(CH_3)_2C(CH_3)_2O]$, $B(O_2CCH_2)_2NCH_3$, or $BF_3M$ [where M is $Li^+$, $Na^+$, $K^+$, $NH_4^+$, $^+N(CH_3)_4$, or other cationic metal or ammonium group], reacting the compound of formula I with a compound of formula $R^1$—X1, wherein X1 is Cl, Br, I, methylsulfonyloxy, phenylsulfonyloxy, p-tolylsulfonyloxy, or trifluoromethylsulfonyloxy, to obtain a compound of formula VI

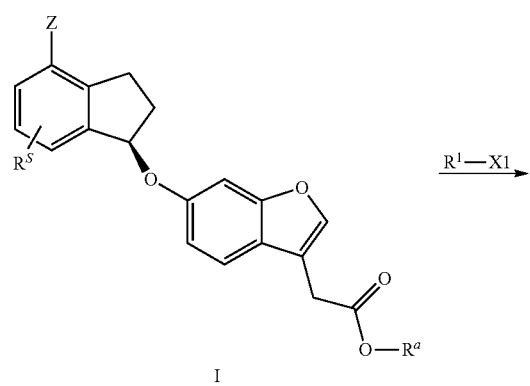

I

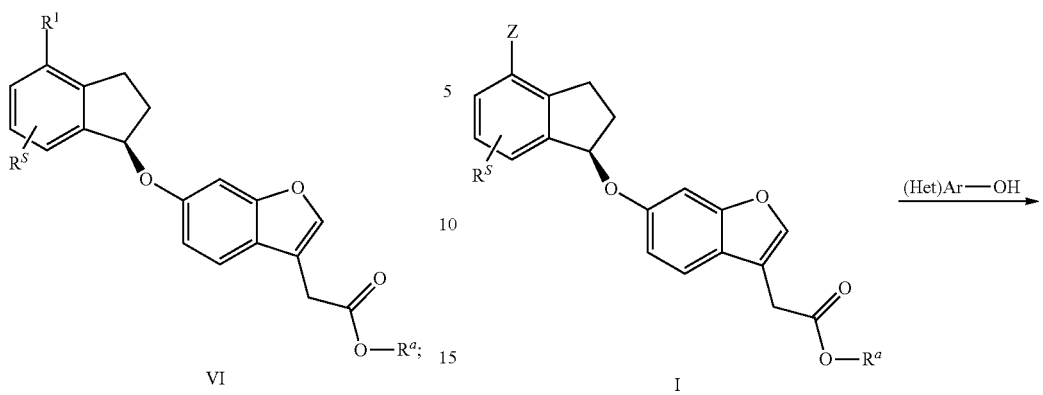

c-3) if Z is OH, reacting the compound of formula I with a compound of formula (Het)Ar—X2, wherein X2 is F, Cl, Br, I, methylsulfonyloxy, phenylsulfonyloxy, p-tolylsulfonyloxy, trifluoromethylsulfonyloxy, $B(OH)_2$, $B(OC_{1-4}\text{-alkyl})_2$, $B[OC(CH_3)_2C(CH_3)_2O]$, $B(O_2CCH_2)_2NCH_3$, or $BF_3M$ [where M is $Li^+$, $Na^+$, $K^+$, $NH_4^+$, $^+N(CH_3)_4$, or other cationic metal or ammonium group], to obtain a compound of formula VI'

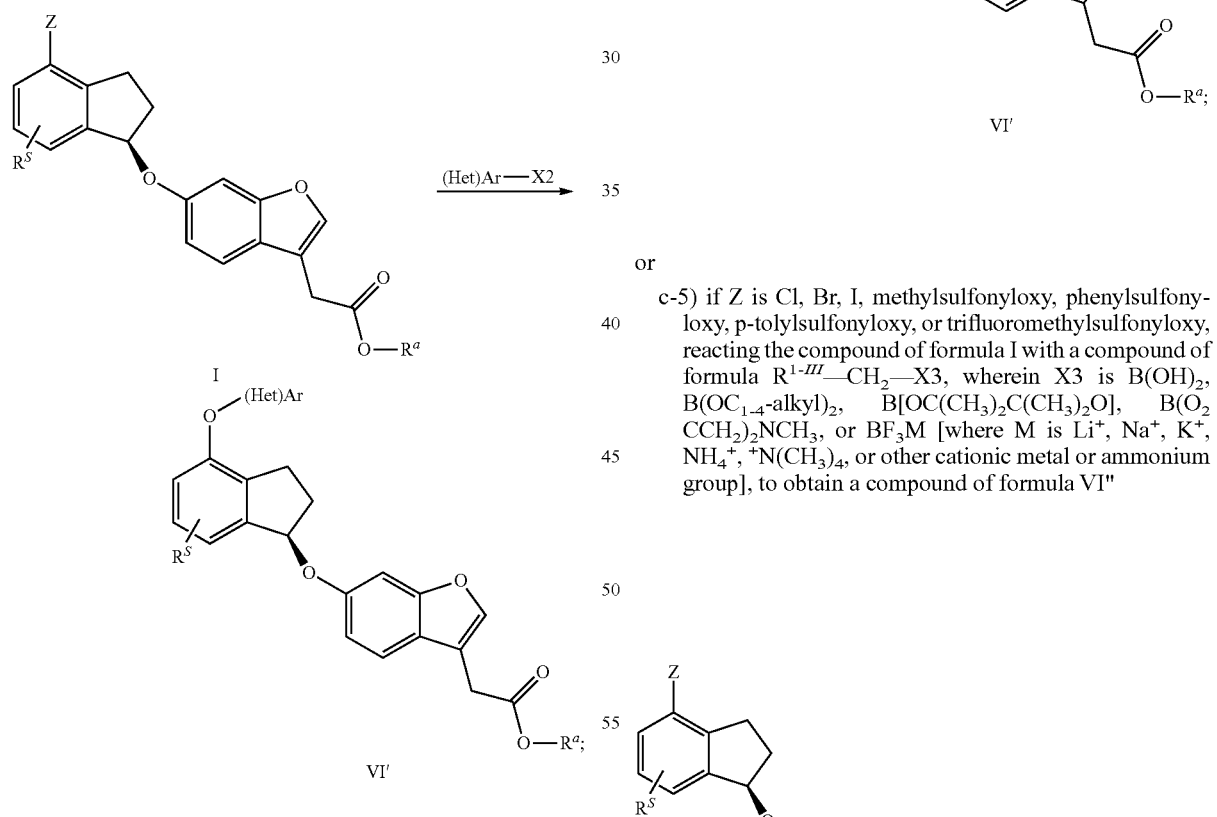

c-4) if Z is Cl, Br, I, methylsulfonyloxy, phenylsulfonyloxy, p-tolylsulfonyloxy, trifluoromethylsulfonyloxy, $B(OH)_2$, $B(OC_{1-4}\text{-alkyl})_2$, $B[OC(CH_3)_2C(CH_3)_2O]$, $B(O_2CCH_2)_2NCH_3$, or $BF_3M$ [where M is $Li^+$, $Na^+$, $K^+$, $NH_4^+$, $^+N(CH_3)_4$, or other cationic metal or ammonium group], reacting the compound of formula I with a compound of formula (Het)Ar—OH, to form a compound of formula VI' or c-5) if Z is Cl, Br, I, methylsulfonyloxy, phenylsulfonyloxy, p-tolylsulfonyloxy, or trifluoromethylsulfonyloxy, reacting the compound of formula I with a compound of formula $R^{1-III}$—$CH_2$—X3, wherein X3 is $B(OH)_2$, $B(OC_{1-4}\text{-alkyl})_2$, $B[OC(CH_3)_2C(CH_3)_2O]$, $B(O_2CCH_2)_2NCH_3$, or $BF_3M$ [where M is $Li^+$, $Na^+$, $K^+$, $NH_4^+$, $^+N(CH_3)_4$, or other cationic metal or ammonium group], to obtain a compound of formula VI"

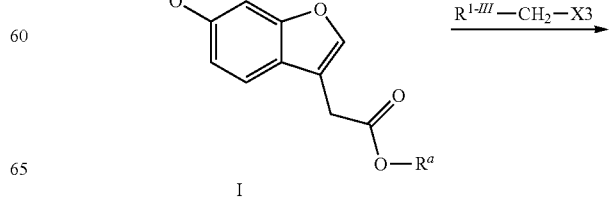

-continued

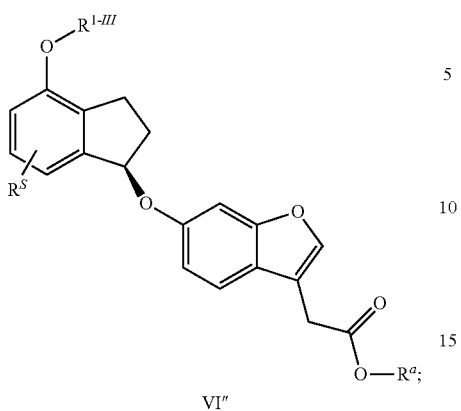

VI″ and d) performing asymmetric catalytic hydrogenation in the presence of a transition metal catalyst and a chiral auxiliary, optionally in the presence of a base, on the compound of formula VI″ or a salt thereof, wherein Z″ is $R^1$, O-(Het)Ar, or $CH_2$—$R^{1\text{-}III}$ 15. The process of claim 13, wherein Z is Cl, Br, I, or an optionally protected hydroxyl group.

16. A process for preparing indanyloxydihydrobenzofuranylacetic acids of formula V

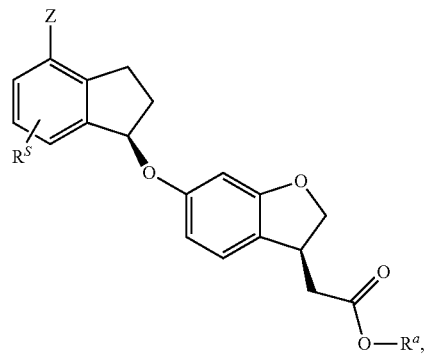

wherein $R^S$ is F or $CF_3$, $R^a$ is H or $C_{1\text{-}4}$-alkyl, and Z is a leaving group or an optionally protected hydroxyl group, and salts thereof, the process comprising performing an asymmetric catalytic hydrogenation reaction in the presence of a transition metal catalyst and a chiral auxiliary, optionally in the presence of a base, applied to a (in case $R^a$ is H), on a compound of formula I or a salt thereof:

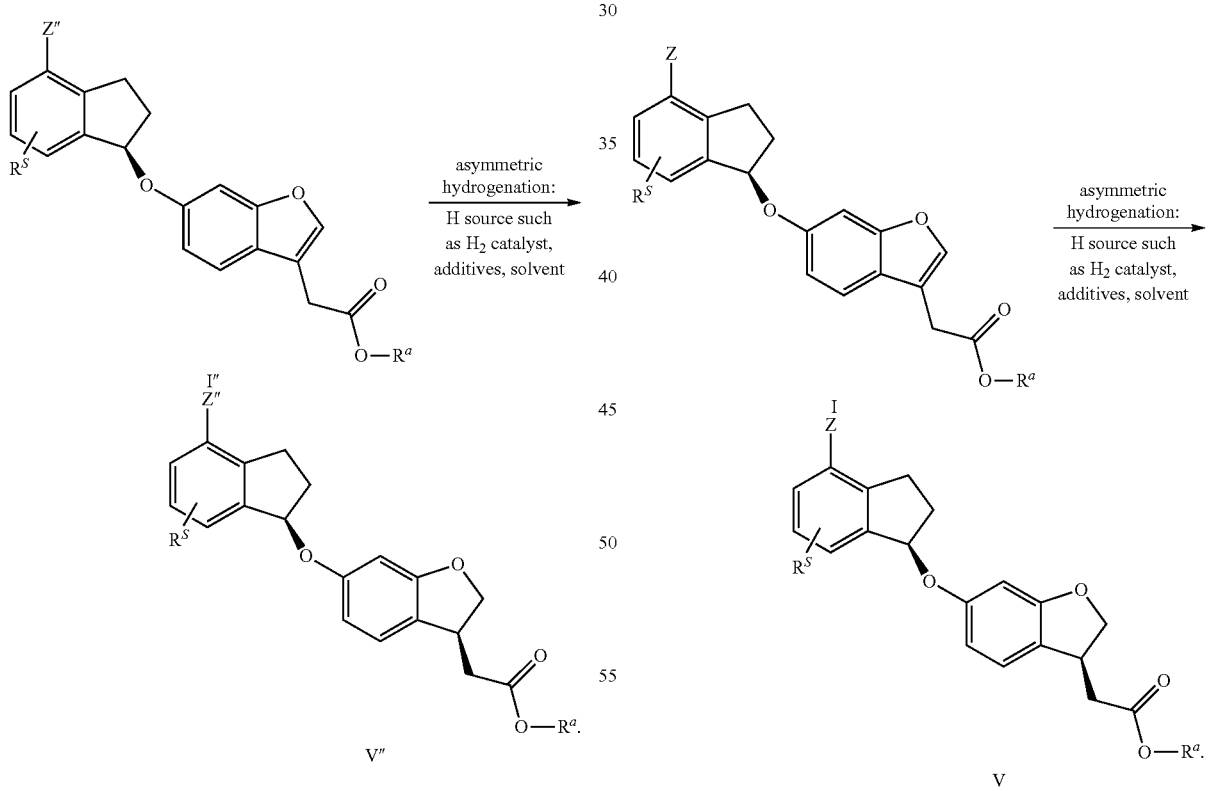

14. The process of claim 13, wherein the transition metal catalyst is Ir, Rh, Ru, Pd, or Fe catalyst.

* * * * *